United States Patent
Watson

(10) Patent No.: US 9,149,254 B2
(45) Date of Patent: Oct. 6, 2015

(54) ALIGNMENT AND IMAGING OF AN EYE WITH AN ULTRASONIC SCANNER

(71) Applicant: ArcScan, Inc., Golden, CO (US)

(72) Inventor: John D. Watson, Evergreen, CO (US)

(73) Assignee: ArcScan, Inc., Morrison, CO (US)

( * ) Notice: Subject to any disclaimer, the term of this patent is extended or adjusted under 35 U.S.C. 154(b) by 54 days.

(21) Appl. No.: 13/684,699

(22) Filed: Nov. 26, 2012

(65) Prior Publication Data

US 2013/0144171 A1    Jun. 6, 2013

Related U.S. Application Data

(63) Continuation-in-part of application No. 12/638,661, filed on Dec. 15, 2009, now Pat. No. 8,317,709.

(60) Provisional application No. 61/122,616, filed on Dec. 15, 2008.

(51) Int. Cl.
  *A61B 8/00*    (2006.01)
  *A61B 8/10*    (2006.01)
  (Continued)

(52) U.S. Cl.
  CPC ............. *A61B 8/10* (2013.01); *A61B 8/0858* (2013.01); *A61B 8/13* (2013.01); *A61B 8/4209* (2013.01); *A61B 8/4461* (2013.01); *A61B 8/4483* (2013.01); *A61B 8/52* (2013.01); *A61B 8/5223* (2013.01); *A61B 8/54* (2013.01)

(58) Field of Classification Search
  CPC ...... A61B 8/10; A61B 8/0858; A61B 8/4209; A61B 8/4483; A61B 8/54; A61B 8/52; A61B 8/13; A61B 8/4461; A61B 8/4223

USPC .................................................. 600/437-469
See application file for complete search history.

(56) References Cited

U.S. PATENT DOCUMENTS

| | | |
|---|---|---|
| 3,371,660 A | 3/1968 | Benson |
| 3,821,891 A | 7/1974 | Collins et al. |
| 3,997,793 A | 12/1976 | Rogers et al. |

(Continued)

FOREIGN PATENT DOCUMENTS

| | | |
|---|---|---|
| CA | 2295431 | 7/2001 |
| CA | 2299483 | 7/2001 |

(Continued)

OTHER PUBLICATIONS

Binder, "SL-OCT and Ultrasound Support the Need for New Phakic IOL Sizing Strategies", Euro Times, Mar. 2007, p. 11.

(Continued)

*Primary Examiner* — Sanjay Cattungal
(74) *Attorney, Agent, or Firm* — Sheridan Ross P.C.

(57) ABSTRACT

A method and apparatus are disclosed for generating accurate and precise ultrasonic images of biological materials or animate objects, such as the cornea and lens of the eye, and, in particular, to an ultrasonic scanning apparatus that can position its virtual center of curvature such that its ultrasonic transducer will emit pulses that reflect substantially perpendicularly from a curved specular surface of interest within the eye. This invention can allow real time imaging of a lens as it accommodates and can better enable researchers and ophthalmic surgeons to develop, fit, implant and diagnose performance of artificial lenses including accommodative lenses.

20 Claims, 35 Drawing Sheets

(51) Int. Cl.
  *A61B 8/08*  (2006.01)
  *A61B 8/13*  (2006.01)

(56) References Cited

U.S. PATENT DOCUMENTS

| | | |
|---|---|---|
| 4,114,214 A | 9/1978 | VonHeck |
| 4,154,114 A | 5/1979 | Katz |
| 4,183,249 A | 1/1980 | Anderson |
| 4,206,763 A | 6/1980 | Pedersen |
| 4,227,780 A | 10/1980 | Ohta et al. |
| 4,245,250 A | 1/1981 | Tiemann |
| 4,347,213 A | 8/1982 | Rogers |
| 4,484,569 A | 11/1984 | Driller et al. |
| 4,493,877 A | 1/1985 | Burnett |
| 4,550,607 A | 11/1985 | Maslak et al. |
| 4,564,018 A | 1/1986 | Hutchison et al. |
| 4,807,634 A | 2/1989 | Enjoji et al. |
| 4,815,047 A | 3/1989 | Hart |
| 4,817,432 A | 4/1989 | Wallace et al. |
| 4,823,801 A | 4/1989 | Sakane |
| 4,858,124 A | 8/1989 | Lizzi et al. |
| 4,858,613 A | 8/1989 | Fry et al. |
| 4,930,512 A | 6/1990 | Henriksen et al. |
| 4,932,414 A | 6/1990 | Coleman et al. |
| 5,029,587 A | 7/1991 | Baba et al. |
| 5,079,786 A | 1/1992 | Rojas |
| 5,103,517 A | 4/1992 | Krouskop |
| 5,116,114 A | 5/1992 | Nakamura et al. |
| 5,293,871 A | 3/1994 | Reinstein et al. |
| 5,331,962 A | 7/1994 | Coleman et al. |
| 5,369,454 A | 11/1994 | Reinstein et al. |
| 5,387,180 A | 2/1995 | Lehmer |
| 5,460,179 A | 10/1995 | Okunuki et al. |
| 5,474,070 A | 12/1995 | Ophir et al. |
| 5,487,388 A | 1/1996 | Rello et al. |
| 5,551,432 A | 9/1996 | Iezzi |
| 5,556,169 A | 9/1996 | Parrish et al. |
| 5,614,099 A | 3/1997 | Hirose et al. |
| 5,626,150 A | 5/1997 | Johnson et al. |
| 5,626,594 A | 5/1997 | Smith |
| 5,776,068 A | 7/1998 | Silverman et al. |
| 5,826,583 A | 10/1998 | Wood |
| 5,832,550 A | 11/1998 | Hauger et al. |
| 5,855,207 A | 1/1999 | Moenning et al. |
| 5,906,205 A | 5/1999 | Hiebert |
| 5,966,763 A | 10/1999 | Thomas et al. |
| 5,971,006 A | 10/1999 | Seigerschmidt |
| 6,053,613 A | 4/2000 | Wei et al. |
| 6,145,143 A | 11/2000 | Hicks et al. |
| 6,154,204 A | 11/2000 | Thompson et al. |
| 6,198,956 B1 | 3/2001 | Dunne |
| 6,315,727 B1 | 11/2001 | Coleman et al. |
| 6,318,372 B1 | 11/2001 | Hiebert |
| 6,334,227 B1 | 1/2002 | Larger |
| 6,374,439 B2 | 4/2002 | Heimbrock et al. |
| 6,460,207 B1 | 10/2002 | Papay et al. |
| 6,487,447 B1 | 11/2002 | Weimann et al. |
| 6,491,637 B2 | 12/2002 | Foster et al. |
| 6,574,813 B2 | 6/2003 | Bolden et al. |
| 6,629,929 B1 | 10/2003 | Jago et al. |
| 6,684,433 B2 | 2/2004 | Giori et al. |
| 6,837,855 B1 | 1/2005 | Puech |
| 6,868,569 B2 | 3/2005 | VanSteenburg |
| 6,887,203 B2 | 5/2005 | Phillips et al. |
| 6,923,767 B2 | 8/2005 | Saied et al. |
| 6,981,417 B1 | 1/2006 | Oravecz |
| 7,048,690 B2 | 5/2006 | Coleman et al. |
| 7,168,116 B2 | 1/2007 | Reger et al. |
| 7,356,905 B2 | 4/2008 | Ketterling et al. |
| 7,451,507 B2 | 11/2008 | Brinkerhoff et al. |
| 7,454,024 B2 | 11/2008 | Ketterling et al. |
| 7,474,041 B2 | 1/2009 | Ketterling et al. |
| 7,480,058 B2 | 1/2009 | Zhao et al. |
| 7,708,342 B2 | 5/2010 | Leach |
| 8,064,989 B2 | 11/2011 | Brown et al. |
| 8,115,935 B2 | 2/2012 | Everett et al. |
| 8,317,709 B2 | 11/2012 | Eilers et al. |
| 2002/0085173 A1 | 7/2002 | Schippert et al. |
| 2002/0143252 A1 | 10/2002 | Dunne et al. |
| 2003/0004416 A1 | 1/2003 | Phillips et al. |
| 2003/0142269 A1 | 7/2003 | Cumming |
| 2004/0220478 A1 | 11/2004 | Wallace et al. |
| 2005/0120479 A1 | 6/2005 | Habashi et al. |
| 2006/0029525 A1 | 2/2006 | Laugharn, Jr. et al. |
| 2006/0241533 A1 | 10/2006 | Geller |
| 2006/0288487 A1 | 12/2006 | Roleder et al. |
| 2007/0083995 A1 | 4/2007 | Purdy et al. |
| 2007/0239030 A1 | 10/2007 | Prager et al. |
| 2007/0276233 A1 | 11/2007 | Besson et al. |
| 2008/0097214 A1 | 4/2008 | Meyers et al. |
| 2009/0192389 A1 | 7/2009 | Eilers et al. |
| 2009/0234369 A1 | 9/2009 | Bax et al. |
| 2010/0004537 A1* | 1/2010 | Eilers et al. .................. 600/443 |
| 2010/0004538 A1* | 1/2010 | Eilers et al. .................. 600/444 |
| 2010/0031448 A1 | 2/2010 | Hijlkema |
| 2010/0217125 A1 | 8/2010 | Kadokura et al. |
| 2010/0229306 A1 | 9/2010 | Reeder et al. |
| 2011/0099718 A1* | 5/2011 | Eilers et al. ........................ 5/637 |
| 2013/0072755 A1 | 3/2013 | Papania et al. |
| 2014/0249422 A1 | 9/2014 | Eilers et al. |

FOREIGN PATENT DOCUMENTS

| | | |
|---|---|---|
| CA | 2395203 | 7/2001 |
| CA | 2409234 | 4/2004 |
| JP | 2006-149001 | 6/2006 |

OTHER PUBLICATIONS

Coleman et al., "Ultrasonography of the Eye and Orbit", Second Edition, published by Lippincott Williams & Wilkins, 2006, pp. 1-186.

Ketterling, "Design and Fabrication of a 40-MHz Annular Array Transducer", IEEE Transactions on Ultrasonics, Ferroelectrics, and Frequency Control, Apr. 2005, vol. 52, No. 4, pp. 672-681.

Ketterling, "Operational Verification of a 40-MHz Annular Array Transducer", IEEE Transactions on Ultrasonics, Ferroelectrics, and Frequency Control, Mar. 2006, vol. 53, No. 3, pp. 623-630.

Mamou, "Chirp-Coded Excitation Imaging With a High-Frequency Ultrasound Annular Array", IEEE Transactions on Ultrasonics, Ferroelectrics, and Frequency Control, Feb. 2008, vol. 55, No. 2.

Pinero et al., "Equivalence, Differences Identified in Biometric Analysis", Cataract & Refractive Surgery Today, Mar. 2008, vol. 3, No. 12, pp. 46-49.

Reinstein, "Subsurface Screening for Keratoconus—Accurate Measurements of the Epithelial and Stromal Layers Aid in Diagnosis", Cataract and Refractive Surgery Today, May 2007, pp. 88-89.

Roholt, "Sizing the Visian ICL", Cataract and Refractive Surgery Today, May 2007, p. 50.

Silverman et al., "Improved System for Sonographic Imaging and Biometry of the Cornea", J. Ultrasound Med., 1997, vol. 16, pp.

International Search Report for International (PCT) Application No. PCT/US09/68089, mailed May 26, 2010.

Written Opinion for International (PCT) Application No. PCT/US09/68089, mailed May 26, 2010.

International Preliminary Report on Patentability for International (PCT) Patent Application No. PCT/US2009/068089, mailed Jun. 30, 2011 8 pages.

Official Action for U.S. Appl. No. 12/638,661, mailed Jun. 4, 2012 8 pages Restriction Requirement.

Notice of Allowance for U.S. Appl. No. 12/638,661, mailed Jul. 24, 2012 9 pages.

Background of the Invention for the above-captioned application (previously provided).

U.S. Appl. No. 13/796,931, filed Mar. 12, 2013, Levien.

International Search Report and Written Opinion for International Application No. PCT/US12/66585, mailed Apr. 12, 2013, 10 pages.

U.S. Appl. No. 13/894,741, filed May 15, 2013, Watson et al.

(56) References Cited

OTHER PUBLICATIONS

U.S. Appl. No. 13/937,948, filed Jul. 9, 2013, Levien et al.
Izatt et al., "Theory of Optical Coherence Tomography," Chap. 2 of "Optical Coherence Tomography Technology and Applications," Drexler and Fujimoto eds, ISBN:978-3-540-77549-2, 2008, pp. 47-72.
Reinstein et al., "Repeatability of Layered Corneal Pachymetry With the Artemis Very High Frequency Digital Ultrasound Arc-Scanner," J. Refractive Surg., vol. 26(9), 2009, original article, 6 pages.
Official Action for Canadian Patent Application No. 2,784,538, dated May 8, 2014, 3 pages.
Angelson et al. "Which transducer array is best?" European Journal of Ultrasound, 1995, vol. 2., pp. 151-164.

* cited by examiner

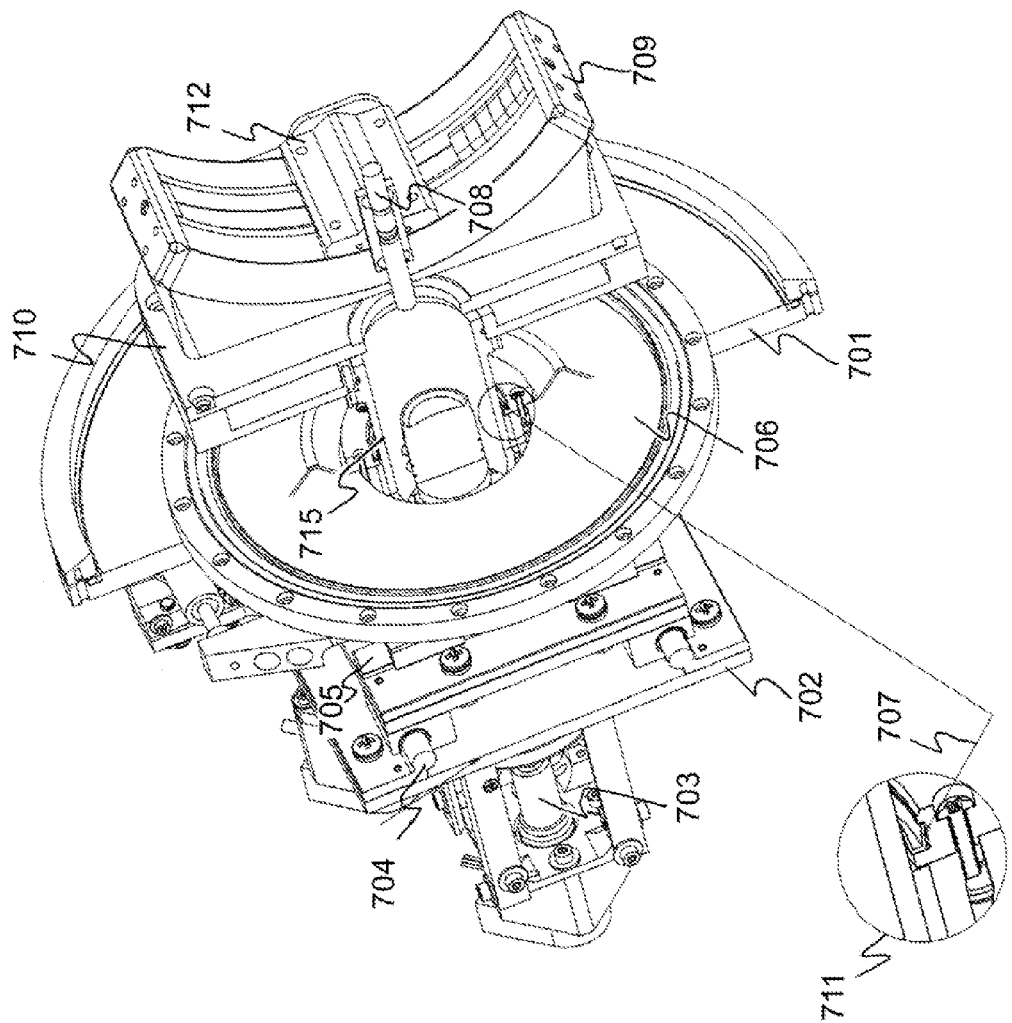
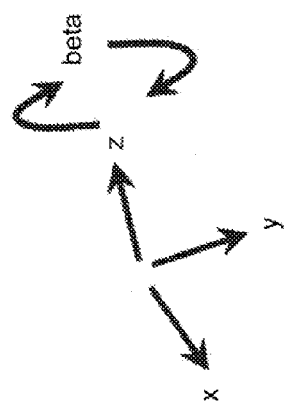
Figure 7

ALIGNMENT AND IMAGING OF AN EYE WITH AN ULTRASONIC SCANNER

CROSS-REFERENCE TO RELATED APPLICATIONS

This application is a continuation-in-part of U.S. patent application Ser. No. 12/638,661 filed Dec. 15, 2009, which claims the benefit of U.S. provisional patent application Ser. No. 61/122,616 filed Dec. 15, 2008. The entireties of the aforementioned applications are incorporated herein by reference.

FIELD

The present invention relates to ultrasonic imaging of biological materials, such as the cornea and natural lens of the eye and, in particular, relates to an ultrasonic scanning apparatuses and methods for positioning and aligning an ultrasonic transducer with respect to an eye component of interest, and for determining speed of sound in a selected region of the eye.

BACKGROUND

Ultrasonic imaging can be used to make accurate and precise measurements of structures of the eye, such as, for example, the cornea and lens. Such measurements provide ophthalmic surgeons with valuable information that they can use to guide various surgical procedures performed on the eye such as LASIK procedures or lens replacements.

Ultrasonic imaging of the cornea and lens presents a problem not generally encountered in other types of tissue. The corneal and lens surfaces are necessarily smooth and gently curved in order to perform their optical function of focusing light rays. Because these structures are smooth and regular, ultrasonic energy is reflected only in specific directions. In particular, an ultrasound pulse from a transducer will only be reflected directly back to that transducer when the pulse is reflected substantially at right angles from the corneal or lens surface. This kind of reflective property is call specular reflection. Because of the specular property of these surfaces, it will be appreciated that special care must be taken to align the transducer with the cornea or lens at each position from which an image segment is to be formed. Ultrasonic imaging of large portions of the cornea or lens can be accomplished by scanning the transducer along the component surface while continually adjusting the alignment of the transducer to provide a sequence of pulses that is always directed through the center of curvature of the specular component, thus ensuring normal reflection.

Corneal and lens imaging and measurement of dimensions require that the scanning motion of the transducer be smooth and precisely aligned. Departures of the transducer axis as small as 5 microns from the pulse's direction through the center of curvature can significantly degrade the resulting image. Mechanisms for performing the requisite scan alignment are described in U.S. Pat. No. 5,331,962, U.S. Pat. No. 6,491,637 and U.S. Pat. No. 6,887,203 which are incorporated herein by reference. Ultrasonic imaging may be used by ophthalmologists for quantitative analysis of laser refractive surgery, implantation of corneal and phakic lenses, implantation of intraocular lenses including accommodative lenses, and specialty procedures such as glaucoma and cataract treatment.

Except for on-axis measurements, images of eye components behind the iris and their dimensions cannot be determined by optical means. New procedures, such as implantation of accommodative lenses, may provide nearly perfect vision without spectacles or contact lenses. Implantation of accommodative lenses requires precision measurements of the natural lens and its suspensory ligaments for successful lens implantation. Such measurements include, for example, lens width, thickness, volume and location relative to the cornea. Ultrasonic imaging can be used to provide the required accurate images of the natural lens especially where its suspensory ligaments, known as zonules, attach to the ciliary body. The equatorial ends of the lens, the zonules and ciliary body are well off the optical axis, behind the iris and therefore not accessible to optical imaging.

Optical imaging devices can be used directly to image accessible portions of the interior of an eye. The speed of light in the cornea, aqueous humor, lens and vitreous humor varies from about 23% less than the speed of light in air to about 29% less than the speed of light in air in the lens. Furthermore the speed of light varies significantly throughout the lens depending on age and other factors. This makes optical measurements which depend on the transmission delays and hence actual speed of light difficult to transform from time delays to distance measurements.

Ultrasonic imaging requires a liquid medium to be interposed between the object being imaged and the transducer, which requires in turn that the eye, the transducer, and the path between them be at all times be immersed in a liquid medium. Many of the principal ultrasonic scanning mechanisms must be therefore submerged in water for long periods.

The speed of sound in the cornea, aqueous humor and lens is about 5 to 7% higher than the speed of sound in water. Furthermore, the speed of sound varies little throughout the lens even in the presence of cataracts. This makes acoustic measurements, which depend on the transmission delays of acoustic pulses, relatively easy to transform from time delays to distance measurements. So, in addition to being able to see the entire lens, acoustic imaging of the lens is less subject to errors in signal speed than optical imaging which is restricted to that portion of the lens visible through the pupil.

Normal ultrasonic imaging practice uses a single transducer for both sending ultrasound pulses to and receiving echoes from eye structures. That arrangement captures only those echoes that return directly to the transducer substantially along the transducer axis.

It is readily demonstrated that specular surfaces only return echoes along the axis of the incident pulse if the incident pulse is directed normal or perpendicular to the surface of the eye component of interest. This behavior has led to the development of ultrasound imaging devices that maintain their incident beam approximately perpendicular to the corneal or lens surface as the incident ultrasound pulses scan the surface. Such a device is described in U.S. patent application Ser. No. 12/347,674, entitled "Components for an Ultrasonic Arc Scanning Apparatus", filed Dec. 31, 2008 and U.S. patent application Ser. No. 12/418,392 entitled "Procedures for an Ultrasonic Arc Scanning Apparatus" filed Apr. 3, 2009, both of which are incorporated herein by reference. With such a device, the incident pulse beam scans in a plane while directing its axis through a fixed center point. If that center point is at or near the center of curvature of the corneal or lens surface, the incident beam will remain approximately perpendicular to the surface throughout the scan, and ultrasound reflections will be returned to the transducer from all scanned parts of the surface.

One method of obtaining an image of the posterior surface of a natural or artificial implanted lens was disclosed in U.S. patent application Ser. No. 12/475,322 entitled "Compound Scanning Head for an Ultrasonic Scanning Apparatus", filed May 29, 2009 which is incorporated herein by reference. This application discloses an ultrasonic arc scanning apparatus with an independently rotatable sector scan head mounted on the carriage of an arc scanning apparatus so as to form a compound scanning head. This invention presents an approach that allows the lens surfaces and cornea surfaces to be imaged at the same time.

There remains a need for more advanced ultrasonic scanning devices and methods that can rapidly produce a series of comprehensive images of the anterior segment of an eye, other than an arc scanner with a fixed radius of curvature such as described in, for example, U.S. Pat. No. 6,887,203.

SUMMARY

These and other needs are addressed by the present invention. The various embodiments and configurations of the present invention are directed generally to ultrasonic imaging of biological materials, such as the cornea and lens of the eye, and, in particular, to an ultrasonic arc scanning apparatus that can move its virtual center of curvature, such that its ultrasonic transducer will emit pulses that reflect substantially perpendicularly from any curved specular surface of interest within the eye.

In one embodiment, a method and imaging device are provided that:
(a) move a first carriage along a linear guide track to generate a first ultrasound scan image of an ocular feature; and
(b) move a second carriage along an arcuate guide track to generate a second ultrasound scan image of the ocular feature.

In another embodiment, a method and imaging device are provided that:
(a) move a first carriage along a linear guide track to displace linearly an ultrasound transducer to image at least one of a tissue and an organ; and
(b) move a second carriage along an arcuate guide track to displace arcuately the ultrasound transducer to image at least one of a tissue and an organ.

In another embodiment, a method and imaging device are provided that:
(a) generate a scan, in proximity to an optical axis of an eye, of at least one of an anterior surface of a cornea, a posterior surface of a cornea, and an anterior surface of a lens;
(b) determine, from the scan, a radius of curvature of the least one of an anterior surface of a cornea, a posterior surface of a cornea, and an anterior surface of a lens;
(c) uses the radius of curvature of the at least one of an anterior surface of a cornea, a posterior surface of a cornea, and an anterior surface of a lens to centrate on the corresponding surface.

In another embodiment, a method and imaging device are provided that:
(a) position a focal plane of an ultrasound transducer in proximity to a lens surface, the lens being a part of an eye of a patient, the eye having an optical axis;
(b) move the transducer linearly in the plane of the meridian but at right angles to the optical axis, while the transducer is positioned substantially at a first angle above an optical axis to form a first ultrasound image; and
(c) move the transducer linearly in the plane of the meridian but at right angles to the optical axis, while the transducer is positioned substantially at a second angle below the an optical axis to form a second ultrasound image.

In another embodiment, a method and imaging device are provided that:
(a) using an ultrasound transducer, generate a scan, in proximity to an optical axis of an eye, of at least one of an anterior surface of a cornea, a posterior surface of a cornea, and an anterior surface of a lens;
(b) determine, from the scan, a radius of curvature of the least one of an anterior surface of a cornea, a posterior surface of a cornea, and an anterior surface of a lens;
(c) use the radius of curvature of the at least one of an anterior surface of a cornea, a posterior surface of a cornea, and an anterior surface of a lens to laterally centrate on the corresponding surface; and
(d) position a focal plane of the ultrasound transducer in proximity to the at least one of an anterior surface of a cornea, a posterior surface of a cornea, and an anterior surface of a lens to axially centrate on the corresponding surface.

The above embodiments can perform combined scans wherein an arc scanner transducer can be moved with one or more degrees of freedom so as to image (1) most of the specular surfaces such as a cornea and a lens and (2) many non-specular features, such as the angle between the cornea and iris lying behind the sclera and the zonules attaching the lens, in a rapid, accurate series of scans that minimize patient motion.

The above embodiments can enable an ultrasonic transducer to be moved in a variety of choreographed motions such that it can be operated to image not only the cornea and lens but also the iris, zonules and ciliary body of the eye, even as the eye being imaged is in the act of accommodating.

The above embodiments can permit centrating an ultrasonic scanner on a desired specular surface within an eye, such as the anterior and posterior surfaces of the cornea and the anterior and posterior surfaces of the lens.

In another embodiment, a method and imaging device are provided that:
(a) generate a B scan of anterior and posterior surfaces of a lens of an eye of a patient in proximity to an optical axis of the lens;
(b) determine, from the B scan, a first determination of lens thickness substantially along the optical axis of the lens;
(c) generate an A scan of anterior and posterior surfaces of the lens in proximity to an optical axis of the lens;
(d) move the transducer along the Z-axis and determining a first Z-axis position wherein the amplitude of the A scan is substantially a local maximum at the anterior surface of the lens;
(e) move the transducer along the Z-axis and determining a second Z-axis position wherein the amplitude of the A scan is substantially a local maximum at the posterior surface of the lens;
(f) generate a second determination of the lens thickness substantially along the optical axis of the lens as the difference between the first and second Z-axis positions; and
(g) compare the first and second lens thicknesses and applying the following rule: when the first and second lens thicknesses are within a first degree of accuracy, determining that a lens thickness is verified.

In another embodiment, a method and imaging device are provided that:
(a) generate, by an ultrasound transducer, a plurality of scans of a lens at different meridian angles; and
(b) form, from the plurality of scans, a three dimensional representation of the lens.

In another embodiment, a method is disclosed for determining a thickness of a selected region of an eye, wherein the selected region is bounded by a first interface and a second interface, comprising: 1) substantially aligning an axis of an ultrasound transducer with a z-axis of a positioning mechanism and at least one of an optical axis of an eye, a visual axis of an eye, and any line passing through both the first interface and the second interface; 2) moving the positioning mechanism and the ultrasound transducer along the z-axis to determine a first z-axis position wherein an amplitude of a first A-scan is substantially a maximum value in proximity of the first interface of the selected region; 3) moving the positioning mechanism and the ultrasound transducer along the z-axis to determine a second z-axis position wherein an amplitude of a second A-scan is substantially a maximum value in proximity of the second interface of the selected region; and 4) subtracting the first axis position from the second z-axis position to determine the thickness of the selected region.

In another embodiment, a method is disclosed for adjusting a B-scan comprised of a plurality of A-scans wherein at least one acoustic velocity measured for an imaged region of an eye is used to convert an acoustic pulse transit time for an imaged region to a distance between a first interface and a second interface of the imaged region.

In another embodiment, a system is disclosed for determining a thickness of a region of an eye wherein the region is bounded by a first interface and a second interface, comprising: 1) a positioning mechanism which can be moved back and forth along a z-axis; 2) a scan head that can be positioned by the positioning mechanism; 3) an ultrasound transducer operably connected to the scan head wherein the ultrasound transducer can be positioned to emit ultrasound pulses along a path coincident with the z-axis of the positioning mechanism; 4) a system for determining a position of the positioning mechanism along the z-axis; and 5) a system for receiving reflected ultrasound pulses.

These embodiments can permit estimating of the on-axis thickness, equatorial diameter, capsule volume and other geometric features of a natural or accommodative lens.

In another embodiment, a method and imaging device are provided that include a a plurality of acoustic transducer sensors mounted on a common transducer shaft, whereby a center transducer is focused on a point along the axis of the transducer shaft and the others are focused on points at an angle of about 1 to about 15 degrees from the axis of the transducer shaft.

The above embodiments can allow, for example, real time imaging of a lens as it accommodates and can better enable researchers to develop artificial accommodative lenses as well as assist ophthalmic surgeons to fit and implant accommodative lenses and then subsequently to diagnose their long term performance.

The following definitions are used herein:

An acoustically reflective surface or interface is a surface or interface that has sufficient acoustic impedance difference across the interface to cause a measurable reflected acoustic signal. A specular surface is typically a very strong acoustically reflective surface.

Animate means of or relating to animal life as opposed to plant life.

Anterior means situated at the front part of a structure; anterior is the opposite of posterior.

An A-scan is a representation of a rectified, filtered reflected acoustic signal as a function of time, received by an ultrasonic transducer from acoustic pulses originally emitted by the ultrasonic transducer from a known fixed position relative to an eye component.

An accommodative lens, also known as a presbyopic lens or presby lens, is an artificial intraocular lens that changes its focal distance in response to contraction of the ciliary body. When successfully implanted, an accommodative lens reverses presbyopia, the inability of the eye to change its focal distance from far to near.

Accuracy as used herein means free from error.

Aligning means positioning the acoustic transducer accurately and reproducibly in all three dimensions of space with respect to a feature of the eye component of interest (such as the center of the pupil, center of curvature or boundary of the cornea, lens, retina, etcetera).

The anterior chamber comprises the region of the eye from the cornea to the iris. The anterior segment comprises the region of the eye from the cornea to the back of the lens.

An aperture refers to the ultrasonic transducer face which may be planar but is commonly shaped as a concave surface so as to form a focal point at a desired location in front of the transducer face.

An arc scanner is an ultrasound scanning device utilizing a transducer that both sends and receives pulses as it moves along an arcuate guide track, which guide track has a center of curvature whose position can be moved to scan different curved surfaces.

Arc scanning transducer center of curvature is the same as the center of curvature of the arc scanning guide.

Auto-centering means automatically, typically under computer control, causing centration of the arc scanning transducer with the eye component of interest.

A B-scan is a processed representation of A-scan data by either or both of converting it from a time to a distance using acoustic velocities and by using grayscales, which correspond to A-scan amplitudes, to highlight the features along the A-scan time history trace (the latter also referred to as an A-scan vector).

A canthus is the angular junction of the eyelids at either corner of the eye where the upper and lower eyelids meet.

Centration means substantially aligning the center of curvature of the arc scanning transducer in all three dimensions of space with the center of curvature of the eye component of interest (such as the cornea, pupil, lens, retina, etcetera) such that rays from the transducer pass through both centers of curvature. A special case is when both centers of curvature are coincident.

The ciliary body is the circumferential tissue inside the eye composed of the ciliary muscle and ciliary processes. There are three sets of ciliary muscles in the eye, the longitudinal, radial, and circular muscles. They are near the front of the eye, above and below the lens. They are attached to the lens by connective tissue called the zonule of Zinn, and are responsible for shaping the lens to focus light on the retina. When the ciliary muscle relaxes, it flattens the lens, generally improving the focus for farther objects. When it contracts, the lens becomes more convex, generally improving the focus for closer objects.

Coronal means of or relating to the frontal plane that passes through the long axis of a body. With respect to the eye or the lens, this would be the equatorial plane of the lens which also approximately passes through the nasal canthus and temporal canthus of the eye.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

A guide is an apparatus for directing the motion of another apparatus.

Haptics are little protrusions extending from the outer diameter of some types of artificial lenses. These haptics fix the position of the lens to the ciliary body by protruding into the ciliary sulcus. In the case of accommodative lenses, the haptics enable the lens to accommodate in response to the action of the ciliary body.

An intraocular lens is an artificial lens that is implanted in the eye to take the place of the natural lens.

LASIK is a procedure performed on the cornea for correcting refractive errors, such as myopia, hyperopia, and astigmatism. Commonly, an excimer laser selectively removes tissue from the inside of the cornea, after it is exposed, by cutting a thin flap, so as to reshape the external shape of the cornea.

As used herein, a meridian is a 2-dimensional plane section through the approximate center of a 3-dimensional eye and its angle is commonly expressed relative to a horizon defined by the nasal canthus and temporal canthus of the eye.

The natural lens (also known as the aqula or crystalline lens) is a transparent, biconvex structure in the eye that, along with the cornea, helps to refract light to be focused on the retina. The lens, by changing shape, functions to change the focal distance of the eye so that it can focus on objects at various distances, thus allowing a sharp real image of the object of interest to be formed on the retina. This adjustment of the lens is known as accommodation. The lens is located in the anterior segment of the eye behind the iris. The lens is suspended in place by the zonular fibers, which attach to the lens near its equatorial line and connect the lens to the ciliary body. The lens has an ellipsoid, biconvex shape whose size and shape can change due to accommodation and due to growth during aging. The lens is comprised of three main parts: namely the lens capsule, the lens epithelium, and the lens fibers. The lens capsule forms the outermost layer of the lens and the lens fibers form the bulk of the interior of the lens. The cells of the lens epithelium, located between the lens capsule and the outermost layer of lens fibers, are generally found only on the anterior side of the lens.

Ocular means having to do with the eye or eyeball.

Ophthalmology means the branch of medicine that deals with the eye.

Optical as used herein refers to processes that use light rays.

The optical axis of the eye is a straight line through the centers of curvature of the refracting surfaces of an eye (the anterior and posterior surfaces of the cornea and lens).

Organ means a differentiated structure (as a heart, kidney or eye) consisting of cells and tissues and performing some specific function in an organism.

Pachymetery or corneal pachymetery is technically referred to as Time Domain Reflectometry ultrasound. A pulse of ultrasonic energy is sent toward the cornea and the time spacing of the returning echoes are used to arrive at corneal thickness.

Phakic intraocular lenses, or phakic lenses, are lenses made of plastic or silicone that are implanted into the eye permanently to reduce a person's need for glasses or contact lenses. Phakic refers to the fact that the lens is implanted into the eye without removing the eye's natural lens. During phakic lens implantation surgery, a small incision is normally made in the front of the eye. The phakic lens is inserted through the incision and placed just in front of or just behind the iris.

Positioner means the mechanism that positions a scan head relative to a selected part of an eye. In the present disclosure, the positioner can move back and forth along the x, y or z axes and rotate in the 0 direction about the z-axis. Normally the positioner does not move during a scan, only the scan head moves. In certain operations, such as measuring the thickness of a region, the positioner may move during a scan.

Posterior means situated at the back part of a structure; posterior is the opposite of anterior.

The posterior chamber comprises the region of the eye from the back of the iris to the front of the lens.

The posterior segment comprises the region of the eye from the back of the lens to the rear of the eye comprising the retina and optical nerve.

Precise as used herein means sharply defined.

Presbyiopia is typically caused by a loss of elasticity of the natural lens inside the eye. This occurs as part of the ageing process and, although it cannot be 'cured', it can be corrected by wearing glasses or implanting an artificial lens.

The pulse transit time across a region of the eye is the time it takes a sound pulse to traverse the region.

Purkinje images are reflections of objects from structure of the eye. There are at least four Purkinje images that are visible on looking at an eye. The first Purkinje image (P1) is the reflection from the outer surface of the cornea. The second Purkinje image (P2) is the reflection from the inner surface of the cornea. The third Purkinje image (P3) is the reflection from the outer (anterior) surface of the lens. The fourth Purkinje image (P4) is the reflection from the inner (posterior) surface of the lens. Unlike the others, P4 is an inverted image. The first and fourth Purkinje images are used by some eye trackers, devices to measure the position of an eye. Purkinje images are named after Czech anatomist Jan Evangelista Purkyně (1787-1869).

Refractive means anything pertaining to the focusing of light rays by the various components of the eye, principally the cornea and lens.

Registration as used herein means aligning.

Scan head means the mechanism that comprises the ultrasound transducer, the transducer holder and carriage as well as any guide tracks that allow the transducer to be moved relative to the positioner. Guide tracks may be linear, arcuate or any other appropriate geometry. The guide tracks may be rigid or flexible. Normally, only the scan head is moved during a scan.

Sector scanner is an ultrasonic scanner that sweeps a sector like a radar. The swept area is pie-shaped with its central point typically located near the face of the ultrasound transducer.

A specular surface means a mirror-like surface that reflects either optical or acoustic waves. For example, an ultrasound beam emanating from a transducer will be reflected directly back to that transducer when the beam is aligned perpendicular to a specular surface.

The ciliary sulcus is the groove between the iris and ciliary body. The scleral sulcus is a slight groove at the junction of the sclera and cornea.

Tissue means an aggregate of cells usually of a particular kind together with their intercellular substance that form one of the structural materials of a plant or an animal and that in animals include connective tissue, epithelium, muscle tissue, and nerve tissue.

A track or guide track is an apparatus along which another apparatus moves.

Ultrasonic means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

A vector refers to a single acoustic pulse and its multiple reflections from various eye components. An A-scan is a representation of this data whose amplitude is typically rectified.

The visual axis of the eye is the line joining the object of interest and the fovea and which passes through the nodal points of the eye.

Zonules are tension-able ligaments extending from near the outer diameter of the crystalline lens. The zonules attach the lens to the ciliary body which allows the lens to accommodate in response to the action of the ciliary muscle.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

BRIEF DESCRIPTION OF THE DRAWINGS

FIG. 7 illustrates a prior art compact arc scanning head positioning mechanism.

DETAILED DESCRIPTION

Figure 3:
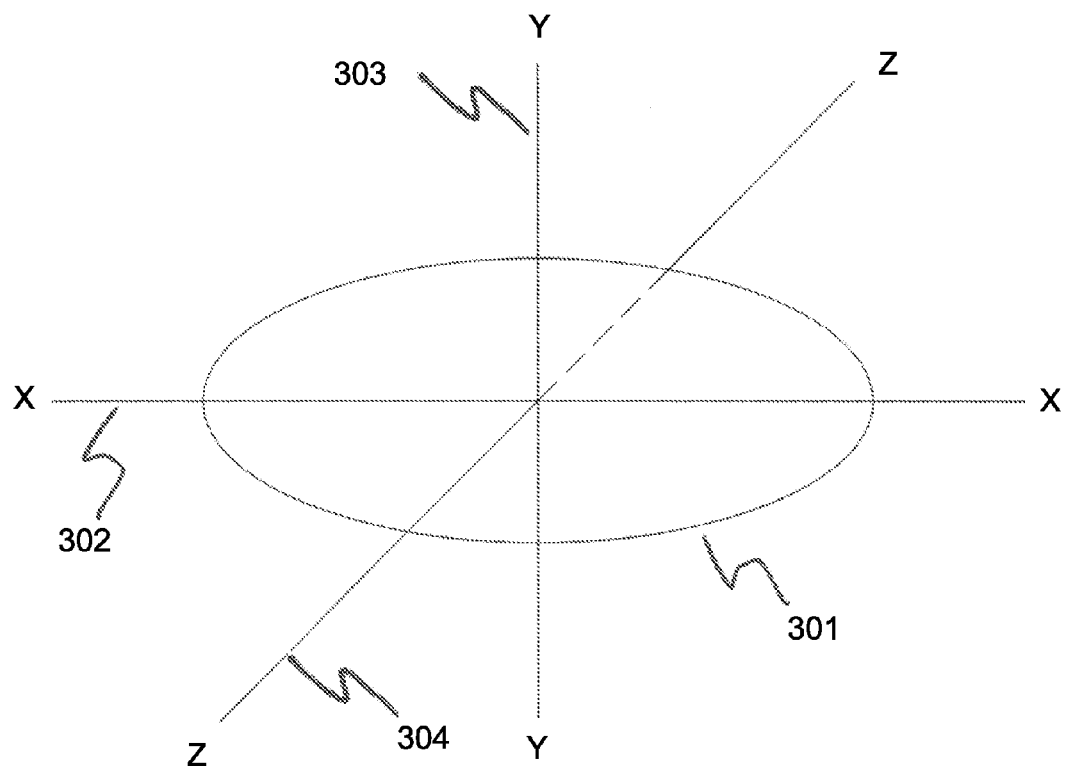
FIG. 3 shows a view of a human crystalline lens showing axes of reference.

In the co-ordinate system of the eye as used herein, the x-direction is substantially parallel to the horizontal equator of the eye (canthus to canthus); the z-direction is substantially along the optical axis of the eye; and the y-direction is perpendicular to the x-z plane of the eye (see FIG. 3).

Figure 1:
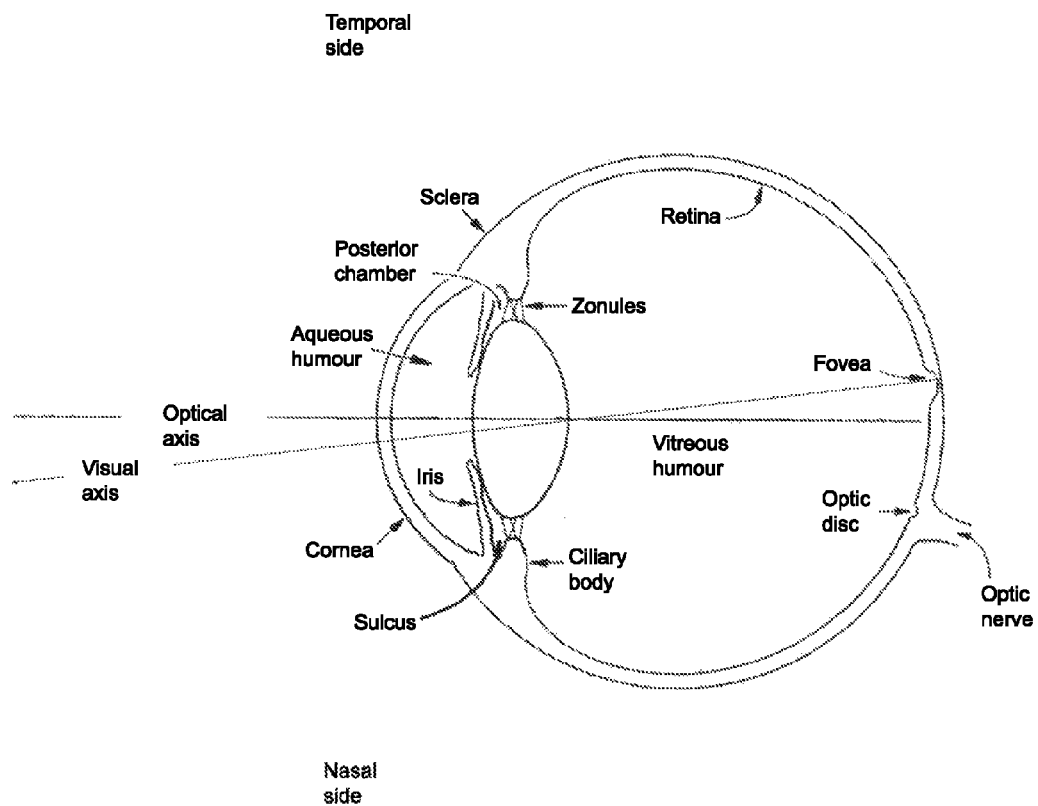
FIG. 1 is a schematic of the main elements of a human eye.

FIG. 1 is a schematic of the main elements of a human eye. The cornea, which is optically transparent, is located at the front of the eye and is located in the anterior chamber. The anterior and posterior surfaces of a normal cornea and the internal layers, such as Bowman's layer, within a normal cornea are specular surfaces. The iris separates the anterior chamber from the posterior chamber. The back of the lens forms the rear of the posterior chamber. The natural lens sits directly behind the iris. Only the central part of the lens, which is behind the pupil, can be seen optically. The anterior and posterior surfaces of a normal lens are specular surfaces. The cornea, iris and lens comprise the main optical refractive components of the eye. The anterior and posterior chambers comprise the anterior segment of the eye. The main volume or posterior segment of the eye lies behind the lens, with the retina and optical nerve at the rear of the posterior segment of the eye. The composition of the eye's aqueous and vitreous humor are very close to that of water with a density of about 1,000 kg/m$^3$, and this allows the eye to be a very good medium for the transmission of acoustic energy.

The optical axis is the line passing through the centers of curvature of the cornea and lens assuming they are centered as they are in a normal eye. The visual axis is the line joining the fixation point and the fovea.

Optical means are suitable for viewing the anterior chamber and for viewing near the entire central axis of the eye. However, optical means cannot be used to view the portions of the posterior chamber lying far off-axis and behind the iris because light does not penetrate the iris. These portions includes the suspensory ligaments (also known as zonules) and the ciliary body. However, the eye components that cannot be viewed optically, can be viewed with suitably high-frequency acoustic energy because high-frequency acoustic energy does penetrate the iris. As is well-known, acoustic frequencies in the ultrasonic range of about 10 MHz to about 100 MHz can be used to provide very high resolution images of, for example, the cornea and the lens. Ultrasound imaging over the above frequency ranges are described in "Ultrasonography of the Eye and Orbit", Second Edition, Coleman et al, published by Lippincott Williams & Wilkins, 2006 which is incorporated herein by reference.

Figure 2:
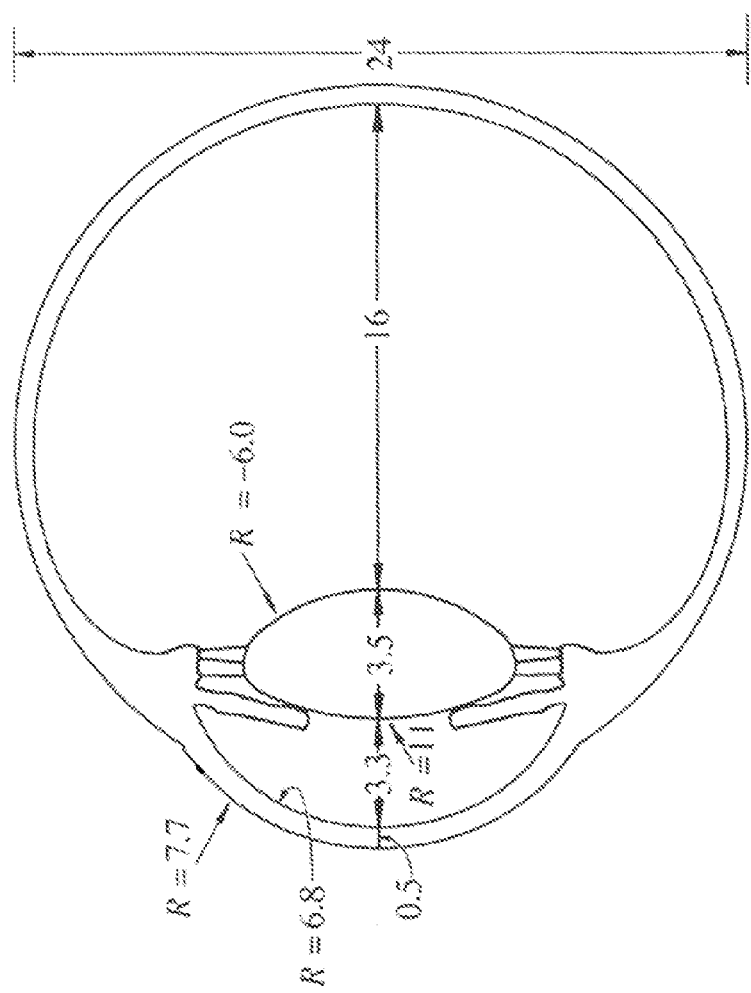
FIG. 2 is a schematic of some of the typical dimensions of the human eye.

FIG. 2 is a schematic of some of the typical dimensions of the human eye in millimeters and these dimensions apply at least along or near the optical axis.

Thickness of cornea~0.5 mm
Radius of curvature anterior cornea surface~7.7 mm
Radius of curvature posterior cornea surface~6.8 mm
Distance from the front of the cornea to the front of the lens~3.3 mm
Thickness of lens~3.5 mm
Radius of curvature anterior lens surface~11 mm
Radius of curvature posterior lens surface~-6.0 mm
Equatorial diameter of lens~8.5 mm to 10 mm
Distance from the rear of the lens to the front of the retina~16 mm These are representative dimensions of the relaxed eye. The distance from the front of the cornea to the front of the lens along the optical axis and the thickness of lens along the optical axis depend upon accommodation. These values were taken from "Optics of the Human Eye", D. A. Atchison, G. Smith, Robert Stevenson House, Edinburgh, ISBN 0 7506 3775 7, first printed in 2000.

The currently accepted acoustic velocities for some eye components, at 37 C, are:

cornea~1639 m/s
aqueous humor~1532 m/s
lens~1641 m/s
cataractous lens~1,629 m/s
vitreous humor~1,532 m/s
sclera (range)~1,583 m/s to ~1,744 m/s These values are from Table 1.1 of "Ultrasonography of the Eye and Orbit", Second Edition, Coleman et al, published by Lippincott Williams & Wilkins, 2006.

For comparison, the acoustic velocity (also known as the speed of sound) in water at 37 C is ~1,520 m/s.

FIG. 3 shows a schematic representation of a lens showing the axes of reference used herein. This figure shows a cross-sectional view of a lens 301 where the x-axis 302 is the major horizontal axis of the lens and passes through the geometric center of the lens. The width of the lens is defined along the x-axis 302. The y-axis 303 is the vertical axis and also passes through the geometric center of the lens. The z-axis 304 is orthogonal to the x-axis 302 and y-axis 303 and is also substantially the same as the optical axis of a normal eye. The lens thickness is defined along the z-axis 304 which also passes through the geometric center of the lens 301.

The lens 301 has an ellipsoid, biconvex shape. In an adult, the lens has a diameter or horizontal width of approximately 9 millimeters. This is the dimension along the x-axis 302 of FIG. 3. The lens has a thickness of approximately 3.5 millimeters. This is the thickness along the z-axis 304 of FIG. 3.

The lens has a height of approximately 9 millimeters. This is the height along the y-axis 303 of FIG. 3.

If the lens is approximately symmetrical about all three axes, then its volume can be approximated as an ellipsoid with the approximate volume of the lens being given by:

$$\text{lens volume} = 4/3\pi abc$$

where
a=the lens half width (major equatorial radius)
b=the lens half height (polar radius)
c=the lens half thickness (minor equatorial radius)

The lens is typically not precisely symmetric about the y-plane and so a lens volume estimation method based on imaging the lens using an accurate and precise imaging device should give a more accurate volume of the lens capsule than an ellipsoid volume approximation.

Figure 4:
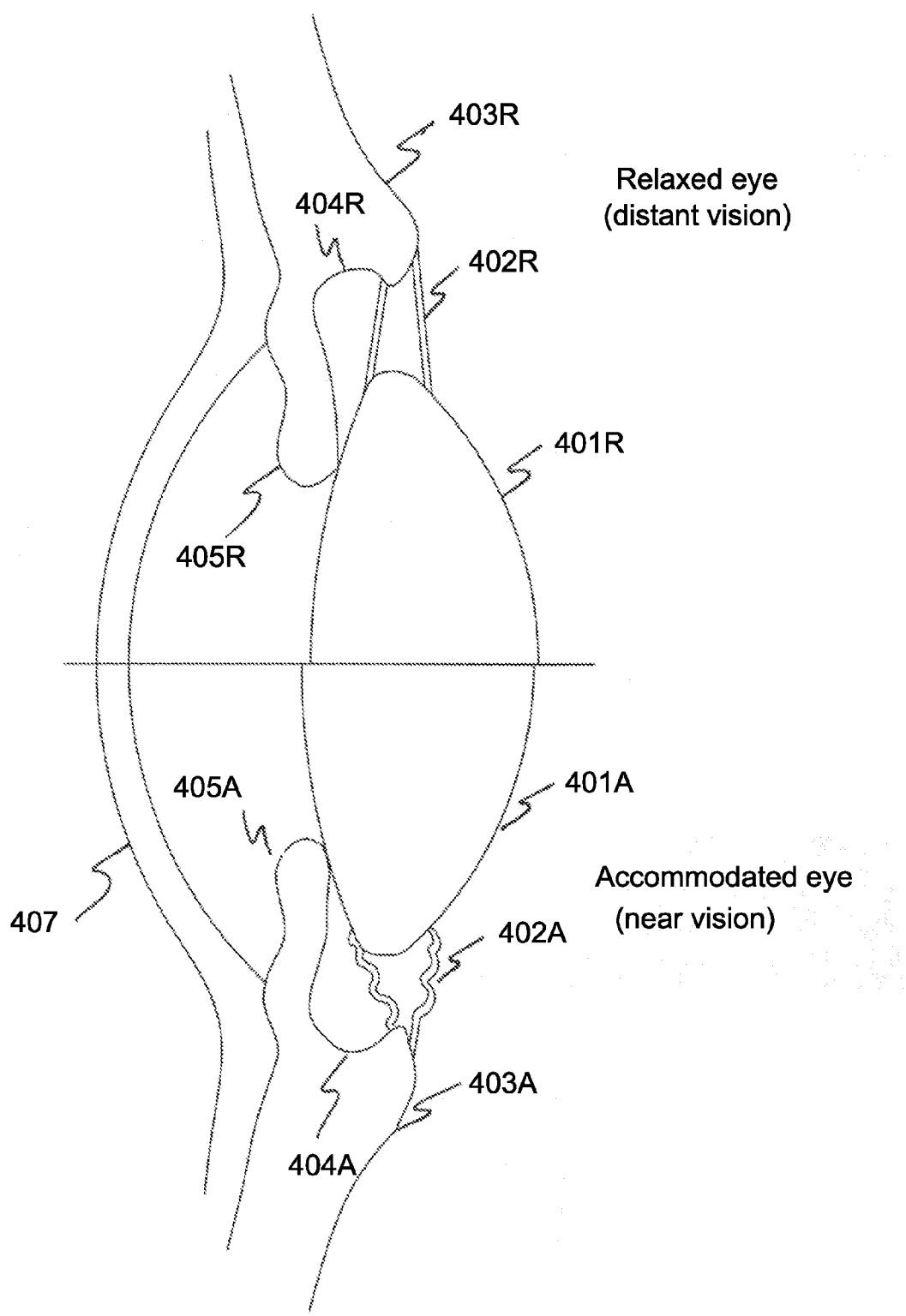
FIG. 4 is a schematic representation of a lens accommodating.

FIG. 4 is a schematic representation of a lens accommodating. The approximate lens shapes in relaxed mode 401R and in accommodative mode 401A are shown. It is commonly believed that when the ciliary muscle 403A contracts inward, the sulcus 404A also contracts inward, tension in the zonules 402A is reduced and this allows the lens 401A to accommodate which is appropriate for near vision. When the ciliary muscle 403R expands outward, the sulcus 404R also expands outward, tension in the zonules 402R is increased and this allows the lens 401R to relax which is appropriate for distant vision. The iris 405R and 405A and cornea 407 are also shown for reference.

There are several theories of exactly how a lens accommodates although there are no accurate and precise devices available for measuring an in-situ lens during accommodation to properly verify these theories. For example, when a relaxed eye (focused for distant vision) accommodates, the inside diameter of the ciliary body 403A contracts which tends to reduce tension in the zonules 402A which, in turn, allows the lens 401A to move and change shape. This contraction also reduces the volume of the posterior segment behind the lens and increases the pressure of the vitreous humor. This tends to push the lens forward and change the shape of the lens. If these lens motions and shape changes can be imaged and if the ciliary body and zonules can be imaged during accommodation, then a better understanding of how accommodation works can be gained. This better understanding can lead to better designs for artificial accommodative lenses.

Once an accommodative lens is implanted or its natural accommodating action restored by, for example, injection of softening agents, an ultrasonic scanner can then be set up to target the region where the lens and the ciliary body are located and/or target the central portion of the lens. The scanner can then be used to generate a series of images that show the ciliary body and lens attachment means responding to the patient focusing at different distances and that show the movement of the central portion of the lens (anterior surface, posterior surface or both) responding to the patient focusing at different distances. If the lens does not accommodate correctly, these images can be used to diagnose the problem areas such as, for example, failure of the haptics of an artificial accommodative lens to function properly, or failure of either anterior lens apex or posterior lens apex to move as the eye attempts to change focus.

These procedures can be repeated from time to time to detect any movement or degradation of the lens, be it a softened natural lens or an artificial accommodating lens.

During the development of the scanning device disclosed herein, it was observed that lens diameter, lens thickness, lens shape and the distance between the cornea and lens varied substantially, even over a small sample of subjects.

Figure 5A:
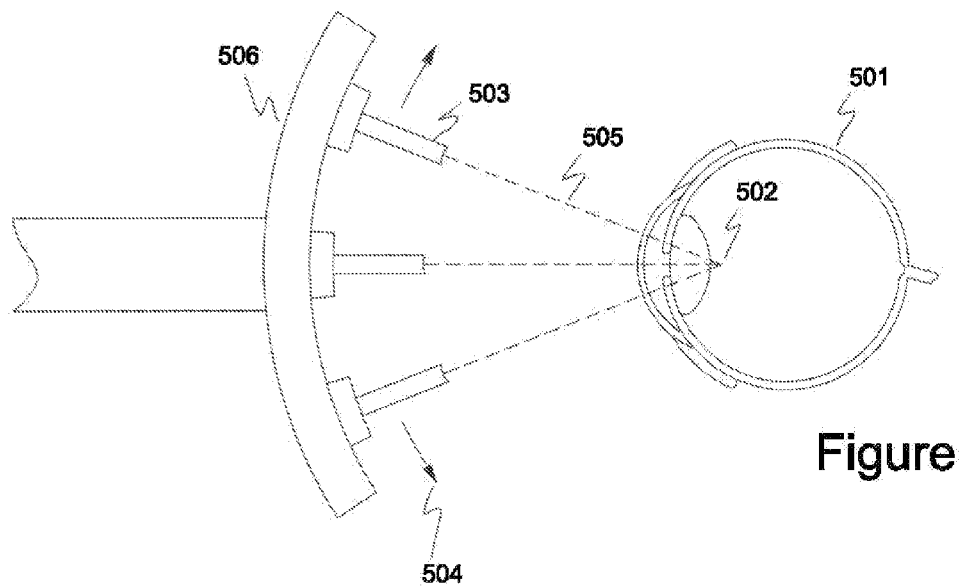
FIGS. 5A and 5B illustrate two different types of scanning strategies for ultrasonic scanners.
Figure 5B:
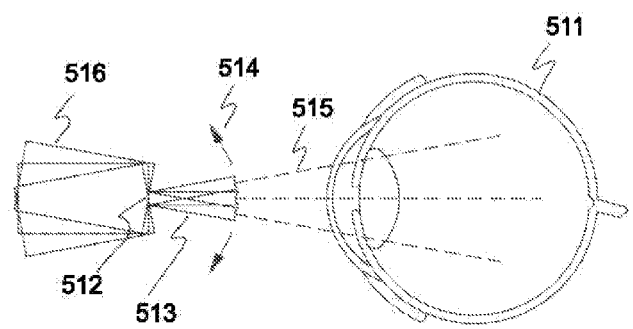

FIGS. 5A and 5B illustrate two different types of prior art scanning strategies for ultrasonic scanners capable of imaging most regions of the interior of an eye. FIG. 5A illustrates the arc scanning principle for producing an ultrasonic scan of a component of an eye 501. In this type of scanner, which is described, for example, in U.S. Pat. No. 7,048,690; U.S. Pat. No. 6,887,203; U.S. Pat. No. 6,491,637; U.S. Pat. No. 6,315,727; U.S. Pat. No. 5,331,962; U.S. Pat. No. 5,293,871; and U.S. patent application Ser. No. 12/347,674, a transducer 503 is moved along an arc guide track 506 whose center of curvature 502 is set approximately at the center of curvature of the eye surface of interest (here shown as the approximate center of curvature of either cornea surface). In FIG. 5A, an ultrasonic transducer 503 is shown in a sequence of positions with the center of curvature of the arc guide 506 at approximately the center of curvature 502 of the cornea (the radii of curvature and the centers of curvature of the anterior and posterior surfaces of the cornea are very close to each other). The transducer 503 is moved in an arc as shown by arrows 504 to produce many acoustic echoes (represented as rays 505) as it moves along the arc guide track 506. The acoustic echoes can then be combined to form a cross-sectional image of the eye features of interest, commonly called a B scan.

FIG. 5B illustrates the sector scanning principle for producing an ultrasonic image of a particular location with an eye 511. In this type of hand-held scanner, which is described, for example, in U.S. Pat. No. 6,198,956, an ultrasonic transducer 516 is shown being oscillated about a fixed position 512, as indicated by arrows 514, so as to produce many acoustic echoes (represented as rays 515). These echoes can then be combined to form of a localized region of interest within the eye. The scanning principle illustrated in this figure is called sector scanning.

In both the arc and sector ultrasonic scanners, the transducer acts as both the transmitter and receiver of acoustic signals. The transducer emits a short acoustic pulse and then receives the reflected acoustic signal. This technique is described, for example, in U.S. Pat. No. 5,293,871 and in "Ultrasonography of the Eye and Orbit", Second Edition, Coleman et al, published by Lippincott Williams & Wilkins, 2006.

A sector scanner can be used to obtain an approximate measurement of the thickness of an eye component such as, for example, the thickness of the cornea or the thickness of the lens along the optical axis. A sector scanner cannot be used to measure the length of specular features that extend laterally, such as, for example, the length of a LASIK scar or lens capsule, because only that small portion of the cornea or lens that is perpendicular to the acoustic beam and reflects acoustic energy back to the transducer is visible to a sector scanner. Thus, to form an image of the entire cornea or lens, a sector scanner must patch together a series of images taken over a period of seconds in which the operator's hand can move and the patient's eye can move. Thus, a sector scanner may be able to make a qualitative image of an accommodating lens but not a quantitatively accurate image.

An arc scanner, on the other hand, can be used to measure the thickness of an eye component such as, for example, the thickness of the cornea or the thickness of a lens as well as to measure the length of specular features that extend laterally, such as, for example, the length of a LASIK scar or the lateral length of a natural or implanted lens. In an arc scanner, the patient is typically looking downward at approximately 45 degrees from horizontal. This is a preferred position for an arc scanning device. Both arc and sector scanners are discussed on page 35 of "Ultrasonography of the Eye and Orbit" cited above.

As will be described below, the present invention discloses apparatuses and methods of producing a combined scan in a way that results in superior and accurately measurable images including substantial portions of lateral extent of both anterior and posterior surfaces of the cornea and lens as well as non-specular features of the eye such as the angle between the cornea and iris lying behind the sclera and the zonules attaching the lens.

Figures 6A, 6B:
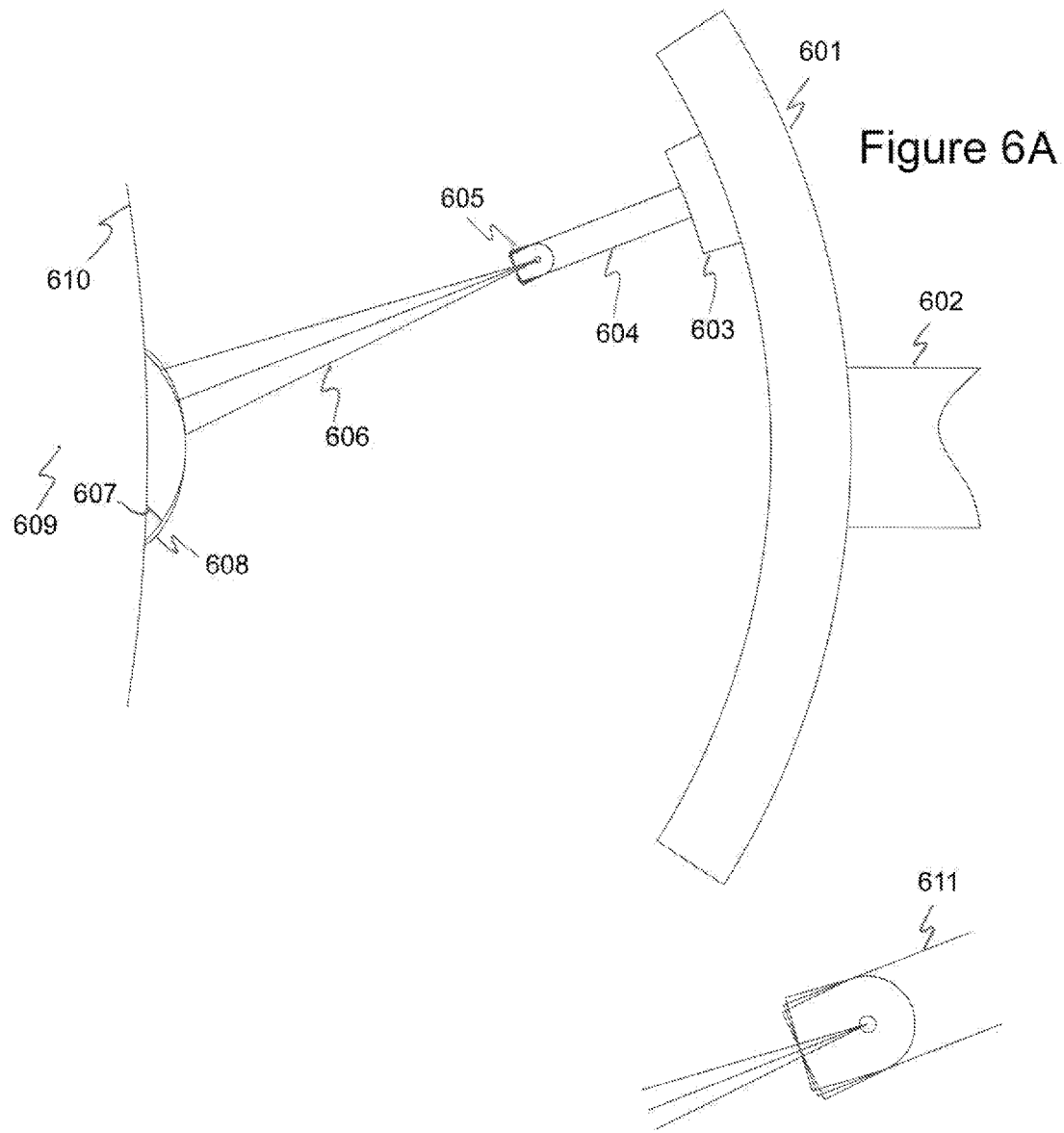
FIGS. 6A and 6B are a schematic of a prior art compound scanning head on an arc scanning device.

FIGS. 6A and 6B are a schematic of a compound scanning head on an arc scanning device which is taken from U.S. patent application Ser. No. 12/475,322. An arc track 601 is shown mounted on a positioning mechanism 602. An example of a positioning mechanism is described in FIG. 7. The positioner 602 orients the arc track 601 such that the center of curvature 609 of the arc track 601 is (1) approximately coincident with the center of curvature of an eye surface of interest (in this example, the surface of interest may be a specular surface 607 on or within the cornea); and (2) such that the plane formed by the arc track 601 and its center of curvature 609 is parallel to a section of interest within an eye component being scanned (in this example, the section of interest may be a desired section through a cornea). A transducer housing 604 is shown mounted rigidly on a transducer carriage 603. A rotatable transducer head 605 is shown mounted on the transducer housing 604. In this figure, the transducer head is shown in three possible positions: normal (aligned with the axis of symmetry of the transducer housing 604), 5 degrees above normal (but still in the plane of the arc track) and 5 degrees below normal (but still in the plane of the arc track). In each position, a transmitted pulse follows a path such as indicated by rays 606. In the normal position, the projected ray passes through the center of curvature 609. In any off-normal position, the projected ray would pass slightly above or below the center of curvature 609.

The surface 607 or 608 of an eye component (such as, for example, the anterior surface of a cornea, the anterior surface of a natural lens or an incision within a cornea) is shown along with a sealing surface 610 which maintains the surface of the eye in a water bath such as described in FIG. 3 of U.S. patent application Ser. No. 12/347,674. Surface 608 is circular and has a constant radius of curvature with its center of curvature approximately at the location of the center of curvature 609 of the arc track 601 and transducer head 605 when the transducer head 605 is in normal position. Surface 607 is slightly elliptical.

In the case of surface 608 with its center of curvature always approximately at the location of the center of curvature 609 of the arc track 601 and transducer head 605, the transmitted pulse will be always be reflected back along its transmission path and a strong received pulse will be captured by the transducer head 605 when in its normal position (aligned with the axis of symmetry of transducer housing 604). When the transducer head 605 is not in its normal position (ie it has moved to an angle above or below its normal position), the strength of the received pulse captured by the transducer head 605 will be diminished, diminishing rapidly as the angle increases away from its normal position.

In the case of slightly elliptical surface 607 with its variable center of curvature, the transmitted pulse will only be reflected back along its transmission path and a strong received pulse captured by the transducer head 605, when the transducer head rotates into a position where the transmitted pulse reflects normally from the surface 607. When the transducer head 605 is at any other angle, the strength of the received pulse captured by the transducer head 605 will be diminished, diminishing rapidly as the angle increases away from the angle at which the transmitted pulse reflects normally from the surface 607.

Thus, for any eye component surface that is not perfectly circular with approximately the same center of curvature as the arc track, the compound, rotatable head will almost always produce a stronger received pulse than a fixed head with its transducer aligned with the axis of symmetry of the transducer housing.

FIG. 6B also includes a close-up 611 of the rotatable transducer head 605 with the transducer head in three possible positions: normal (aligned with the axis of symmetry of the transducer housing 604), 5 degrees above normal and 5 degrees below normal.

Mechanism for General Acoustic Scanning

FIG. 7 illustrates a compact arc scan head positioning mechanism which has been disclosed previously in U.S. patent application Ser. No. 12/347,674. FIG. 7 shows an arc scan head assembly comprised of scan head mount structure 710 and arc guide track 709 with ultrasonic transducer 708 mounted on transducer carriage 712. Transducer carriage 712 may be moved back and forth along arc guide track 709 to perform an arc scan. The scan head assembly is attached to a main positioner arm 715 (shown in a sectional view). The scan head mount structure 710, arc track 709, transducer carriage 712 and transducer 708 are operative under water and are sealed from the rear portion of the positioning mechanism by a translational seal 706 and a rotational seal 707. The translational seal 706 is typically formed by a large rubber membrane that can flex with the small x and y motions required by the positioner, although alternate sealing mechanisms may be employed. The z-axis seal and rotational seal 707 seal against the main positioner arm 715 which can both rotate and move in and out in the z-direction. Translational seal 706 is attached to stationary plate 701 which, in turn, is affixed to the main arc scanner water tank (not shown) which, in turn, is fixed with respect to the patient being scanned. The z-axis and rotational seal 707, which is shown in close-up view 711, is typically formed by a circumferential groove type sealing mechanism with the groove facing into the water, although alternate sealing mechanisms may be employed. Available seals allow both rotation and axial translation of the center tube while maintaining a water tight seal. Plate 702 forms a platform for the x- and y-positioning mechanisms. Plate 702 is fixed relative to stationary plate 701. The scanning head assembly can be moved back and forth axially (the z-direction) by axial piston 703 or another suitable mechanism. The scanning head assembly can be rotated (the beta-direction) about the z-axis by a rotary stepping motor (not shown) or another suitable device. The scanning head assembly can be moved up and down (the y-direction) by piston 705 or another suitable mechanism. The scanning head assembly can be moved from side to side (the x-direction) by piston 704 or another suitable mechanism. The components to the left or rear of stationary plate 701 remain in ambient air while the components to the right or front of stationary plate 701 are in immersed in water when the arc scanner is operational.

Typically, the scan head assembly is moved in the x-, y-, z- and beta directions to position the scan head assembly with respect to an eye component of interest. Although these motions are typically made rapidly under computer control, scans of the eye are typically not made during positioning. Once the scan head assembly is positioned with respect to the eye component of interest, scans are made by the transducer carriage 712 moving back and forth along the arc guide track 709. As described in U.S. patent application Ser. No. 12/347, 674, the transducer carriage 712 moves along arc guide track 709 on a fluid bearing for smooth operation.

As described above, the scanning head can be moved back and forth axially (the z-direction); rotated (the beta-direction) about the z-axis; moved up and down (the y-direction); and moved from side to side (the x-direction). It is therefore possible to move the entire scan head in more complex motions by co-ordinating these movements to obtain scans that cannot be obtained by a simple arc scan. However, the mechanisms of the apparatus of FIG. 7, while suitable for rapid positioning movements, are not well-suited for rapid scanning motions necessary, for example, to obtain multiple images of an eye accommodating in real time. A more suitable device is illustrated in FIGS. 8, 9, 10, and 11.

Figure 8:
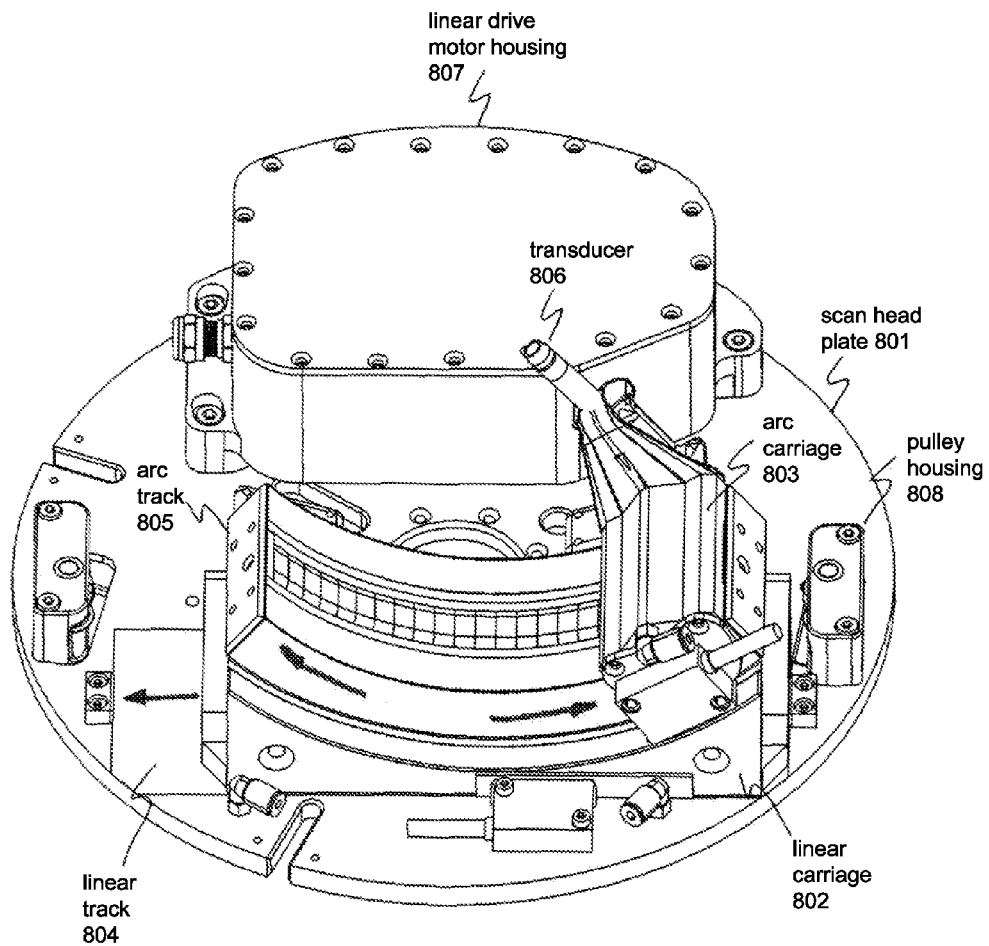
FIG. 8 is a schematic of a first view of a scan head capable of combined motion.

FIG. 8 is a schematic of a first view of a scan head capable of combined motion. The scan head plate 801 replaces scan head mount structure 710 of FIG. 7. Scan head plate 801 serves as the platform for a computer controlled linear carriage 802 and arc carriage 803. Linear carriage 802 moves back and forth along linear guide track 804. Arc carriage 803 moves back and forth along arc guide track 805. In this view, arc carriage 803 is at the rightmost limit of its travel along arc guide track 805 and linear carriage 802 is also at the rightmost limit of its travel on linear guide track 804. As can be appreciated, the motions of arc carriage 803 and linear carriage 802 can be controlled independently. For example, arc carriage 803 can move along arc guide track 805 or be parked anywhere along arc guide track 805 while linear carriage 802 moves along linear guide track 804. As another example, linear carriage 802 can be stationary while arc carriage 803 moves back and forth along arc guide track 805 to execute a pure arc scan. When arc carriage 803 is stationary and linear carriage 802 is moved, this is referred to as a linear scan. When both arc carriage 803 and linear carriage 802 are moved, this is referred to as combined scan. In this configuration, arc carriage 803 is moved along arc guide track 805 by an induction motor as described in U.S. patent application Ser. No. 12/347,674. Arc carriage 803 moves along arc guide track 805 on a fluid bearing which is also described in U.S. patent application Ser. No. 12/347,674. Ultrasound transducer 806 is mounted on arc carriage 803 and the axis of transducer 806 is aligned along the radius of curvature of arc guide track 805. Linear carriage 802 is moved along linear guide track 804 by a drive motor (not shown) housed in linear drive motor housing 807. This drive motor moves linear carriage 802 by a belt and pulley system (not shown except for typical pulley housing 808). Linear carriage 802 moves along linear guide track 804 on a fluid bearing similar to that used between arc carriage 803 and arc track 805. In operation, the scan head assembly of FIG. 8 is under water and is sealed from the x, y, z, beta positioner (shown in FIG. 7) by a sealing means behind the scan head plate. Thus the entire scanning mechanism is positioned with respect to an eye for scanning by the x, y, z, beta positioner shown in FIG. 7, while the actual acoustic imaging scan motion is implemented by one or both of the linear and arc carriages 802 and 803. The scan head assembly disclosed in FIG. 8 allows rapid independent linear and arcuate motion combinations of the transducer such that various scan geometries, explained in subsequent figures, can be implemented to image not only the cornea, iris and anterior lens surface, but also the posterior lens surface, the ciliary body and the zonules that attach the lens to the ciliary body.

Figure 9:
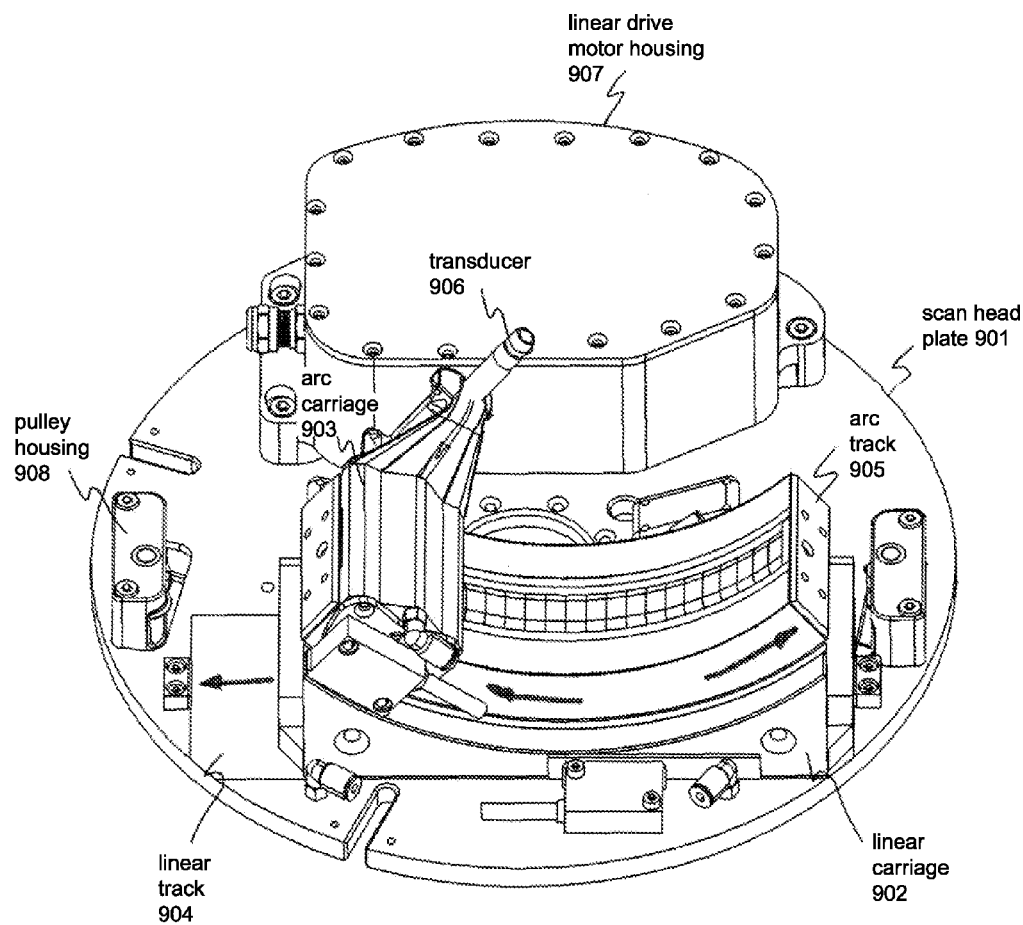
FIG. 9 is a schematic of a second view of a scan head capable of combined motion.

FIG. 9 is a schematic of a second view of a scan head capable of combined motion. In this view, arc carriage 903 is at the leftmost limit of its travel along arc guide track 905 and linear carriage 902 is at the rightmost limit of its travel on linear guide track 904.

Figure 10:
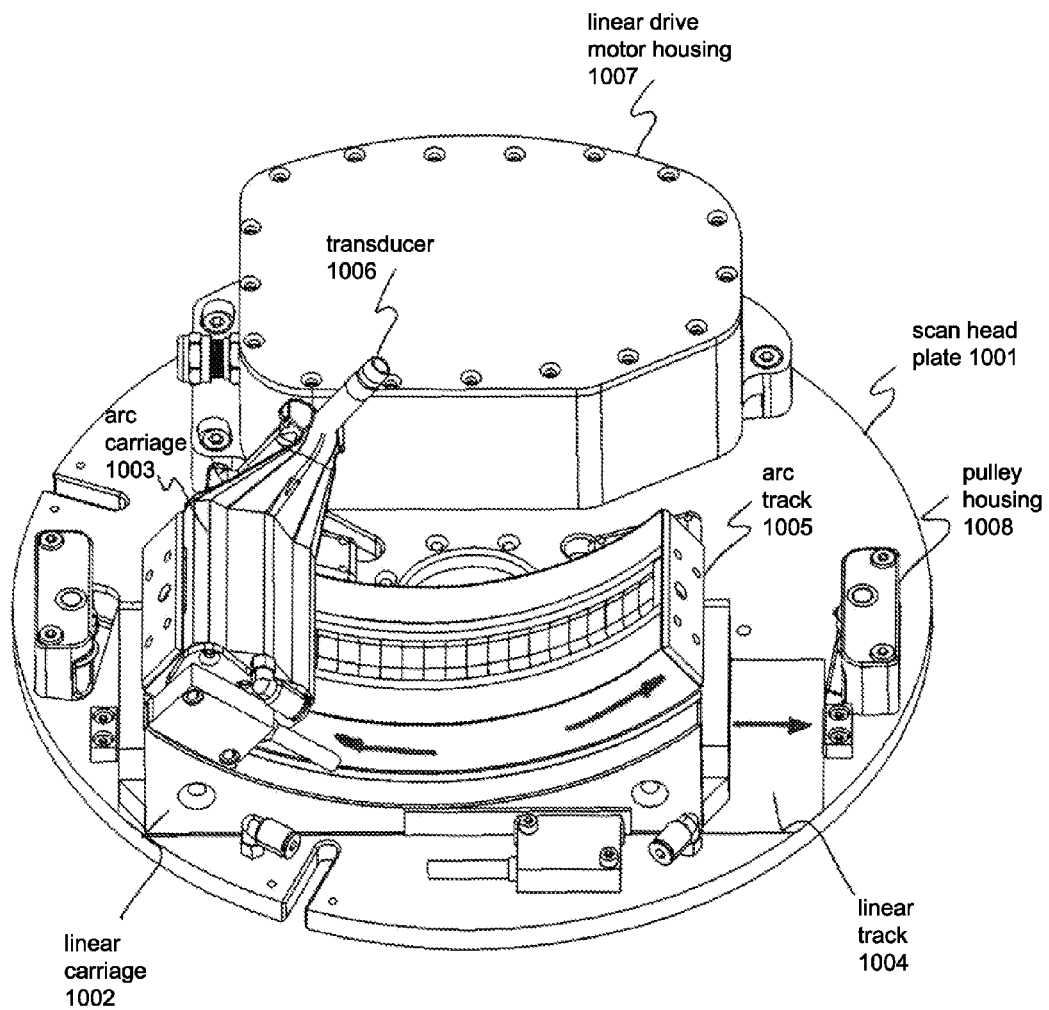
FIG. 10 is a schematic of a third view of a scan head capable of combined motion.

FIG. 10 is a schematic of a third view of a scan head capable of combined motion. In this view, arc carriage 1003 is at the leftmost limit of its travel along arc guide track 1005 and linear carriage 1002 is also at the leftmost limit of its travel on linear guide track 1004.

Figure 11:
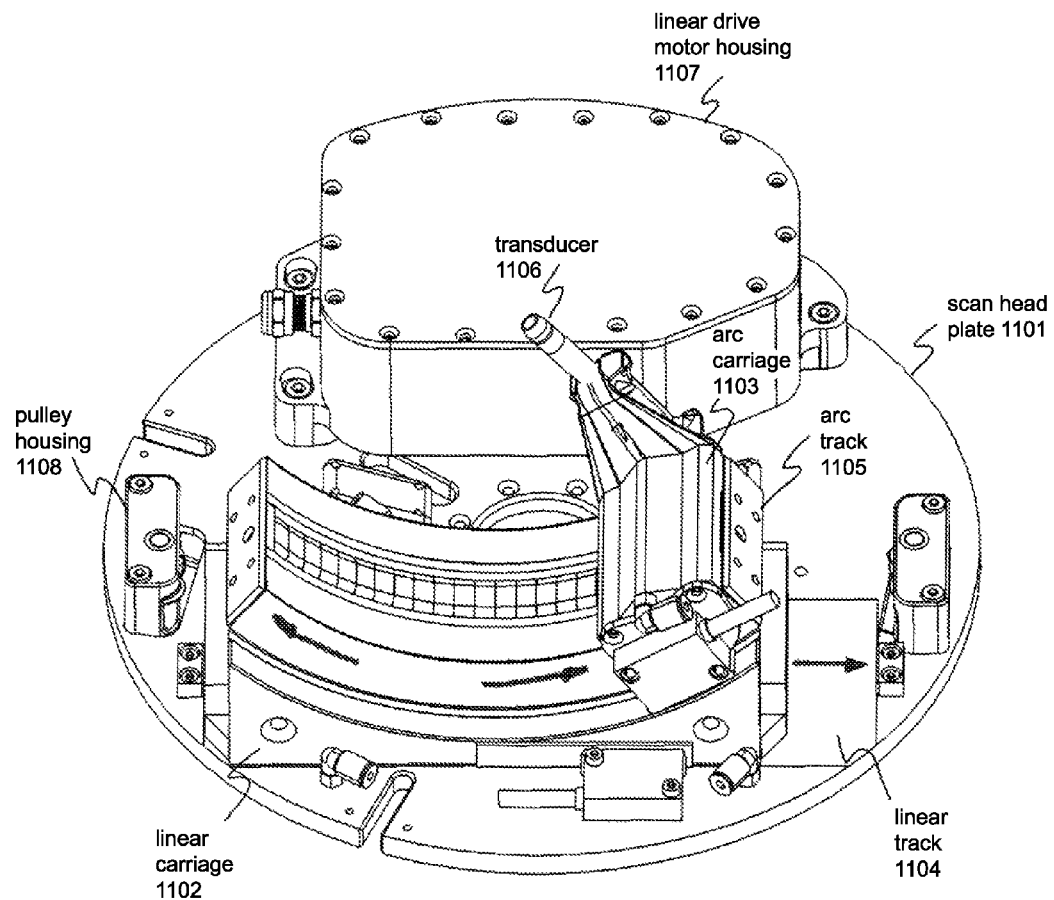
FIG. 11 is a schematic of a fourth view of a scan head capable of combined motion.

FIG. 11 is a schematic of a fourth view of a scan head capable of combined motion. In this view, arc carriage 1103 is at the rightmost limit of its travel along arc guide track 1105 and linear carriage 1102 is at the leftmost limit of its travel on linear guide track 1104.

FIGS. 7 through 11 illustrate an ultrasonic imaging device that can be accurately and precisely positioned with respect to an eye component and then can rapidly acquire accurate and precise images of various eye components by using a combination of arc scans, linear scans and combined arc and linear scans. As can be appreciated, devices incorporating other scan heads can be built so as to move an acoustic imaging transducer in a variety of trajectories to obtain images of various eye components. Although FIGS. 7 through 11 depict an ultrasound imaging device having an arc carriage supported by a linear carriage, it is to be understood that the arc carriage can be separate from the linear carriage, with each carriage having a separate ultrasound transducer.

Relationship of Transducer Center of Curvature and Focal Plane

Figure 12:
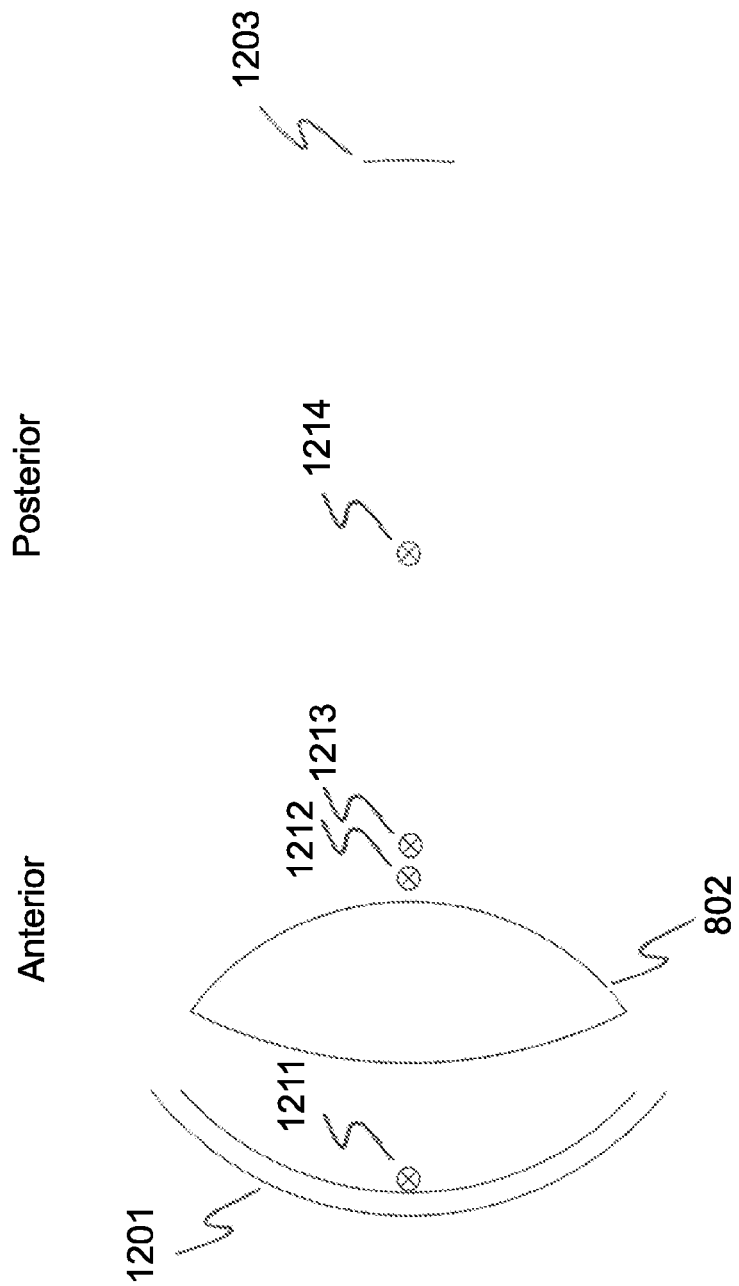
FIG. 12 is a schematic of a typical eye showing centers of curvature.

FIG. 12 is a schematic of a typical eye showing centers of curvature. The front of the eye is on the left. The cornea 1201 is represented by its anterior and posterior surfaces whose centers of curvature are approximately shown by points 1212 and 1213. The lens 1202 is shown by its anterior and posterior surfaces whose centers of curvature are shown by points 1214 (anterior surface center of curvature) and 1211 (posterior surface center of curvature). The position of the retina 1203 relative to the refractory components is also shown.

Figure 13:
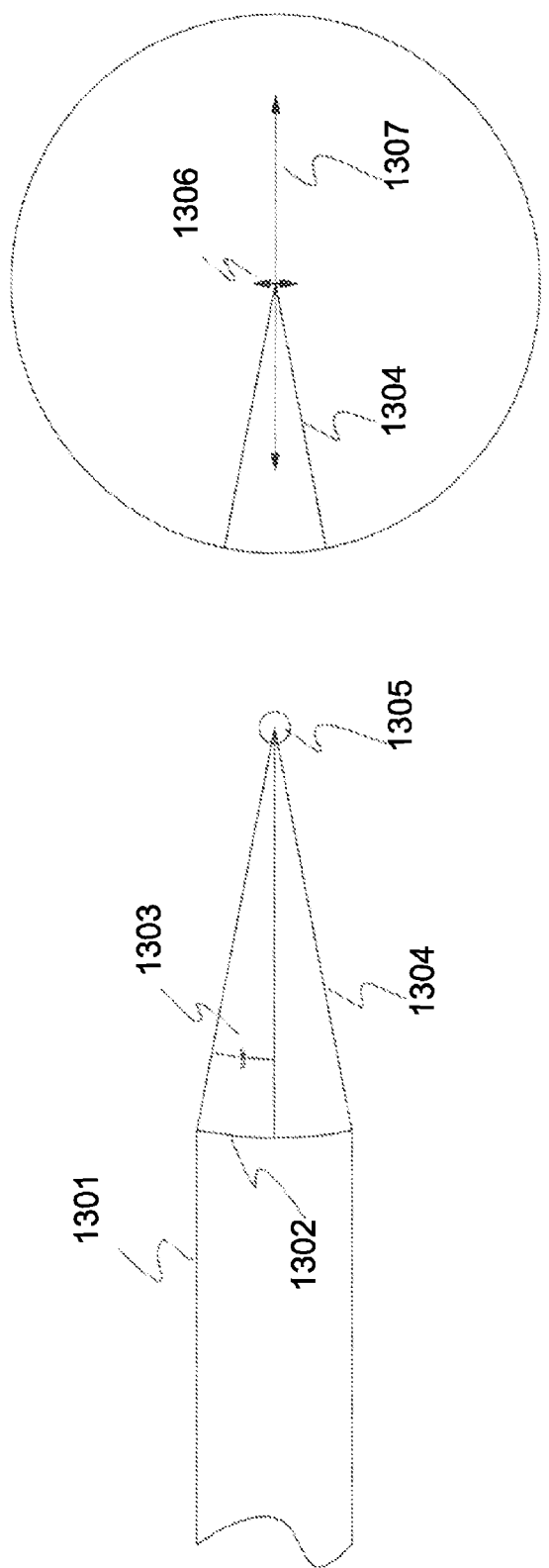
FIG. 13 is a schematic representation of an ultrasonic transducer showing aperture, focal length, depth of focus and lateral resolution.

Typical values for the thicknesses and radii of curvature for the refractive components of the eye shown in FIG. 12 are:
  Thickness of cornea~0.5 mm
  Radius of curvature anterior cornea surface~7.7 mm
  Radius of curvature posterior cornea surface~6.8 mm
  Thickness of lens~3.5 mm
  Radius of curvature anterior lens surface~11 mm
  Radius of curvature posterior lens surface~-6.0 mm FIG. 13 is a schematic representation of a focused ultrasonic transducer showing aperture, focal length, depth of focus and lateral resolution. The transducer has an aperture 1302 which is slightly concave with radius of curvature 1304 that focuses the acoustic pulses at location 1305. Thus, the focal length of the transducer is the distance from the center of the transducer face 1302 to the focal point 1305. The transducer has a depth of focus 1307 and a lateral resolution 1306. The axial resolution is defined in "Ultrasonography of the Eye and Orbit", Second Edition, Coleman et al, published by Lippincott Williams & Wilkins, 2006 as:

$$\Delta axial = cT/2$$

where T=the pulse duration, and
c=the acoustic velocity of the medium

For the example of a transducer with a diameter of 5 mm, a focal length of 15 mm, a center frequency of 38 MHz and a one cycle pulse waveform, the axial resolution is about 20 microns.

Since the focused beam is diffraction limited, the lateral resolution 1306 is usually given by the diameter of the Airy disc:

$$\Delta lateral = 1.22 \lambda f/d$$

where
$\lambda$=the wavelength of the pulse train,
f=the focal length of the transducer and
d=the diameter of the transducer For the example of a transducer with a diameter of 5 mm, a focal length of 15 mm, a center frequency of 38 MHz and a one cycle pulse waveform, the lateral resolution is about 150 microns.

The depth of focus is given by the relationship:

$$\Delta f = \lambda/(4 \sin^2(\theta/2))$$

where $\lambda$=the wavelength of the pulse train,
$\theta$=the half angle subtended by the transducer diameter at the focal point For the example of a transducer with a diameter of 5 mm, a focal length of 15 mm, a center frequency of 38 MHz, the depth of focus is about 1,560 microns.

As can be appreciated, a the transducer with a concave aperture is preferred. In scanning an eye feature of interest, it is typically preferred to place the focal plane of the transducer as close to the feature of interest as possible. As will be seen in later discussions, obtaining a strong, sharp image of an eye feature of interest involves fulfilling 2 conditions: (1) the focal plane must be located near the feature of interest and (2) the transducer pulse must engage the surface of interest substantially normal to the surface. This latter condition can be fulfilled if the pulse wave train passes through both the center of curvature of the transducer arc track guide and the center of curvature of the eye component surface.

A First Method for Centrating

Figure 14A:
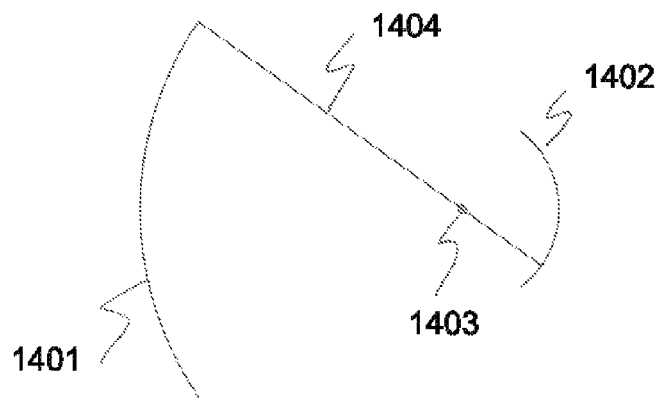
FIGS. 14A, 14B, and 14C are a schematic representation of a first method for centrating an arc scanner on the posterior surface of a lens.
Figure 14B:
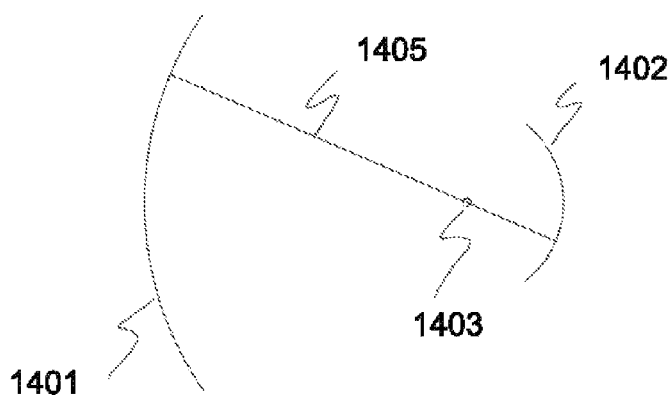
Figure 14C:
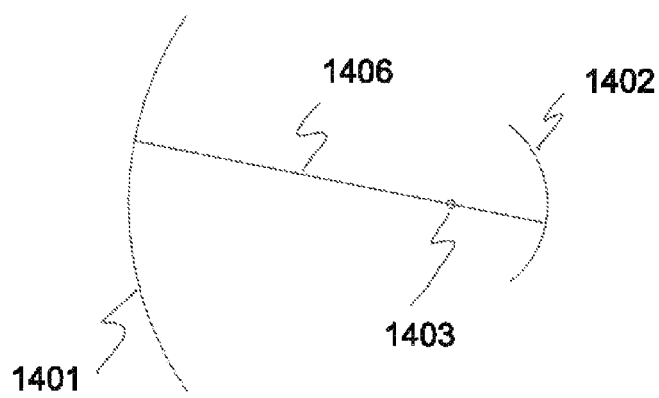

FIGS. 14A, 14B, and 14C are a schematic representation of a first method for centrating an arc scanner on the posterior surface of a lens. In this method, an arc guide track 1401 is positioned so that its center of curvature 1403 is substantially coincident with the center of curvature 1403 of the posterior surface 1402 of a lens. Procedures to accomplish this centration are described in FIGS. 17A, 17B, and 17C, and FIGS. 19A, 19B, and 19C. Now as the transducer carrier moves along the arc guide track 1401, its sonic pulses, represented by rays 1404, 1405 and 1406, always pass through both centers of curvature 1403 and reflect substantially perpendicularly from the posterior surface 1402 of the lens. As can be seen, the length of the pulse path is also constant for all positions of the transducer as it moves along the arc guide track 1401. Thus, it is shown that although the arc guide track may be curved to approximate the curvature of the cornea and anterior lens surface, the same arc guide track can be used to focus and image a surface curved with a radius of curvature of opposite sign such as the posterior surface 1402 of a lens. In the method of FIGS. 14A, 14B, and 14C, the center of curvature the arc guide track 1401 is coincident with the center of curvature 1403 of the posterior surface 1402 of the lens. To centrate on the anterior surface of the lens or on either surface of the cornea, it is also only necessary to position the center of curvature of the arc guide track coincident substantially on the center of curvature of the eye surface being imaged.

A scan of the anterior segment can be made in the following way using this method. First, the arc scanner is centrated on the center of curvature of the anterior surface of the lens and a scan is made moving only the transducer carriage along the arc guide track. This scan will be capable of generating an image of a substantial portion of the anterior surface of the lens and also be capable of generating a low resolution scan of the cornea (since the cornea will typically be further away from the focal plane). Second, the arc guide track can be moved away from the eye in the z-direction to centrate on either center of curvature of the surfaces of the cornea and a scan made again by moving only the transducer carriage along the arc guide track. This scan will be capable of generating an image of a higher resolution image of a substantial portion of the cornea (both surfaces and internal structure since these surfaces are close together and all within reasonable focus). Third, the arc guide track can be moved even further away from the eye in the z-direction to centrate on the center of curvature of the posterior surface of the lens and a scan made again by moving only the transducer carriage along the arc guide track. This scan will be capable of generating an image of a substantial portion of the posterior surface of the lens. These scans can be made in rapid succession (typically on the order of about a second each so as to minimize any movement of the eye by the patient). Since the z-axis motion of the transducer is preferably away from the eye, this would minimize any risk of the transducer assembly being inadvertently moved at high speed toward the eye.

It is noted that, for a transducer of fixed focal length, it is impossible to have the center of curvature of the arc guide track coincident with the center of curvature of three different eye surfaces and be able to place the focal plane of the transducer on each eye surface. Typically, the focal length of the transducer is designed to be inside the cornea when the transducer is centrated on the cornea. In this case, the focal plane of the transducer will not be on the lens surface of interest when the transducer is centrated on the lens surface of interest. This deficiency can be remedied by using dynamic transducer focusing techniques.

The centration method described in FIGS. 14A, 14B, and 14C can be accomplished by an arc scanner apparatus such as described in U.S. patent application Ser. No. 12/347,674.

In FIGS. 21 and 22, an alternate method for centrating will be disclosed that does not require substantial coincidence of the center of curvature of the arc guide track with the center of curvature of the eye surface being imaged.

Figure 15:
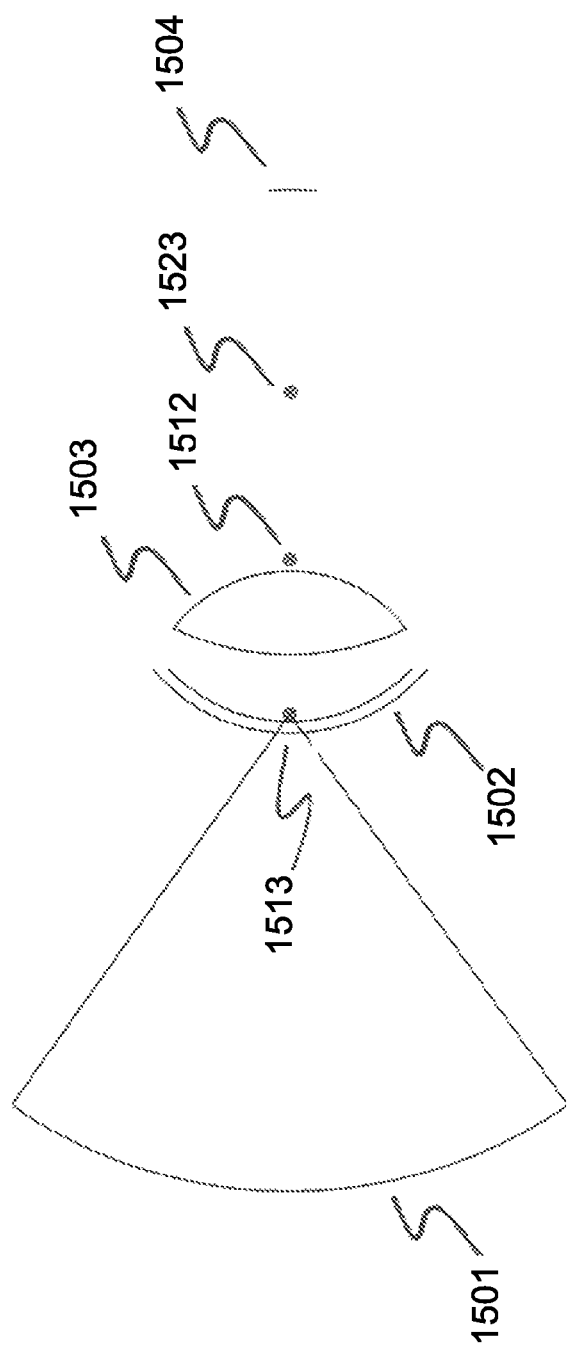
FIG. 15 is an alternative schematic representation of a first method for centrating an arc scanner on the posterior surface of a lens.

FIG. 15 is an alternative schematic representation of the above method for centrating an arc scanner on the posterior surface of a lens. The arcuate path 1501 of a transducer face is shown with its center of curvature centrated on the center of curvature 1513 of the posterior surface of a lens 1503. For reference, the cornea 1502 is shown with its center of curvature 1512. The center of curvature 1523 of the anterior surface of the lens 1503 is shown and for reference the approximate axial location of the retina 1504 is also shown. Typical dimensions of various eye components are shown in FIG. 2. In the setup shown in FIG. 15, an ultrasonic scan will produce a clear image of much of the posterior lens surface and should also produce a partial image of the anterior surface of the lens. The scan may also produce an image of a small region of the cornea on the axis where ultrasonic pulses intercept the cornea at angles near 90 degrees.

Effect of Transducer Focal Length

As noted above, a transducer with a fixed focal length cannot be optimized for imaging the cornea and lens surfaces, even though the transducer can be centrated on each of the cornea and lens surfaces. This is illustrated in Figured 16A and 16B for a transducer centrated on the posterior surface of a lens.

Figure 16B:
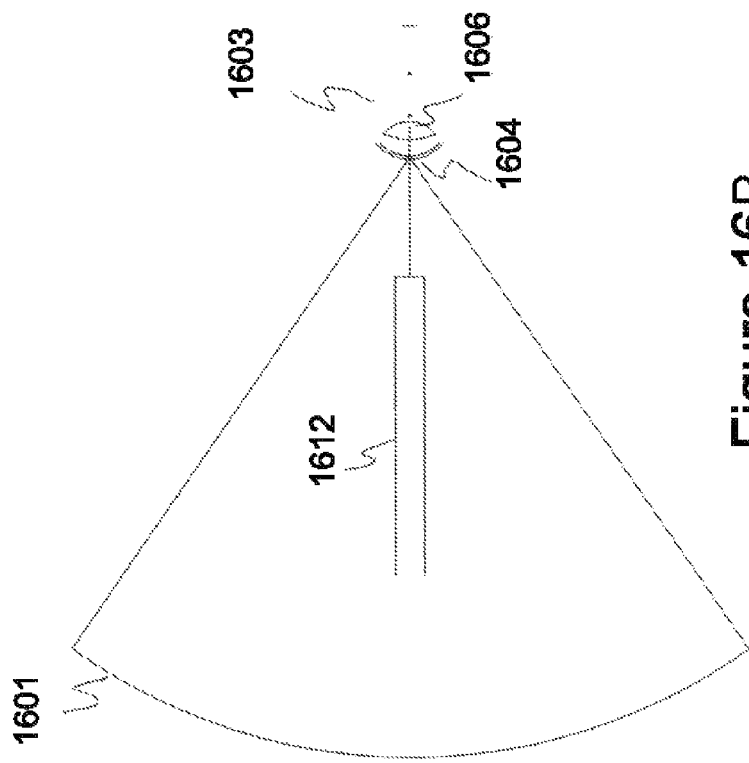
FIGS. 16A and 16B are a schematic representation of varying transducer focal length with an arc scanner centrated on the posterior surface of a lens.
Figure 16A:
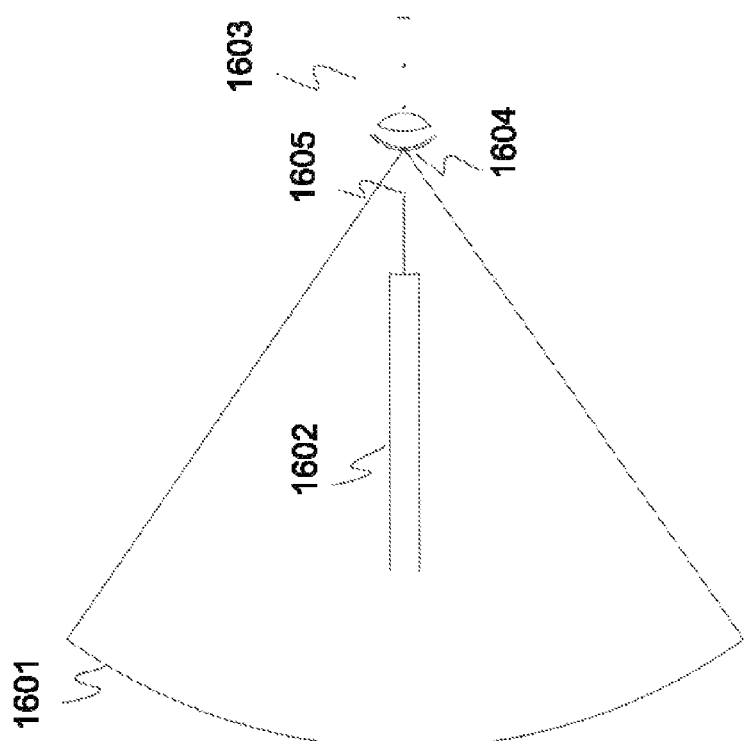

FIGS. 16A and 16B are a schematic representation of varying transducer focal length with an arc scanner centrated on the posterior surface of a lens. FIG. 16A shows a focused ultrasonic transducer 1602 which moves along an arc guide track 1601. The transducer 1602 is shown aligned approximately with the optical axis of an eye 1603 represented by a cornea and a lens. The focal point of the transducer 1602 is represented by the end of the line 1605 and, in FIG. 16A, is shown focused outside the eye. The arc guide track and transducer have a center of curvature 1604 which is centrated on the approximate center of curvature of the posterior surface of the lens. Thus the image of the posterior surface of the lens will be out of focus, even though acoustic pulses will reflect approximately normally from the posterior surface of the lens.

FIG. 16B also shows a focused ultrasonic transducer 1612 which moves along an arc guide track 1601. The transducer 1612 is shown lined up with the approximate optical axis of an eye 1603 represented by a cornea and a lens. The focal point of the transducer 1612 is longer than that of transducer 1602 in FIG. 16A and is represented by the end of the line 1606. In FIG. 16B, transducer 1612 is shown focused approximately in the middle of the lens of the eye. The arc guide track and transducer have a center of curvature 1604 which is centrated on the approximate center of curvature of the posterior surface of the lens. The transducer 1612 of FIG. 16B is thus much better suited to imaging the posterior surface of the lens than the transducer 1602 of FIG. 16A which is not focused near the surface of interest, which in FIGS. 16A and 16B is the posterior surface of the lens. As can be appreciated, the transducer 1602 can be designed to provide a sharp image of the lens surfaces or the cornea surfaces but the same fixed focal length transducer cannot provide sharp images of all surfaces with a single focal length transducer. In practice there is another constraint on the design of transducer focal length. The transducer focal length and arc radius of curvature must allow enough space between the transducer and the eyepiece of the arc scanner for this to be accomplished without endangering the patient's eye by the transducer piercing the membrane separating the water in the arc scanner with the water in the replaceable/disposable eyepiece.

Centrating for Lateral Displacement of Center of Curvature

Figure 17A:
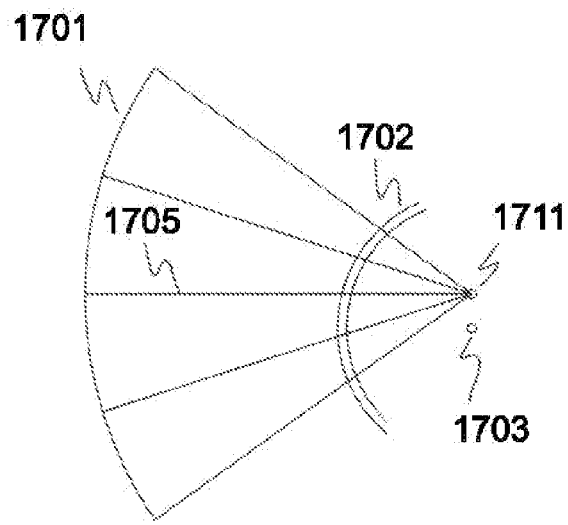
FIGS. 17A, 17B, and 17C illustrate a process of centrating an arc scanner whose center of curvature is laterally displaced.
Figure 17B:
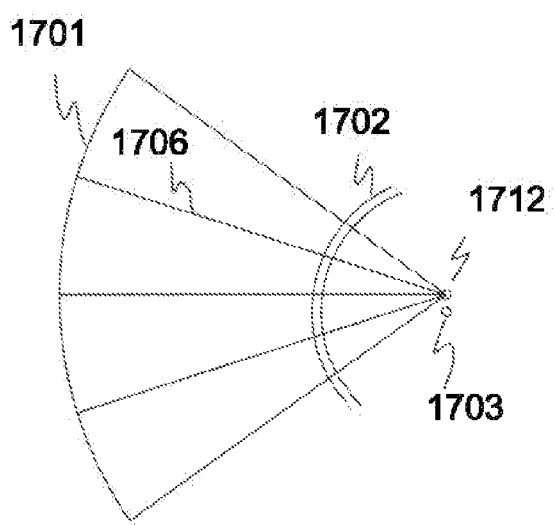
Figure 17C:
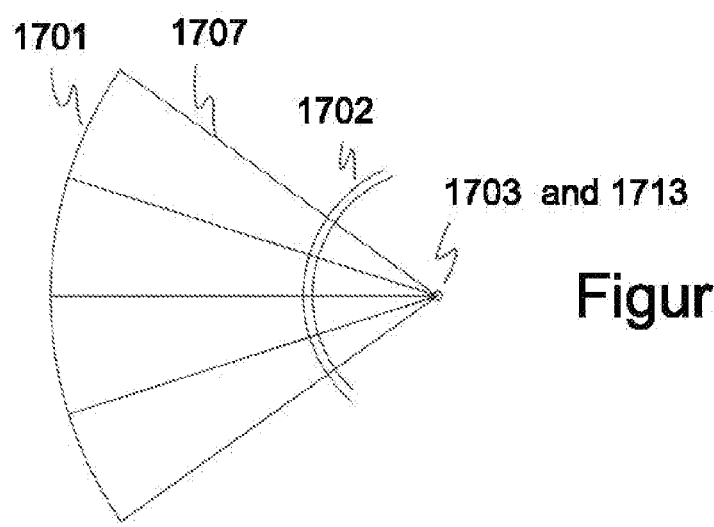

FIGS. 17A, 17B, and 17C illustrate a process of centrating an arc scanner whose center of curvature is laterally displaced from the center of curvature of the eye feature of interest. FIG. 17A shows the arc path 1701 of a transducer face whose center of curvature 1711 is offset laterally from the center of curvature 1703 of an eye component of interest, such as the anterior or posterior surface of a cornea or lens. As the transducer moves along its arc guide track, it sends out ultrasonic pulses such as represented by ray 1705. These pulses pass through the center of curvature 1711 of the transducer but not the center of curvature 1703 of the eye component of interest. Therefore, rays emitted and received at different angular positions along the arc path of the transducer face will have different transit times to and from the eye surface of interest. The raw B-scan image of the cornea generated before correction for curvature of the arc will appear as a line tilted at an angle to the horizontal as further described in FIG. 18. This is because rays emitted and received near the top of the arc in FIGS. 17A, 17B, and 17C have less far to travel than rays emitted and received near the bottom of the arc in FIGS. 17A, 17B, and 17C.

FIG. 17B shows the arc path 1701 of a transducer face whose center of curvature 1712 is offset laterally from the center of curvature 1703 of an eye component of interest but not as far offset as the center of curvature of the transducer of FIG. 17A. As the transducer moves along its arc guide track, it sends out ultrasonic pulses such represented by ray 1706. These pulses pass through the center of curvature 1712 of the transducer but not the center of curvature 1703 of the eye component of interest. The rays emitted and received at different angular positions along the arc path of the transducer will have different transit times to and from the eye surface of interest. The raw B-scan generated before correction for arc curvature will show a line tilted at an angle to the horizontal as further described in FIG. 18 but less tilted than the line generated by the transducer of FIG. 17A.

FIG. 17C shows the arc path 1701 of a transducer face whose center of curvature 1713 is now substantially coincident with the center of curvature 1703 of an eye component of interest. As the transducer moves along its arc guide track, it sends out ultrasonic pulses such represented by ray 1707. These pulses pass through the center of curvature 1713 of the transducer as well as the center of curvature 1703 of the eye component of interest. The rays emitted and received at different angular positions along the arc path of the transducer will have substantially the same transit times to and from the eye surface of interest. The raw B-scan generated before correction for arc curvature will now show a horizontal line as further described in FIG. 18.

In practice only a short scan centered approximately on the optical axis of the eye need be performed to produce a B-scan before correction for arc curvature and the arc guide track positioner can be moved laterally until the scan line is horizontal and this will be the signature that the arc scanner is centrated with no lateral offset. As can be appreciated, this centration adjustment process can be carried out manually or it can be automated and performed under computer control.

It is noted that the curvature of the arc guide track and the curvature the eye component of interest may not be exactly the same. In practice, the centration process for correcting for lateral displacement may not produce a horizontal line when centrated but it will produce a line with minimal tilt and some curvature. Thus in general, the operator centrates by moving the arc guide track until a substantially symmetric line with minimal tilt and curvature is produced.

Figure 18:
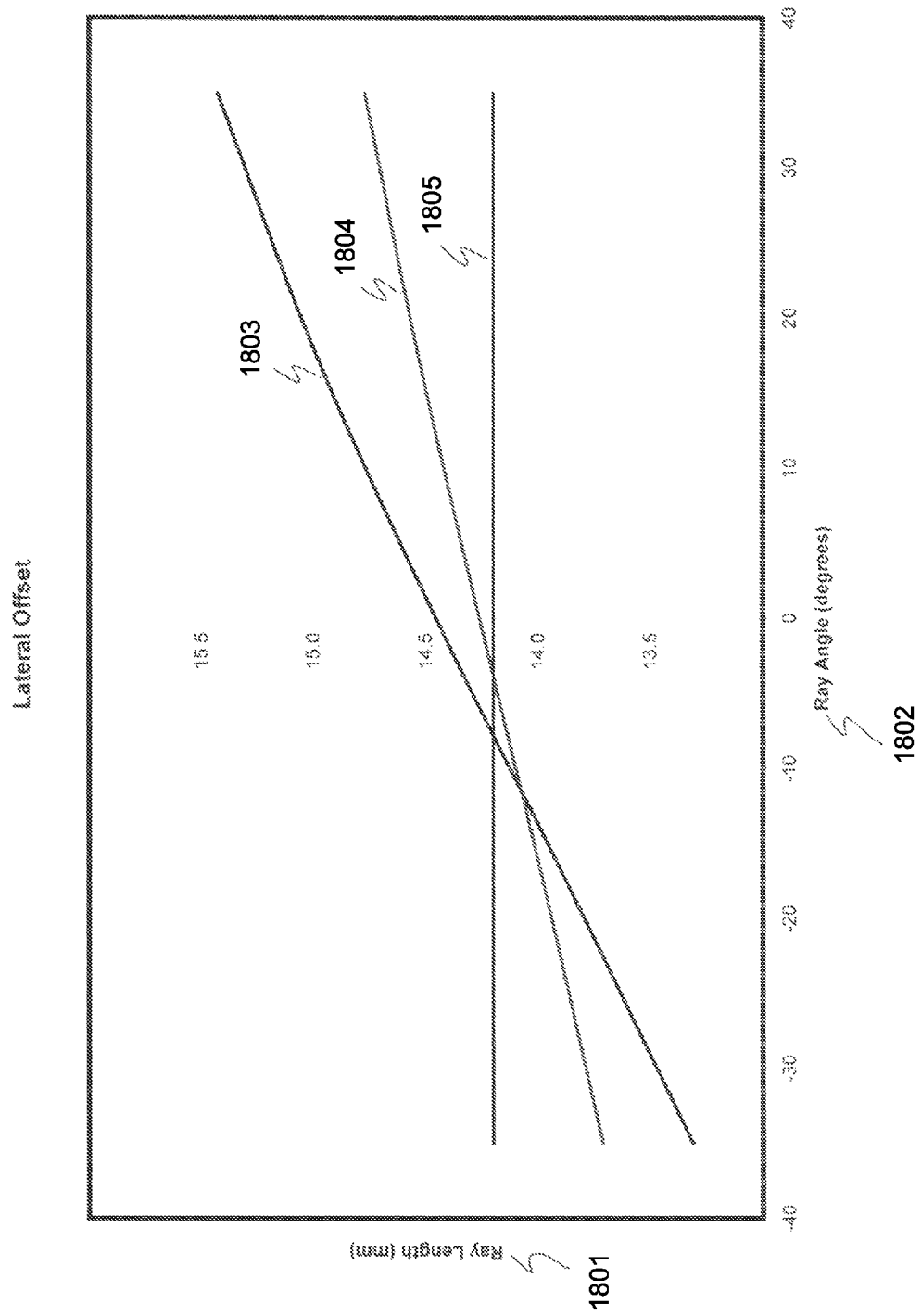
FIG. 18 illustrates a short B-scan where the center of curvature is laterally displaced.

FIG. 18 illustrates a calculated sequence of short B-scans of a locally spherically curved surface with the same curvature as the arc track guide where the centers of curvature are initially laterally displaced. FIG. 18 shows a schematic representation of three raw B-scans generated before correction for arc curvature. The plot shows transit distance (transit time divided by acoustic velocity) for an ultrasonic pulse from the transducer to a curved eye surface and back to the transducer versus angle of the transducer along its arc guide track. Scan 1803 is tilted indicating that the transit times are longer on the positive side of the optical axis and shorter on the negative side of the optical axis. This means that the center of curvature of the transducer is laterally offset from the center of curvature of the eye component surface being measured. As the lateral offset is reduced, the tilt of the scan is also reduces such as shown by scan 1804. When the lateral offset is reduced to zero and the center of curvature of the transducer is coincident with the center of curvature of the eye component surface being measured, then the scan is a horizontal straight line 1805. This means that the arc scanner has been centrated with the eye component surface to be imaged.

Centrating for Axial Displacement of Center of Curvature

Figure 19A:
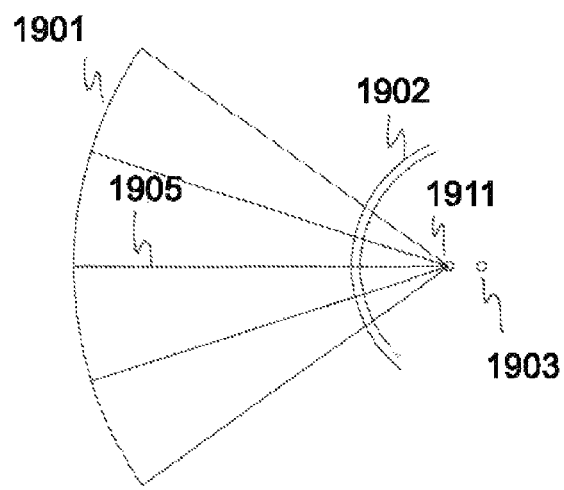
FIGS. 19A, 19B, and 19C illustrate a process of centrating an arc scanner whose center of curvature is axially displaced.
Figure 19B:
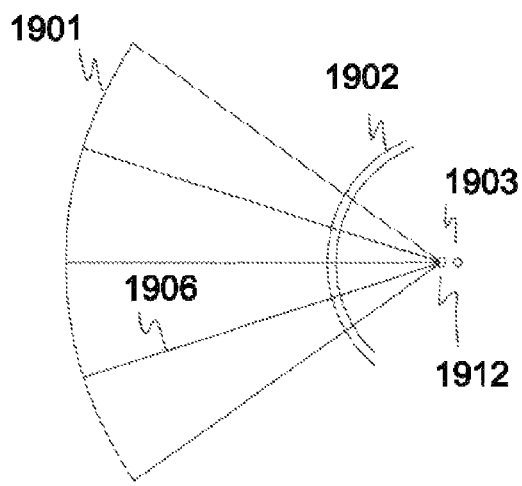
Figure 19C:
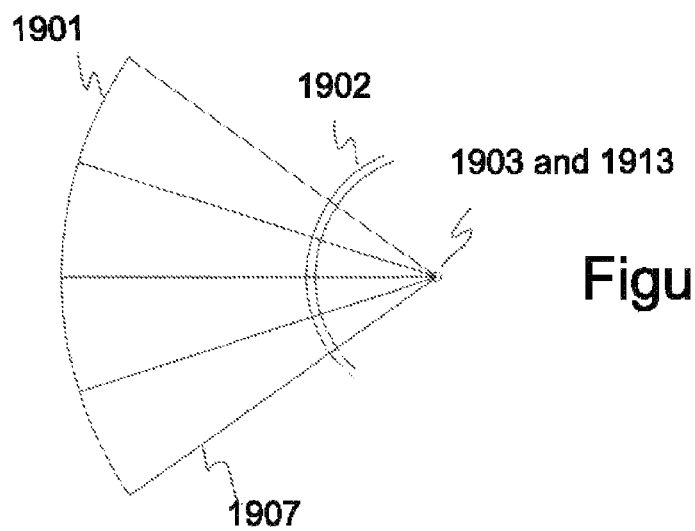

FIGS. 19A, 19B, and 19C illustrate a process of centrating an arc scanner whose center of curvature is axially displaced. FIG. 19A shows the arc path 1901 of a transducer face whose center of curvature 1911 is offset axially from the center of curvature 1903 of an eye component of interest, such as the anterior or posterior surface of a cornea or lens. As the transducer moves along its arc guide track, it sends out ultrasonic pulses such as represented by ray 1905. These pulses pass through the center of curvature 1911 of the transducer but not the center of curvature 1903 of the eye component of interest. Therefore, rays emitted and received at different angular positions along the arc path of the transducer will have different transit times to and from the eye surface of interest. The raw B-scan generated before correction for arc curvature will show a curved line as further described in FIG. 20. This is because rays emitted and received near the center of the arc have a slightly longer distance to travel than rays emitted and received near either the top or bottom of the arc.

FIG. 19B shows the arc path 1901 of a transducer face whose center of curvature 1912 is offset axially from the center of curvature 1903 of an eye component of interest but not as far offset as the center of curvature of the transducer of FIG. 19A. As the transducer moves along its arc guide track, it sends out ultrasonic pulses such represented by ray 1906. These pulses pass through the center of curvature 1912 of the transducer but not the center of curvature 1903 of the eye component of interest. The rays emitted and received at different angular positions along the arc path of the transducer will have different transit times to and from the eye surface of interest. The raw B-scan generated before correction for arc curvature will show a curved line as further described in FIG. 20 but less curved than the line generated by the transducer of FIG. 19A.

FIG. 19C shows the arc path 1901 of a transducer face whose center of curvature 1913 is now substantially coincident with the center of curvature 1903 of an eye component of interest. As the transducer moves along its arc guide track, it sends out ultrasonic pulses such represented by ray 1907. These pulses pass through the center of curvature 1913 of the transducer as well as the center of curvature 1903 of the eye component of interest. The rays emitted and received at different angular positions along the arc path of the transducer will have substantially the same transit times to and from the eye surface of interest. The raw B-scan generated before correction for arc curvature will now show a straight horizontal line as further described in FIG. 20.

In practice only a short scan centered approximately around the optical axis of the eye need be performed to produce a B-scan before correction for arc curvature and the arc guide track positioner can be moved axially until the scan line is not curved and this will be the signature that the arc scanner is centrated with no axial offset. As can be appreciated, this centration adjustment process can be carried out manually or it can be automated and performed under computer control.

As noted previously, the curvature of the arc guide track and the curvature the eye component of interest may not be exactly the same. In practice, the centration process for correcting for axial displacement may not produce a straight line when centrated but it will produce a line with minimal curvature. Thus in general, the operator centrates by moving the arc guide track until a line with minimal curvature is produced.

If an arc scanner is set with its center of curvature both laterally and axially displaced from the center of curvature of an eye component of interest, then the raw B-scan generated before correction for arc curvature will show a tilted curved line. The scanner assembly will then have to be moved both axially and laterally until the tilt and curvature of the raw B-scan generated before correction for arc curvature will show a straight horizontal line at best or at least a line with minimal tilt and curvature. As can be appreciated, this more general centration adjustment process can also be carried out manually or it can also be automated and performed under computer control.

Figure 20:
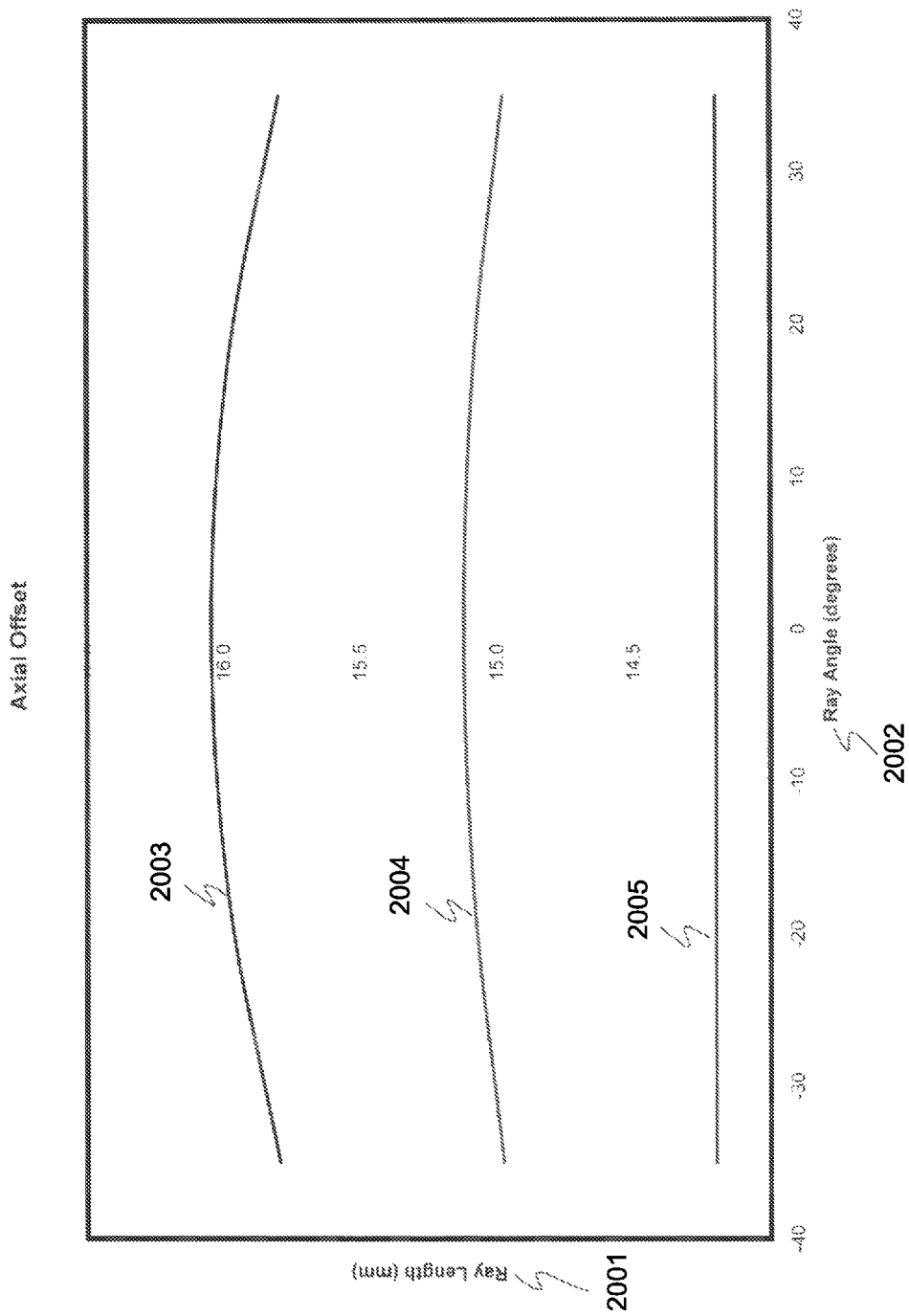
FIG. 20 illustrates a short B-scan where the center of curvature is axially displaced.

FIG. 20 illustrates a calculated series of short B-scans of a locally spherically curved surface with the same curvature as the arc track guide where the centers of curvature are initially axially displaced. FIG. 20 shows a schematic representation of three raw B-scans generated before correction for arc curvature. The plot shows transit distance (transit time divided by acoustic velocity) for an ultrasonic pulse from the transducer to a curved eye surface and back to the transducer versus angle of the transducer along its arc guide track. Scan 2003 is curved indicating that the transit times are shorter as the transducer moves on its track in either direction away from the optical axis. This means that the center of curvature of the transducer is axially offset from the center of curvature of the eye component surface being measured. As the axial offset is reduced, the curve of the scan is also reduced such as shown by scan 2004. When the axial offset is reduced to zero and the center of curvature of the transducer is coincident with the center of curvature of the eye component surface being measured, then the scan is a horizontal straight line 2005. This means that the arc scanner has been centrated with the eye component surface to be imaged.

A Second Method for Centrating

Figure 21A:
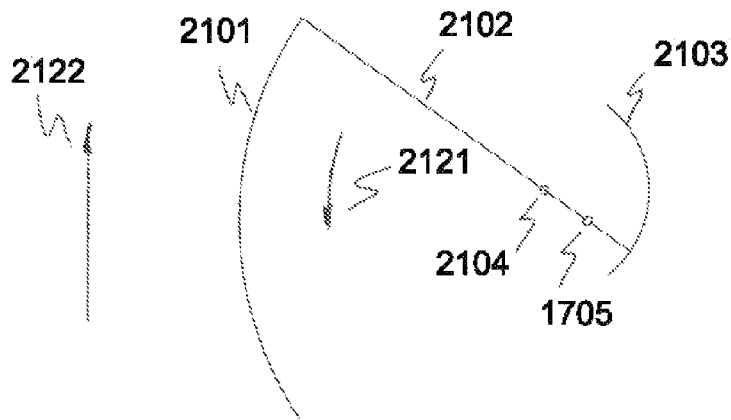
FIGS. 21A, 21B, and 21C are a schematic representation of a second method for centrating an arc scanner on the posterior surface of a lens.
Figure 21B:
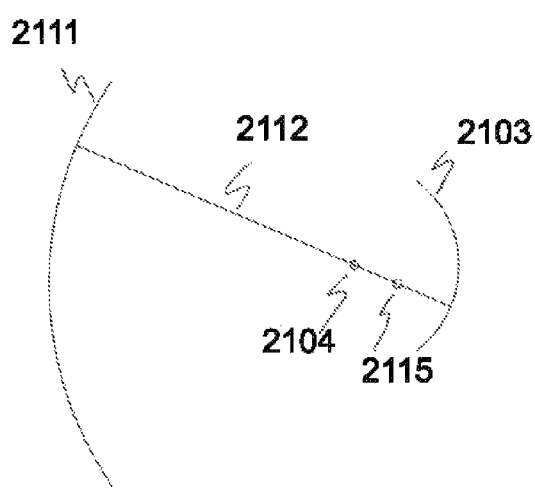
Figure 21C:
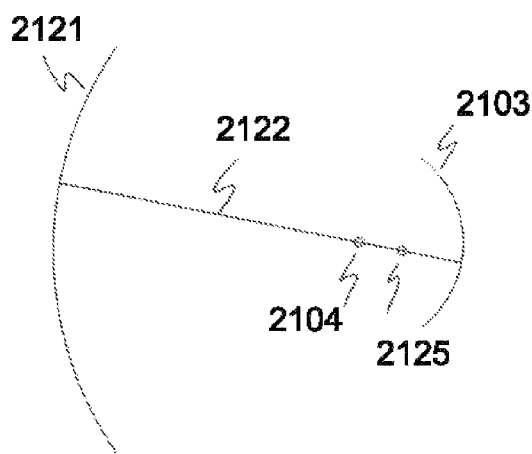

FIGS. 21A, 21B, and 21C are a schematic representation of a second method for centrating an arc scanner, with the method being illustrated on the posterior surface of a lens. In this method, the center of curvature of an arc guide track is not substantially coincident with the center of curvature of an eye component of interest, such as the anterior or posterior surface of a cornea or lens. However, when centration is achieved in this method, an ultrasound pulse emitted by a transducer on the arc guide track always passes through both the center of curvature of the arc guide track and the center of curvature of an eye component of interest. This condition can be met by moving the entire arc guide track laterally as the transducer is moved along the arc guide track. If the separation of centers of curvatures in the z-direction is "$\Delta z$" then the movement of the arc guide track in the x-direction is:

$$\Delta x = \Delta z (\tan \alpha_1 - \tan \alpha_2)$$

where $\alpha_1$=the angle between the transducer axis and the horizontal at time $t_1$ and $\alpha_2$=the angle between the transducer axis and the horizontal at time $t_2$ If, as in FIGS. 21A, 21B, and 21C, the center of curvature of an arc guide track is closer to the surface of the eye component of interest than the center of curvature of an eye component of interest, then the entire arc guide track is moved laterally in the opposite direction as the transducer is moved along the arc guide track as illustrated in FIG. 21A by arrow 2122 denoting the direction of movement of the arc guide track assembly and arrow 2121 denoting the general direction of movement of the transducer.

FIG. 21A shows the arc path 2101 of a transducer face whose center of curvature 2105 is closer to the eye surface of interest 2103 than the center of curvature 2104 of an eye component of interest. It is noted, that by design, the center of curvature of the transducer face arc path is the same as the center of curvature of the arc guide track. As the transducer moves along its arc guide track, it sends out ultrasonic pulses such represented by ray 2102. These pulses pass through the center of curvature 2105 of the transducer arc path 2101 as well as the center of curvature 2104 of the eye component of interest.

FIG. 21B shows the arc path 2111 of a transducer face whose center of curvature 2115 is closer to the eye surface of interest 2103 than the center of curvature 2104 of an eye component of interest. As the transducer moves along its arc guide track, the entire arc guide track assembly moves in the opposite direction as described above. As the transducer moves along its arc guide track, it sends out ultrasonic pulses such represented by ray 2112. These pulses pass through the center of curvature 2115 of the transducer arc track 2111 as well as the center of curvature 2104 of the eye component of interest.

FIG. 21C shows the arc path 2121 of a transducer face whose center of curvature 2125 is closer to the eye surface of interest 2103 than the center of curvature 2104 of an eye component of interest. As the transducer moves along its arc guide track, the entire arc guide track assembly moves in the opposite direction as described above. As the transducer moves along its arc guide track, it sends out ultrasonic pulses such represented by ray 2122. These pulses pass through the center of curvature 2125 of the transducer arc path 2121 as well as the center of curvature 2104 of the eye component of interest.

The rays 2102, 2112 and 2122 are all of slightly differing lengths becoming shorter as the transducer moves along the arc guide track. However, the change in transit time of the transmitted and received ultrasonic pulses can be corrected by the known geometric relationships since the positions of the transducer on the arc guide track and the position of the arc guide track assembly are known accurately at all times. The key point here is that the rays 2102, 2112 and 2122 all reflect normally off the surface of the eye component of interest. In the case illustrated in FIGS. 21A, 21B, and 21C, the arc scanner is able to image the posterior surface of the lens even though the curvature of the posterior lens surface and the curvature of the arc guide track are of opposite sign.

As an example of the range of motions illustrated in FIGS. 21A, 21B, and 21C, the center of curvature of transducer face (R=20 mm) is about 2.466 mm closer to the eye component than the center of curvature of the posterior surface of the lens (R=6 mm).

| Transducer angle with respect to the horizontal (degrees) | Lateral displacement of arc track between adjacent angular movements (mm) |
| --- | --- |
| 35.000 | 0.0000 |
| 23.045 | 0.6775 |
| 11.090 | 0.5656 |

Figure 22A:
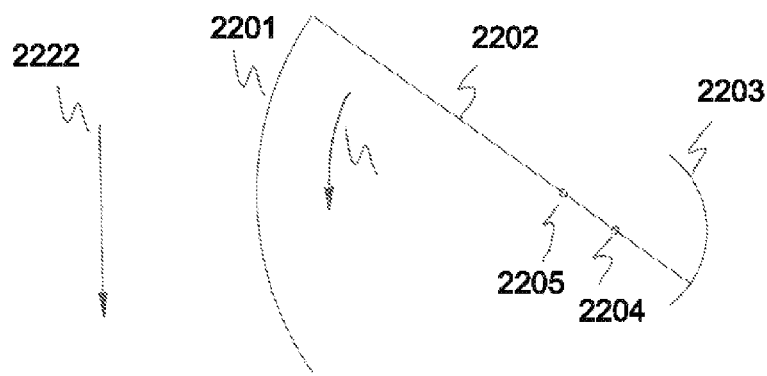
FIGS. 22A, 22B, and 22C are another schematic representation of a second method for centrating an arc scanner on the posterior surface of a lens.
Figure 22B:
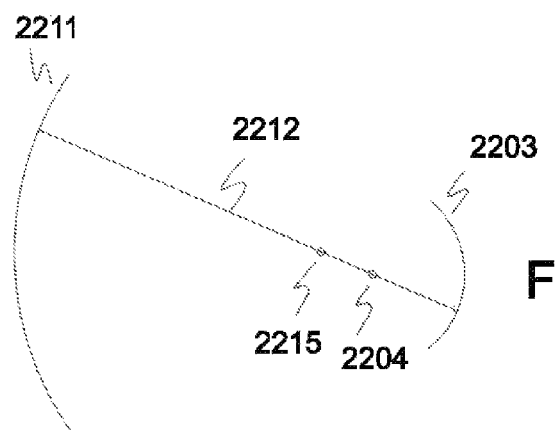
Figure 22C:
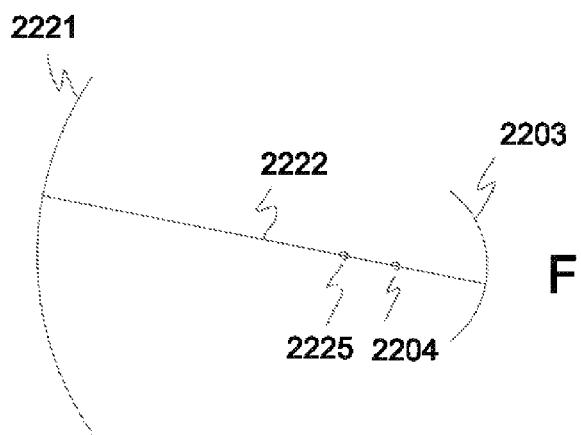

FIGS. 22A, 22B, and 22C is another schematic representation of representation of a second method for centrating an arc scanner, with the method also being illustrated on the posterior surface of a lens. In this method, the center of curvature of an arc guide track is not coincident with the center of curvature of an eye component of interest, such as the anterior or posterior surface of a cornea or lens. However, when centration is achieved in this method, an ultrasound pulse emitted by a transducer on the arc guide track always passes through both the center of curvature of the arc guide track and the center of curvature of an eye component of interest. This condition can be met by moving the entire arc guide track laterally as the transducer is moved along the arc guide track.

If the separation centers of curvatures in the z-direction is "$\Delta z$" then the movement of the arc guide track in the x-direction is:

$$\Delta x = \Delta z (\tan \alpha_1 - \tan \alpha_2)$$

where $\alpha_1$=the angle between the transducer axis and the horizontal at time $t_1$ and $\alpha_2$=the angle between the transducer axis and the horizontal at time $t_2$ If, as in FIGS. 22A, 22B, and 22C, the center of curvature of an arc guide track is further away from the surface of the eye component of interest than the center of curvature of an eye component of interest, then the entire arc guide track is moved laterally in the same general direction as the transducer is moved along the arc guide track as illustrated in FIG. 22A by arrow 2222 denoting the direction of movement of the arc guide track assembly and arrow 2221 denoting the direction of movement of the transducer.

FIG. 22A shows the arc path 2201 of a transducer face whose center of curvature 2205 is further away from the eye surface of interest 2203 than the center of curvature 2204 of an eye component of interest. As the transducer moves along its arc guide track, it sends out ultrasonic pulses such represented by ray 2202. These pulses pass through the center of curvature 2205 of the transducer arc path 2201 as well as the center of curvature 2204 of the eye component of interest.

FIG. 22B shows the arc path 2211 of a transducer face whose center of curvature 2215 is further away from the eye surface of interest 2203 than the center of curvature 2204 of an eye component of interest. As the transducer moves along its arc guide track, the entire arc guide track assembly moves in the same direction as described above. As the transducer moves along its arc guide track, it sends out ultrasonic pulses such represented by ray 2212. These pulses pass through the center of curvature 2215 of the transducer arc path 2211 as well as the center of curvature 2204 of the eye component of interest.

FIG. 22C shows the arc path 2221 of a transducer face whose center of curvature 2225 is further away from the eye surface of interest 2203 than the center of curvature 2204 of an eye component of interest. As the transducer moves along its arc guide track, the entire arc guide track assembly moves in the same direction as described above. As the transducer moves along its arc guide track, it sends out ultrasonic pulses such represented by ray 2222. These pulses pass through the center of curvature 2225 of the transducer arc track 2221 as well as the center of curvature 2204 of the eye component of interest.

The rays 2202, 2212 and 2222 are all of slightly differing lengths becoming shorter as the transducer moves along the arc guide track. However, the change in transit time of the transmitted and received ultrasonic pulses can be corrected by the known geometric relationships since the positions of the transducer on the arc guide track and the position of the arc guide track assembly are known accurately at all times. The key point here is that the rays 2202, 2212 and 2222 all reflect normally off the surface of the eye component of interest. In the case illustrated in FIGS. 22A, 22B, and 22C, the arc scanner is able to image the posterior surface of the lens even though the curvature of the posterior lens surface and the curvature of the arc guide track are of opposite sign.

As an example of the range of motions illustrated in FIGS. 22A, 22B, and 22C, the center of curvature of transducer face (R=20 mm) is about 3.363 mm further away from the eye component than the center of curvature of the posterior surface of the lens (R=6 mm).

| Transducer angle with respect to the horizontal (degrees) | Lateral displacement of arc track between adjacent angular movements (mm) |
| --- | --- |
| 35.000 | 0.000 |
| 23.045 | 0.9241 |
| 11.090 | 0.7714 |

Forming an Image of the Anterior Segment of an Eye

An ultrasound image of the anterior segment of an eye, which includes the cornea, the iris, the sclera, the lens, the ciliary body and the zonules may be imaged by a series of scans in the following way, using the scanning device described in FIGS. 7 through 11 where centration is achieved either by the method of FIGS. 21A, 21B, and 21C, or FIGS. 22A, 22B, and 22C. Such a scan can image substantial portions of both anterior and posterior cornea as well as substantial portions of the anterior and posterior lens surfaces.

1. the arc scanner is positioned with respect to the center of the eye by manual or computer-controlled means using the x-, y- and beta positioning means described in FIG. 7.
2. the focal plane of the transducer is placed at or near the posterior lens surface by observing and maximizing the amplitude of an A-scan pulse waveform known to be from the posterior lens surface substantially along the optical axis of the eye
3. A first linear scan is made with the transducer carriage parked at an angle α on the arc guide track (α is typically in the range of 10 to 35 degrees above the optical axis). A second linear scan is made with the transducer carriage parked at an angle −α on the arc guide track. These scans capture sections of the posterior surface of the lens capsule, these sections typically being off the optical axis.
4. the focal plane of the transducer is then retracted so that it is situated near the midpoint of the lens by observing the amplitude of an A-scan substantially along the optical axis of the eye.
5. A combined scan (co-ordinated linear and arcuate motion such as described in FIGS. 21A, 21B, and 21C, or FIGS. 22A, 22B, and 22C) is then implemented. This scan captures most of the anterior surface of the lens capsule as well as images of the zonules, ciliary body and iris.
6. the focal plane of the transducer is further retracted so that it is situated in the cornea again by observing the amplitude of an A-scan substantially along the optical axis of the eye.
7. An arc scan is then made which captures a sharp image of the cornea and its internal structure as well as additional images of the sclera, iris and anterior lens capsule surface. This scan will typically also image a short section of the posterior lens capsule near the optical axis.
8. Since the above scans are referenced by a common co-ordinate system, they can be readily combined to create a comprehensive image of substantially all of the anterior segment of the eye.
9. This same type of scan can be obtained for several sections (or meridians) through the eye by changing the meridian to be imaged using the beta (rotational) mechanism of the positioner (see FIG. 7).

A series of these anterior segment scans can be carried out by the scanning device described in FIGS. 8 through 11 in about 5 to about 10 seconds so that the patient has little opportunity to move his or her eye.

As can be appreciated, the steps described above can be performed in a number of different sequences from those described.

Lens Volume

Figure 23:
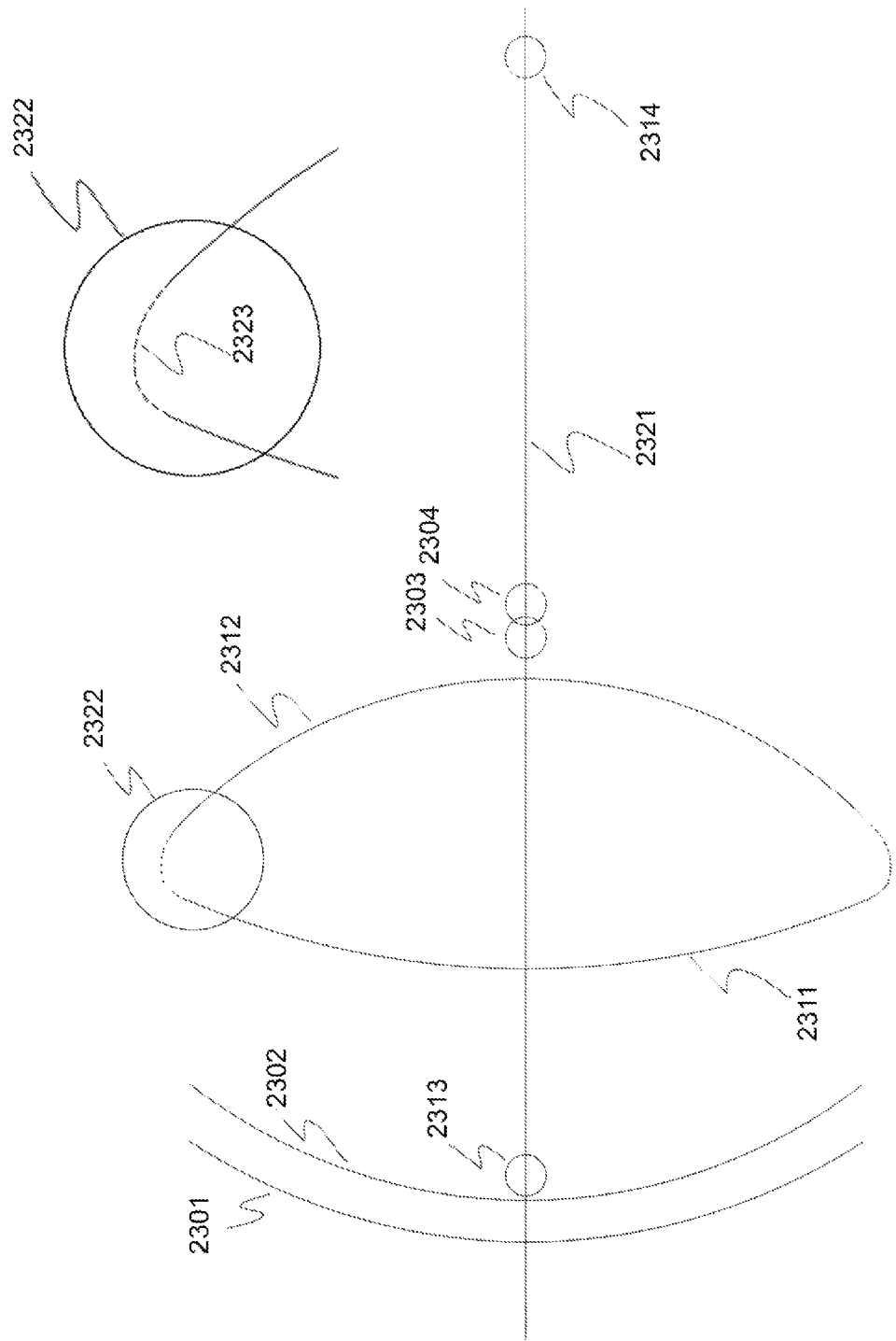
FIG. 23 illustrates a method for determining lens volume.

FIG. 23 illustrates a method for determining lens volume. FIG. 23 shows an anterior cornea surface 2301 and a posterior cornea surface 2302 and their respective centers of curvature 2303 and 2304. Also shown are an anterior lens surface 2311 and a posterior lens surface 2312 and their respective centers of curvature 2314 and 2313. The circle 2322 highlights a region where the anterior and posterior lens surfaces come together. The surfaces shown as dotted lines are typically not imaged well or not imaged at all in an ultrasonic scan and therefore have to be estimated. The region 2322 is shown magnified with the hard-to-image surfaces 2323 shown again by dotted lines. As can be appreciated the extent of these hard-to-image surfaces shown is only approximate and depends on the particular patient and on the capabilities of the ultrasonic arc scanner. A possible method for imaging this region of the lens is described in U.S. patent application Ser. No. 12/475,322.

These hard-to-image surfaces 2323 where the anterior and posterior surfaces of the lens come together can be estimated in at least the following ways:
(1) an estimate of the shape of the hard-to-image surfaces can be made by a qualified ophthalmologist and this shape can be scaled so that it blends with the imaged surfaces of the anterior and posterior lens surfaces.
(2) acoustic images of the region where the anterior and posterior lens surfaces come together can be made using advanced methods such as described below. These can be combined with other B-scans of the anterior and posterior surfaces of the lens.
(3) plots of anterior and posterior surface angles can be used to estimate the approximate location of the hard-to-image surfaces where the anterior and posterior lens surfaces come together The volume of the lens capsule can be determined for example by taking a number of B-scans at different meridian angles and using these to collect a number of points on the anterior and posterior lens surface to form a 3-D representation of the lens. Once a wire frame surface grid is constructed, other points on the lens surface can be approximated by any number of well-known multi-dimensional interpolation methods. The co-ordinates can be used to compute the volume of the lens, for example, if the lens is not a perfect ellipsoid.

Alternate Transducer Configuration

Figure 24:
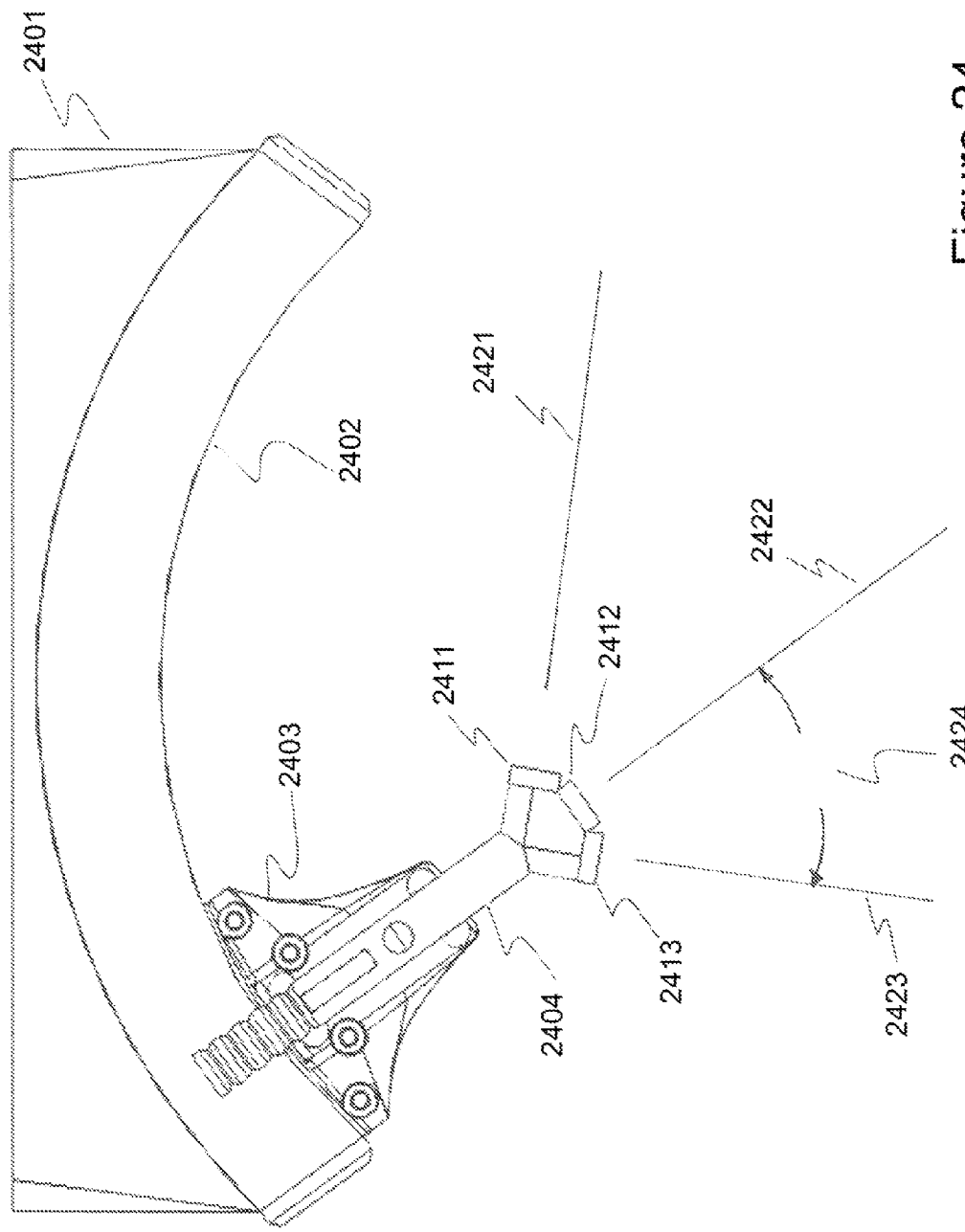
FIG. 24 is a schematic of a transducer configuration for improving the range of imaging of an ultrasonic arc scanner.

FIG. 24 is a schematic of a transducer configuration for improving the angular range of imaging of an ultrasonic arc scanner. An arc scanner typically has a maximum included angle through which its transducer moves along its arc guide track. The included angle is typically in the range of about 60 degrees to about 80 degrees. Depending on where the center of curvature of the arc guide track is positioned, the lateral width of an eye component of interest that the scanner can image, may be limited, for example by the eyelid. The transducer configuration illustrated in FIG. 24 will help to extend the lateral range of the image. FIG. 24 shows an arc guide track assembly 2401 on which a transducer carriage 2403 is mounted. The transducer carriage 2403 moves along an arc guide track 2402 during a scan while, as described in FIGS. 21A, 21B, and 21C, and FIGS. 22A, 22B, and 22C, the arc guide track assembly may also be moved linearly during a "combined" scan. FIG. 24 illustrates three transducers 2411, 2412 and 2413 mounted on a single transducer shaft 2404. There can be more than three transducers but typically at least one of the transducers 2412 will have its axis aligned with the axis of the transducer shaft 2404 which in turn is preferably aligned along a radius of curvature of the arc guide track 2402. The included angle 2424 between adjacent transducers is typically in the range of about 1 degree to about 15 degrees. The center transducer 2412 will typically be used to image a specular surface of interest, such as a cornea or lens surface, while the outside transducers 2411 and 2413 will typically be used to image non-specular components of interest such as the sclera, iris, zonules etcetera. The outside transducers 2411 and 2413 can also provide partial or substantially complete images of the lens surfaces in the region where the anterior and posterior surfaces come together. The pulses emitted and reflected signals received by each transducer may be separate or co-ordinated. Since the exact timing of emitted pulses and the exact location of each transducer is always known, the reflected signals received by each transducer may be reconstructed into a comprehensive image by post-processing or real time processing.

Control and Signal Processing

Figure 25:
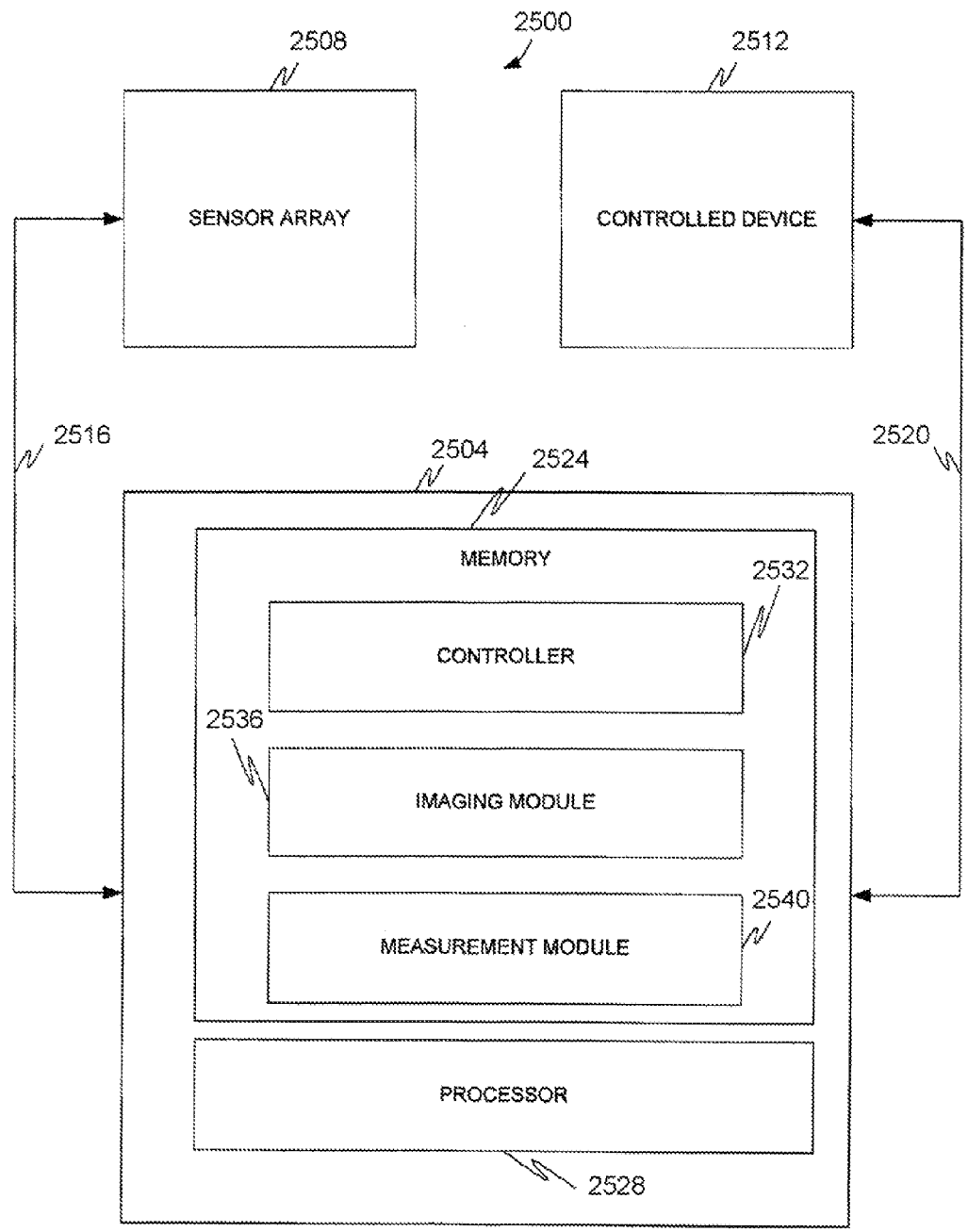
FIG. 25 is a block diagram of a control architecture for an ultrasound imaging device.

FIG. 25 depicts a control and signal processing system for any of the ultrasound imaging device configurations discussed above. The system 2500 includes a sensor array 2508 and controlled device 2512 in signal communication, via duplexed channels 2516 and 2520, with a computer 2504.

The sensor array 2508 includes a host of linear or angular position sensors that, inter alia, track the relative and/or absolute positions of the various movable components, such as the positioning mechanism 602, arc guide track 601 and transducer carriage 603, rotatable transducer head 605, transducer or arc scanner head 605 and 709, scanner head mount arm 710, axial piston 703, piston 704, piston 705, linear carriage 802, arc carriage 803, a motor to move the arc carriage 803 along the track 805 (not shown), and linear drive motor in the linear drive motor housing 807. The sensor array can include any suitable type of positional sensors, including inductive non-contact position sensors, string potentiometers, linear variable differential transformers, potentiometers, capacitive transducers, eddy-current sensors, Hall effect sensors, proximity sensors (optical), grating sensors, optical encoders (rotary or linear), and photodiode arrays. Preferred sensor types are discussed in U.S. patent application Ser. No. 12/347,674, which is incorporated herein by this reference.

The controlled device 2512 is any device having an operation or feature controlled by the computer 2504. Controlled devices include the various movable or activatable components, such as the positioning mechanism 602, arc guide track 601 and transducer carriage 603, rotatable transducer head 605, transducer or arc scanner head 605 and 709, scanner head mount arm 710, axial piston 703, piston 704, piston 705, linear carriage 802, arc carriage 803, motor to move the arc carriage 803 along the track 805 (not shown), and linear drive motor in the linear drive motor housing 807.

The computer 2504 is preferably a software-controlled device that includes, in memory 2524, a number of modules executable by the processor 2528. The executable modules include the controller 2532 to receive and process positioning signals from the sensor array 2508 and generate and transmit appropriate commands to the monitored controlled device 2512, imaging module 2536 to receive and process A- and B-scan images to produce two-, three- or four dimensional images of selected ocular components or features, and measurement module 2540 to determine, as discussed above, the dimensions and/or volumes of selected ocular components and/or features. The imaging algorithm used by the imaging module 2536 is further discussed in U.S. patent application Ser. No. 12/418,392, which is incorporated herein by this reference.

A Third Method for Centrating

Figure 26:
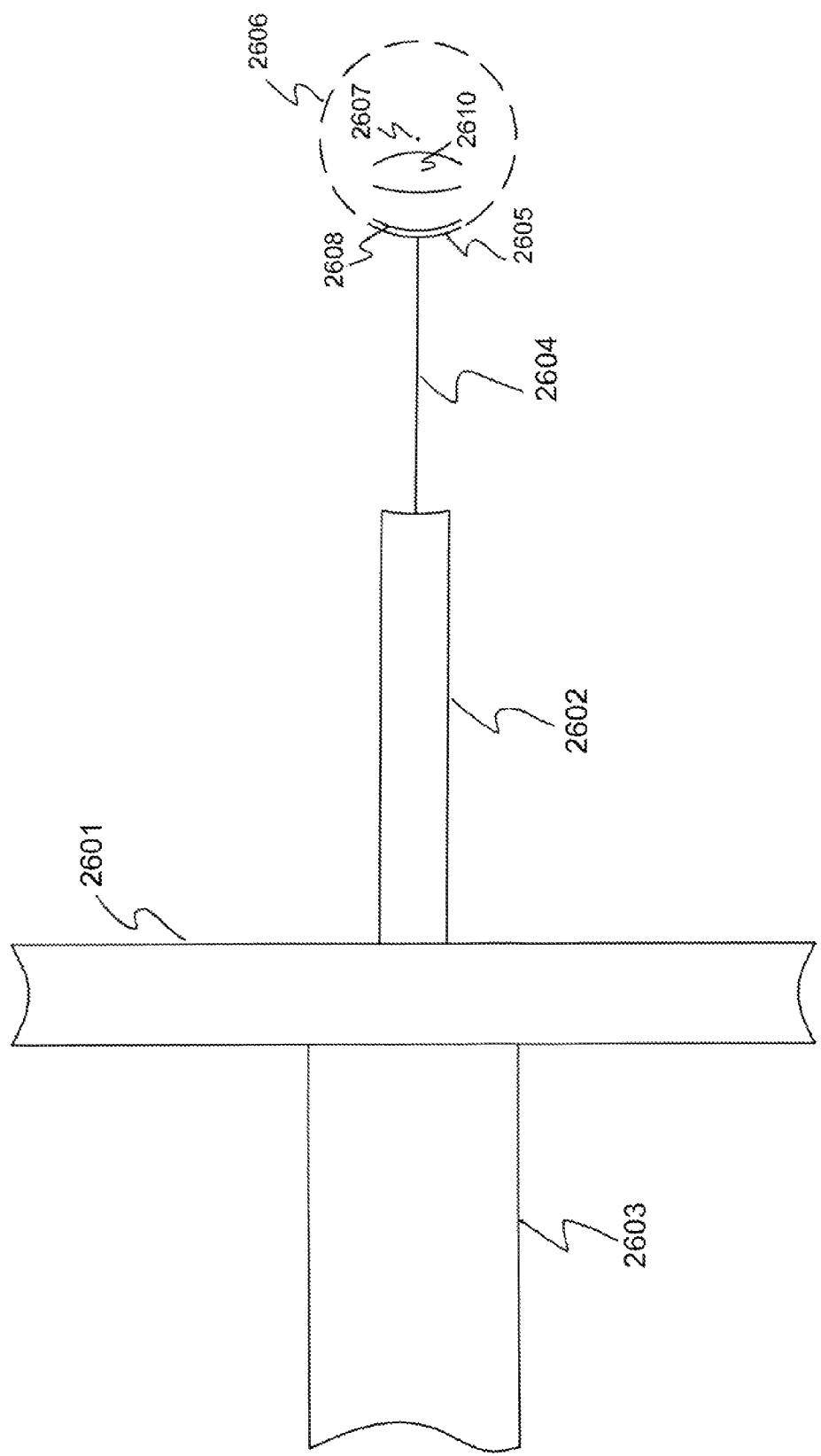
FIG. 26 is a schematic representation of a third method for centrating an arc scanner on a surface of a cornea.

FIG. 26 is a schematic representation of a third method for centrating an ultrasound scanner on a curved area of interest of an eye, such as, for example, the anterior surface of the cornea 2605. The posterior surface of the cornea 2608 is shown for reference. In this method, a transducer 2602 travels along a track 2601. Track 2601 may be a linear or curved track, or any combination thereof. The transducer is positioned in the general area of the area of interest of the eye by another means, such as, for example, visually by an operator. As the transducer 2602 travels along the track, ultrasound pulses represented by ray 2604 are emitted at known transducer positions along the track. As can be appreciated, the length of the pulse path for each ray 2604 can be plotted obtain a geometrically accurate representation of the anterior surface of the cornea 2605, using known A-scan or B-scan methods. A curve, arc, circle, or ellipse, or other shape 2606 can be fitted to the area of interest of the eye, and the location of the apex and centroid of center of curvature 2607 of curve, arc, circle, or ellipse, or other shape 2606 can be calculated. The process of fitting a curve, arc, circle, or ellipse, or other shape to the area of interest of the eye may be performed using computer techniques, any of which may not require generating an actual geometrically correct plot. Since the position of transducer 2602 is accurately recorded for each ray 2604, track 2601 can subsequently be moved laterally by positioner 2603 to align the axis of transducer 2602 with the line joining the apex and centroid of the curve, arc, circle, or ellipse, or other shape fitted to the area of interest of the eye 2607. This substantially achieves lateral centration. Further, track 2601 can be moved axially (along its z-axis) by positioner 2603 to, for example, place the focal plane of transducer 2602 on the anterior surface of the cornea 2605 to substantially achieve axial centration.

This method can be repeated at one or more meridional positions to centrate the scanner within the x-y plane.

Methods for Determining Thickness and Sound Speed of a Selected Region of the Eye In the following, the lens is used as an example of a selected region of the eye to illustrate a method for determining thickness and sound speed of a selected region. The same method may be applied to the cornea, aqueous humor and vitreous humor, any artificial lens and the like, all of which are bounded by acoustically reflective interfaces.

Typically, the thickness of a lens, measured approximately along its optical axis utilizing an ultrasound technique, can be estimated by either of two known methods:

(1) by measuring the thickness of the lens directly from an ultrasound B-scan image. The B-scan is constructed from by measuring reflected pulse time of arrivals of many pulses and converting these to distances by using accepted acoustic velocities in water, the cornea, the lens, the vitreous and aqueous humors as described, for example, in "Ultrasonography of the Eye and Orbit", Second Edition, Coleman et al, published by Lippincott Williams & Wilkins, 2006.

(2) by measuring the thickness of the lens using an A-scan by setting the ultrasonic transducer with its focal plane inside the lens, preferably near the center, with the transducer axis substantially aligned with the optical axis of the lens, then measuring the time difference between the reflected pulse peak from the posterior surface of the lens and the reflected pulse peak from the anterior surface of the lens. This time difference $\Delta t$ can be converted to the desired on-axis lens thickness by the formula:

$$\Delta z = \Delta t / 2c$$

where $\Delta t$=measured time difference between the pulses reflected off the anterior and posterior surface $\Delta z$ is the on-axis lens thickness and c=the accepted lens acoustic velocity The factor of 2 arises as the reflected pulse from the posterior surface travels twice the distance across the lens. The pulse transit time across a region is therefore ½ the measured time between the pulses reflected from the anterior and posterior surfaces of the region.

Both of these methods, which are known, rely on the use either implicitly or explicitly on the accepted acoustic velocity used for the lens to create the B-scan or to convert the pulse transit time difference of an A-scan to a distance measurement. Also both of these methods rely on an image of at least the posterior pole region of the lens capsule which can usually, but not always, be obtained by a simple arc scanner (arcuate guide track only) with its transducer substantially aligned with the optical axis.

An independent measurement of the lens thickness may be obtained, for example, from a high quality nuclear magnetic resonance scan ("MRI") of the eye and an accurate measurement taken from the MRI image. This can be compared to the lens thickness determined from either of the two methods described above. Yet another independent measurement of the lens thickness may also be obtained, for example, from a high quality optical image of the eye taken along the optical axis of the eye. This can be compared to the lens thickness determined from either of the two methods described above. Both of these independent methods require corrections which may lead to errors and these measurements would have to be accurate to within about 10 to about 20 microns to be useful.

A method for determining the thickness of a lens along any line through the lens including the on-axis line (visual or optical on-axis line) is to utilize A-scans and the z-axis positioner. The scanner is positioned so that the transducer can emit pulses along a line through a substantial section of a region of interest such, as for example, the lens of an eye. With the scan head fixed, the positioner is moved back and forth along the z-direction until the anterior surface of the lens is identified and its reflected A-scan signal amplitude is maximized. This corresponds to the focal plane of the transducer being placed on the anterior surface of the lens. The z-axis position of the positioner, z1, is recorded. Next, the positioner is moved back and forth along the z-direction until the posterior surface of the lens is identified and its reflected A-scan signal amplitude is maximized. This corresponds to the focal plane of the transducer being placed on the posterior surface of the lens. The z-axis position of the positioner, z2, is then recorded. The difference is $|z1-z2|=\Delta z$, where $\Delta z$ is a direct measurement of the lens thickness. In this method, the transducer holder is aligned with the z-axis of the positioner so that the face of the transducer always moves perpendicularly to the z-axis when the positioner is moved along its z-axis.

The following figures describe, in more detail, a method for determining the thickness of a selected region of the eye and for determining an accurate measure of average sound speed in the selected region.

Figures 27A, 27B:
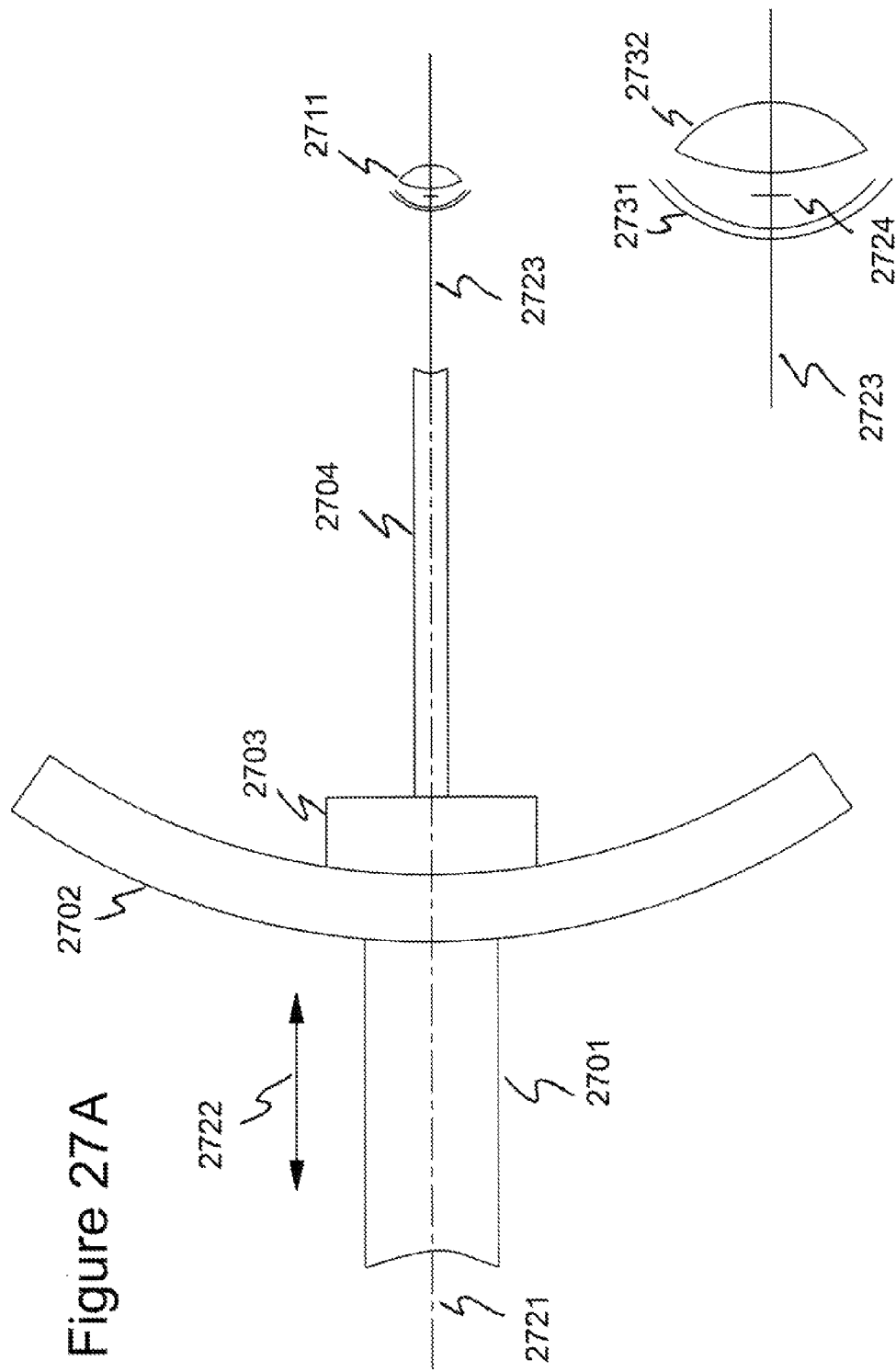
FIGS. 27A and 27B illustrate the position of the apparatus to measure thickness and sound speed of a selected region of the eye.

FIGS. 27A and 27B illustrate the position of an apparatus that can measure thickness and sound speed of a selected region of the eye. FIG. 27A shows a positioner arm 2701 rigidly attached to a arcuate guide track 2702. A transducer carriage 2703 is shown centered on the arcuate guide track 2702. An ultrasound transducer holder 2704 is rigidly attached to transducer carrier 2703 such that the transducer element emits an ultrasound pulse along a path 2723 that is aligned with the axis of transducer holder 2704 along the z-axis 2721 of the positioner arm 2701. In this example, the path 2723 of the ultrasound pulse is shown entering an eye 2711 substantially along its visual or optical axis. As will be noted below, the path 2723 of the ultrasound pulse may be at an angle to the visual or optical axis as long as it intersects the two interfaces of the selected region for purposes of determining sound speed of the region. However, it is always preferable to make measurements where the sound pulse is normal to the interfaces so as to minimize refractive errors.

FIG. 27B shows a close up of the eye illustrating the path 2723 of the ultrasound pulse through the cornea 2731 and the lens 2732. In this example, the focal plane 2724 of the ultrasound transducer is shown located in the aqueous humor between the cornea 2731 and the lens 2732. As the positioner arm 2701 is moved back and forth 2722 along its z-axis 2721, the focal plane 2124 of the transducer moves along the z-axis such that it can cross the two interfaces bounding the region of interest in the eye. As described in FIGS. 28A, 28B, 28C, 28D, and 28E, the two example interfaces are the anterior and posterior surfaces of a lens.

Figure 28A:
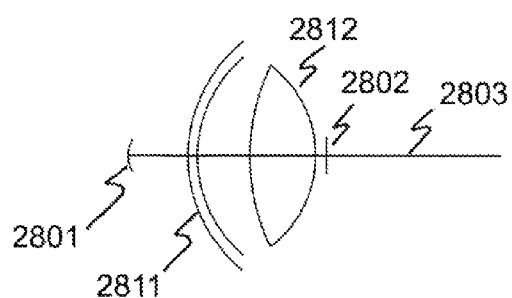
FIGS. 28A, 28B, 28C, 28D, and 28E illustrate the movement of the transducer focal plane to measure thickness and sound speed of a selected region of the eye.
Figure 28B:
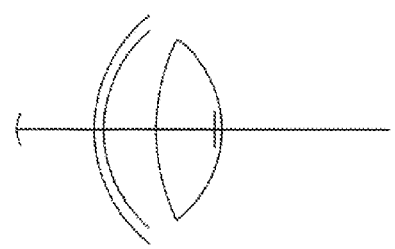
Figure 28C:
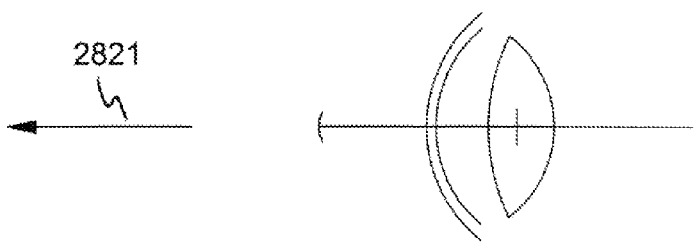
Figure 28D:
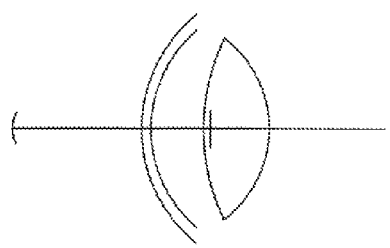
Figure 28E:
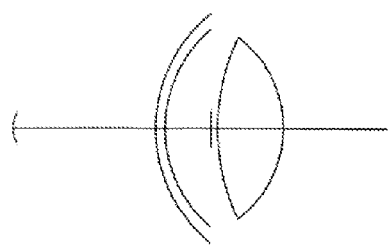

FIGS. 28A, 28B, 28C, 28D, and 28E illustrate the movement of the transducer focal plane to measure thickness and sound speed of a selected region of the eye (a lens in this example). FIG. 28A shows a cornea 2811 and a lens 2812 of an eye with an ultrasound pulse path 2803 passing through the eye. The face 2801 of an ultrasound transducer is shown in relation to the focal plane 2802 of the transducer. The transducer is set up as described in FIGS. 27A and 27B such that the ultrasound pulse path 2803 is aligned to be coincident with the z-axis of the positioner arm. FIG. 28A shows the focal plane 2802 of the transducer behind the posterior surface of lens 2812 in the vitreous humor. In FIG. 28B, the positioner arm has been retracted along its z-axis, moving the focal plane of the transducer into the lens just inside the posterior surface of the lens so that the focal plane has passed across the posterior interface of the lens. As the focal plane is moved, the transducer is emitting a series of ultrasound pulses producing an A-scan with each pulse. In FIG. 28C, the positioner arm has been further retracted along its z-axis, moving the focal plane of the transducer into the center of the lens while continuing to emit a series of ultrasound pulses. In FIG. 28D, the positioner arm has been further refracted along its z-axis, moving the focal plane of the transducer up to the anterior surface of the lens while continuing to emit a series of ultrasound pulses. In FIG. 28E, the positioner arm has been further retracted along its z-axis, moving the focal plane of the transducer past the anterior interface of the lens into the aqueous humor region so that the focal plane has passed across the anterior interface of the lens while continuing to emit a series of ultrasound pulses. The transducer has now generated a series of A-scans as the focal plane 2802 traverses both surfaces of the lens which is the selected region in this example. At the same time, the position of the transducer along the z-axis has been recorded, for example by a magnetic encoding strip on the positioner arm, so that the position of the transducer focal plane is known for each A-scan.

As can be appreciated, the series of A-scans can be generated as described above by moving the transducer in either direction through the selected region. If the positioner arm has significant back lash when its motion is reversed, then it is preferable to move the positioner arm continuously in either one direction or the other to obtain the most accurate measurements.

Figure 29A:
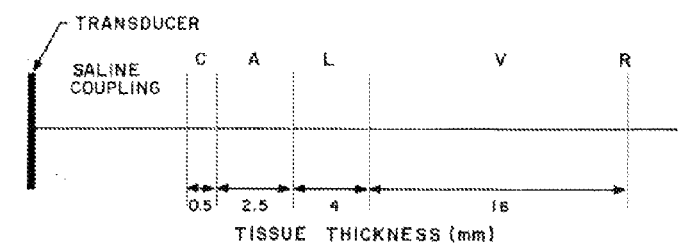
FIGS. 29A, 29B, 29C, and 29D illustrate an actual ultrasound A-scan.
Figure 29B:
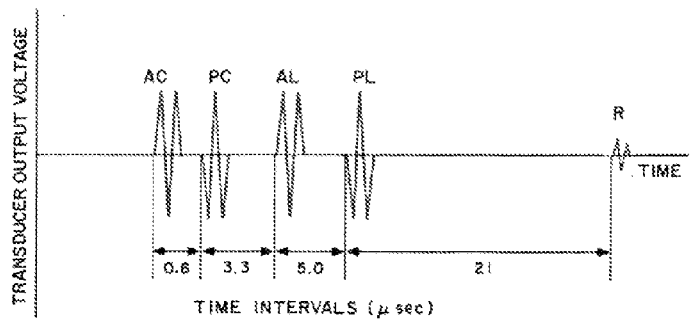
Figure 29C:
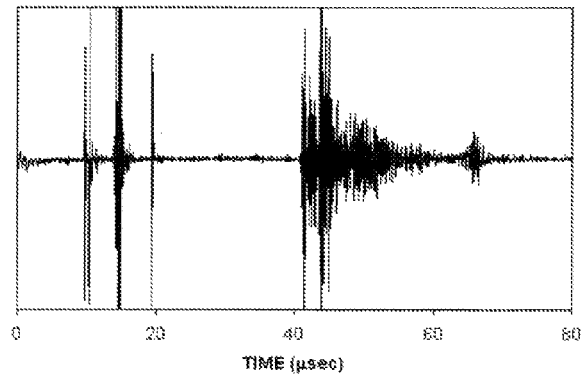
Figure 29D:
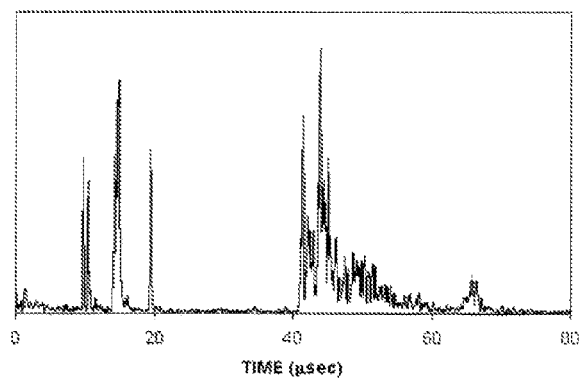

FIGS. 29A, 29B, 29C, and 29D illustrate an clinical ultrasound A-scan. This figure was taken from FIGS. 1.8 and 1.9 of "Ultrasonography of the Eye and Orbit", Second Edition, Coleman et al, published by Lippincott Williams & Wilkins, 2006 and illustrates how an A-scan is generated and interpreted. FIG. 29A is a schematic representation of the main interfaces in an eye that generate strong reflected ultrasound signals. Shown are the surfaces bounding regions of the cornea (C), the aqueous humor (A), the lens (L) the vitreous humor (V) and finally the retina (R). FIG. 29B shows the corresponding reflected A-scan signals from the anterior surface of the cornea (AC), posterior surface of the cornea (PC), the anterior surface of the lens (AL), posterior surface of the lens (PL) and the retina (R). FIG. 29C shows a typical RF ultrasound signal (voltage versus time) where the leftmost signals correspond to reflections from the membrane separating the fluid in the eyepiece from the fluid in the scanner. FIG. 29C shows reflections from the membrane, the corneal and lens surfaces but does not show the reflection from the retina. FIG. 29D shows the rectified A-scan signal of FIG. 29C. Many rectified and filtered A-scans are used to modulate a grayscale that is commonly used to generate a B-scan.

Figure 30:
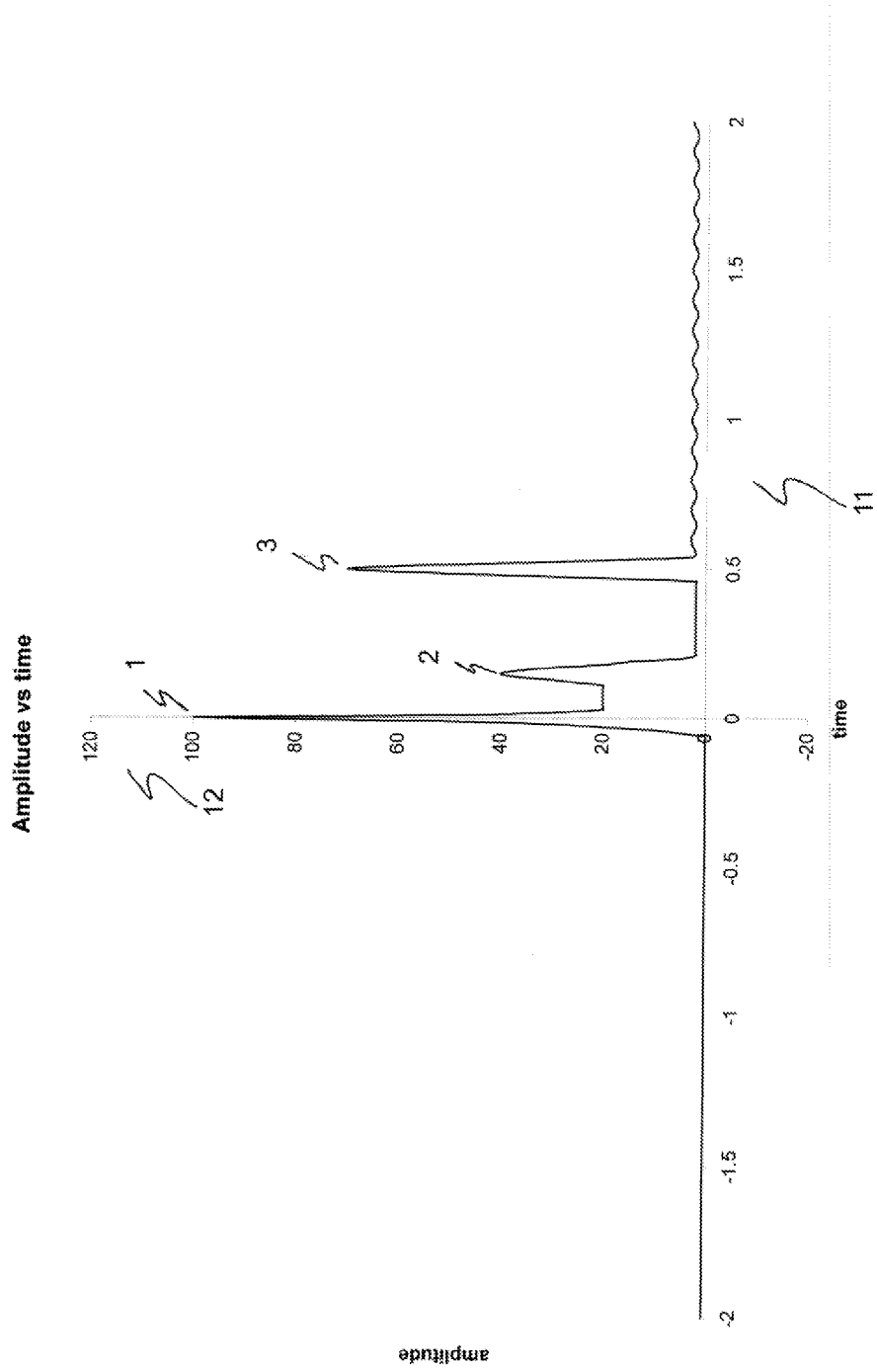
FIG. 30 is a schematic of an A-scan of the cornea of an eye.

FIG. 30 is a schematic representation of an A-scan of a cornea of an eye. This illustration shows a typical rectified signal through the cornea as amplitude 12 versus time 11. Local maximum 1 represents the anterior surface of the cornea, local maximum 2 represents Bowman's layer within the cornea and local maximum 3 represents the posterior surface of the cornea.

Figure 31:
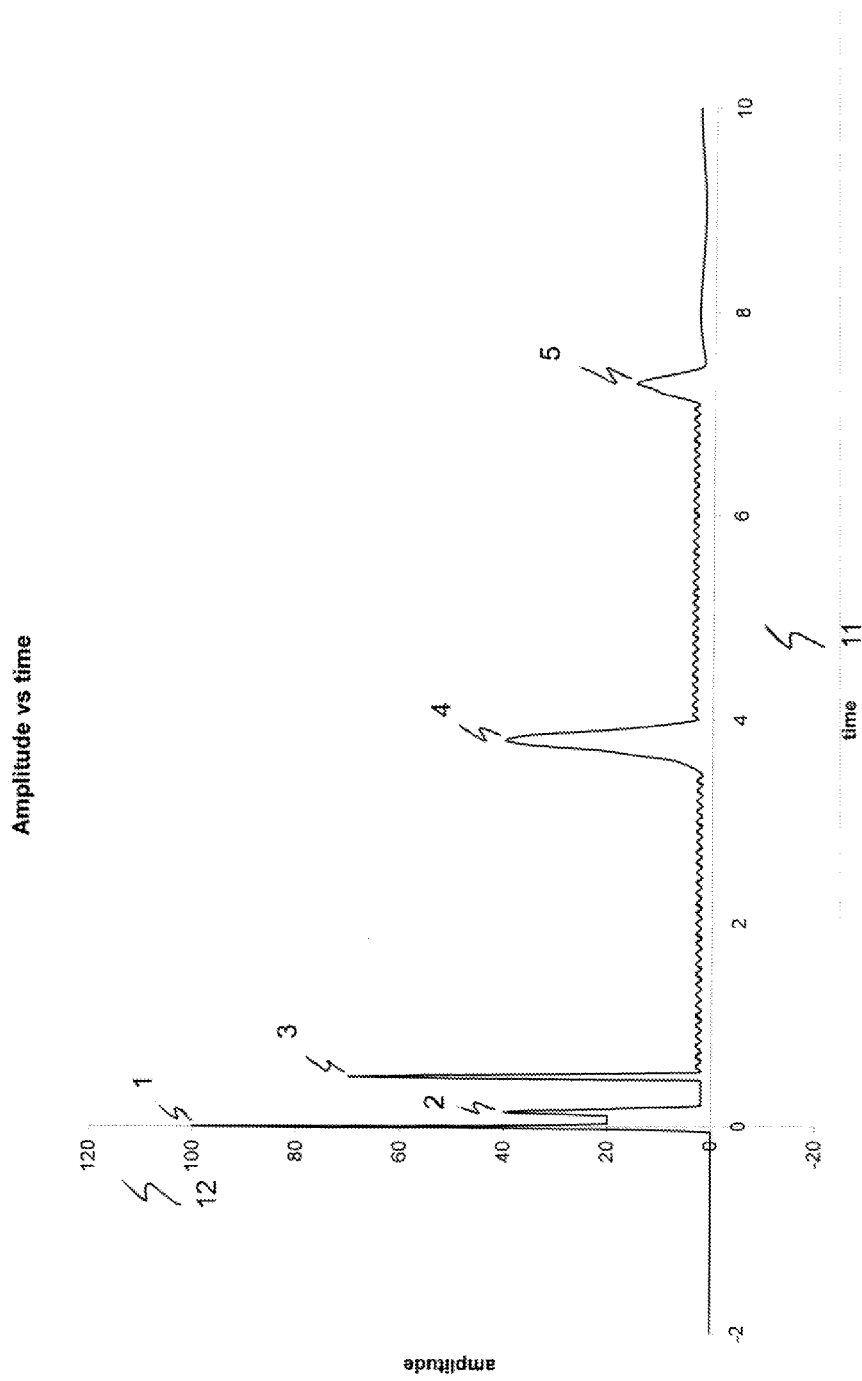
FIG. 31 is a schematic of an A-scan of the anterior segment of an eye.

FIG. 31 is a schematic of an A-scan of the anterior segment of an eye. This illustration shows a typical rectified and filtered signal through the anterior segment as amplitude 12 versus time 11. Local maximum 1 represents the anterior surface of the cornea, local maximum 2 represents Bowman's layer, local maximum 3 represents the posterior surface of the cornea, local maximum 4 represents the anterior surface of the lens and local maximum 5 represents the posterior surface of the lens.

Figure 32:
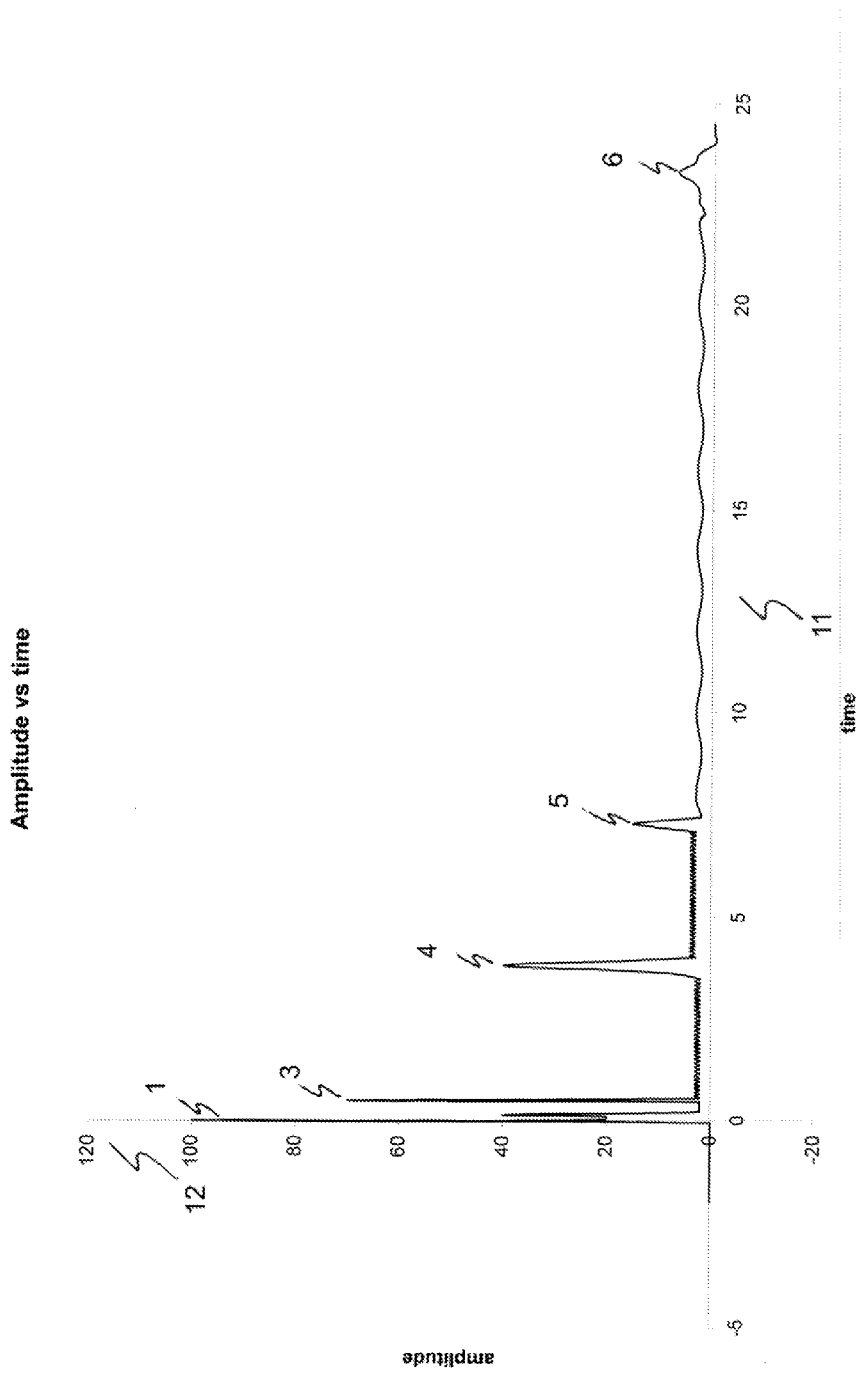
FIG. 32 is a schematic of an A-scan of an eye from cornea to retina.

FIG. 32 is a schematic of an A-scan of an eye from cornea to retina. This illustration shows a typical rectified and filtered signal through the entire interior of an eye as amplitude 12 versus time 11. Local maximum 1 represents the anterior surface of the cornea, local maximum 3 represents the posterior surface of the cornea, local maximum 4 represents the anterior surface of the lens, local maximum 5 represents the posterior surface of the lens and local maximum 6 represents the surface of the retina. The reflected pulses are shown decreasing in amplitude for interfaces deeper within the eye. This is because the further an acoustic pulse travels, the greater the amplitude attenuation in the acoustic medium. Unless dynamic focusing techniques are used, the reflected signal strength also decreases rapidly as the distance between the interface and transducer focal plane increases.

Figure 33:
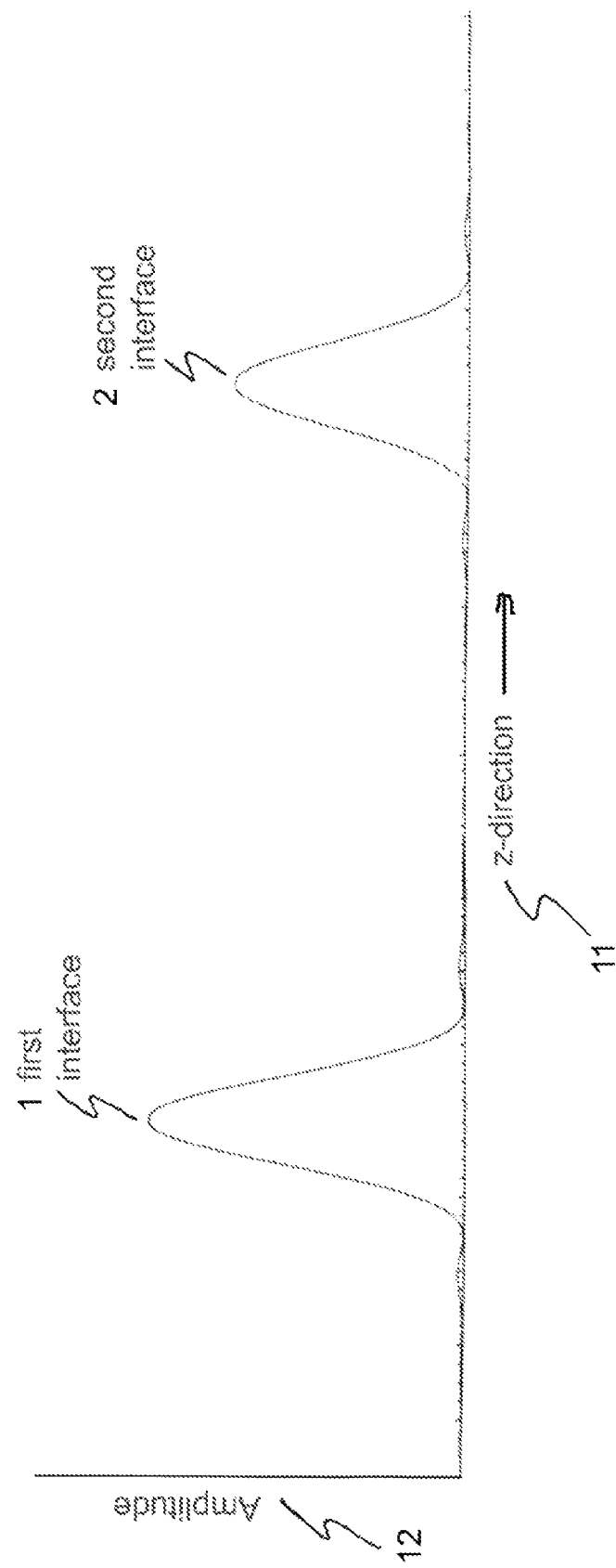
FIG. 33 is a schematic of A-scan amplitudes versus distance along a z-axis of a positioner.

FIG. 33 is a schematic of a series of A-scan maximum amplitudes 12 plotted versus distance 11 along a z-axis of a positioner. In this graph, the ultrasound transducer holder axis is accurately aligned with the z-axis of the positioner so that the face of the transducer element always moves perpendicularly to the z-axis when the positioner is moved along its z-axis. As the focal point of the transducer approaches an interface, the maximum signal amplitude increases to a maximum value and then decreases as the focal plane of the transducer passes across the interface. In the example of FIG. 33, the transducer is moved from an initial position where its focal plane is in front of the anterior surface of the region of interest and is moved until it is beyond the posterior interface of the region of interest. Thus there are two local maximum values 1 and 2 that correspond to interfaces generated by this procedure. The local maximum values are particularly strong when the interfaces are specular. Since the z-position of the positioner is recorded, the difference in z-positions between the first local maximum value 1 and the second local maximum value 2 is a mechanical measurement of the distance between the two interfaces and has the precision of the positioner locator method. For example, if a commercially available magnetic encoder strip is used, the z-position can currently be measured to an accuracy of about 1 micron.

As can be appreciated, any or all of the A-scans used in the above procedure may be used to measure the time difference between the two interfaces of the region of interest. If many or all A-scans are used, they can be averaged to obtain an even more accurate measurement. If a commercially available 200 MHz A/D converter is used to digitally record each A-Scan, then a time difference between the two interfaces can currently be measured to an accuracy of about 5 nanoseconds.

Using the above accuracies for distance and time measurements, average sound speed can be measured with an error of no more than about:

30 m/s in the cornea
5 m/s in the aqueous humor and lens
1 m/s in the vitreous humor The large error in the cornea is because the width of the cornea is so small, being typically about 0.5 mm.

Once the distance, $\Delta z$, between two interfaces of the region of interest is determined by the mechanical displacement of the z-axis positioner and the time interval, $\Delta t$, between two interfaces of the region of interest is determined from A-scans, then the average speed of sound, c, of the region of interest can be determined as $c = 2 \Delta z/\Delta t$ where $\Delta t$ is the measured time difference between the pulses reflected off the anterior and posterior surface of the region of interest.

Figure 34:
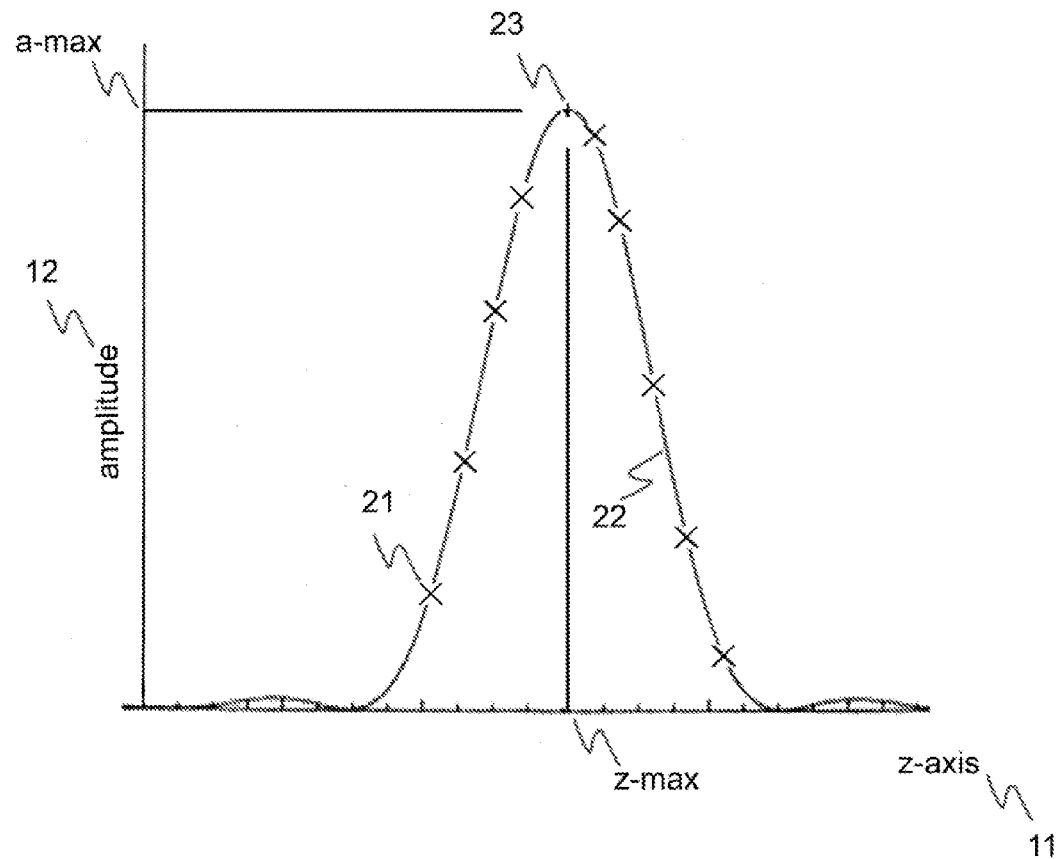
FIG. 34 is a schematic of A-scan amplitudes versus distance along a z-axis of a positioner showing a local maximum.

FIG. 34 is a schematic of A-scan amplitudes 12 versus distance 11 along a z-axis of a positioner showing a local maximum. As the focal point of the transducer approaches an interface, the maximum signal amplitude increases to a maximum value and then decreases as the focal plane of the transducer passes across the interface. Since the measurement is typically made digitally by an A/D converter, the maximum value of any A-scan may not be taken when the focal plane of the ultrasound transducer is exactly at the interface. A more accurate location and amplitude may be computed by fitting the digitally acquired data points 21 with an analytical curve 22. The analytic curve might be any appropriate function such as, for example, an n-term polynomial determined by a least squares fit to the digital data in the vicinity of the local maximum value, where n is an integer between about 4 and about 20.

If 'a' is the amplitude of the analytic function that is curve fit and 'z' is the distance along the z-axis, then the curve fit is of the form:

$$a = f(z)$$

when the derivative of the function $f'(z) = 0$, then a=a-max and z=z-max. Then a-max and z-max so obtained can be used as a more accurate representation of the local maximum value and z-max can be used as a more accurate value for the location of the interface.

Figure 35A:
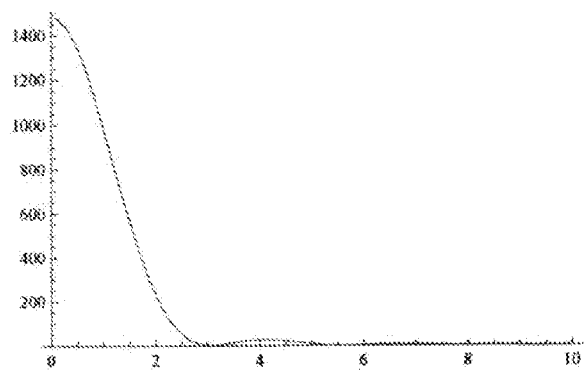
FIGS. 35A, 35B, and 35C illustrate the form of amplitude versus position of a focused ultrasound transducer.
Figure 35B:
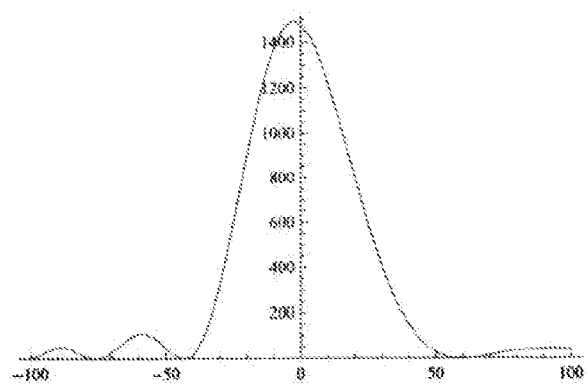
Figure 35C:
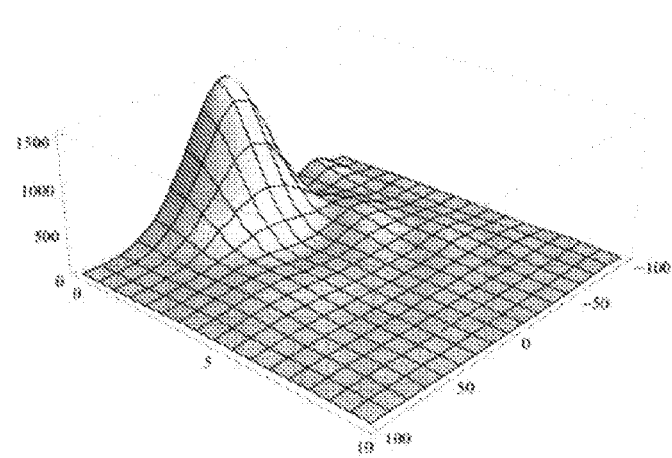

FIGS. 35A, 35B, and 35C illustrates the form of amplitude versus position of a focused ultrasound transducer. FIG. 35A shows the reflected signal amplitude in the axial half-plane (along the signal path). FIG. 35B shows the reflected signal amplitude in the lateral half-plane (perpendicular to the signal path). FIG. 35C shows a net plot of the signal amplitude for the region of the focal plane of the transducer. As can be seen, the amplitude will be at its highest in the focal region of the transducer. An annular array transducer can be used to move the focal plane of transducer to different regions of the eye and therefore can, with a single transducer, deliver high signal-to-noise reflected signals for selected regions throughout the eye.

The method disclosed above is described in more detail as follows:

1. Select a region (for example, cornea, lens, aqueous humor, vitreous humor) defined by at least two interfaces having acoustically reflective interfaces. The interfaces are preferably specular surfaces such as the anterior and posterior surfaces of the cornea and lens However, the interfaces may be non-specular but acoustically reflective interfaces such as for example the surface of the retina or sclera. The anterior interface is the first interface and the posterior interface is the second interface. Interfaces may be referred from time to time as surfaces.

2. Accurately align the transducer holder with the z-axis of the positioner so that the face of the transducer always moves perpendicularly to the z-axis when the positioner is moved along its z-axis.

3. Select any path thru the region for which the speed of sound is to be measured. A path substantially intersecting the interfaces perpendicularly is preferred. Any other path long enough to get an accurate measurement between the first and second interfaces of the selected region may be used but such a path may give rise to small refractive errors.

4. Position the ultrasound transducer as far back on z-axis as possible or at least with focal plane in front of the first interface; or position the transducer as far forward on z-axis as possible or at least with focal plane behind the second interface. In either case, the focal plane of the transducer should be able to traverse both interfaces defining the selected region during the taking of the measurement.

5. a. Move the transducer assembly along the z-axis with z-axis positioner taking a plurality of A-scans along a path crossing both anterior and posterior interfaces of the selected region.

b. If moving from anterior to posterior, when near the first interface, move the transducer assembly so as to determine a local maximum value of the A-scan amplitude in the vicinity of the first interface. This gives z1 as determined by the positioner location along the z-axis. When near the second interface, move the transducer assembly so as to determine a local maximum value of the A-scan amplitude in the vicinity of the second interface. This gives z2 as determined by the positioner location along the z-axis. FIG. 32 illustrates the maximum amplitudes from a plurality of A-scans as a function of distance along the z-axis.

c. If moving from posterior to anterior, when near the second interface, move the transducer assembly so as to determine a local maximum value of the A-scan amplitude in the vicinity of the second interface. This gives z2 as determined by the positioner location along the z-axis. When near the first interface, move the transducer assembly so as to determine a local maximum value of the A-scan amplitude in the vicinity of the first interface. This gives z1 as determined by the positioner location along the z-axis.

d. In making a series of A-scans for this procedure, it is preferable to determine z1 and z2 by moving the positioner in one direction along the z-axis so as to avoid mechanical backlash in the z-positioner.

6. Optionally, fit an analytic curve (preferably by the least squares method) to the A-scan data acquired in Step 5 to get a more accurate local maximum value, z1 max and z2 max, for z1 and z2. The more accurate value is determined by calculating the local maximum value of the function used for the curve fit. If a=amplitude and z=distance along the z-axis, then a curve fit is of the form:

$$a1 = f(z1)$$

when $f'(z1) = 0$, then a1=a1 max and z1=z1 max
similarly $$a2 = f(z2)$$

when $f'(z2) = 0$, then a2=a2 max and z2=z2 max

7. $\Delta z = \text{abs}(z1-z2)$ and $\Delta t = \text{abs}(t1-t2)$

8. Use any or all A-scans taken during the measurement to get t1 and t2 where t1 is the time of the maximum value of the first interface on each A-scan and t2 is the time of the maximum value of the second interface on each A-scan. FIG. 31 illustrates an A-scan showing amplitude of reflected signal as a function of time and illustrating peaks corresponding to a first and second interface (for example peaks 4 and 5 are the anterior and posterior interfaces of lens).

9. The speed of sound in the selected region is: c=2 Δz/Δt where Δt is the measured time difference between the pulses reflected off the anterior and posterior surface. The factor of 2 arises as the reflected pulse from the posterior surface travels twice the distance across the lens. The pulse transit time across a region is therefore ½ the measured time between the pulses reflected from the anterior and posterior surfaces of the region.

10. Repeat 1 thru 9 to eliminate unintended eye motion

A number of variations and modifications of the inventions can be used. For example, a linear scan can be made wherein the transducer carriage is set at a desired angular position along the arc guide track and then the entire arc guide track assembly is moved laterally. This process can be repeated with the transducer carriage set at a different desired angular positions along the arc guide track. This method can generate, for example, detailed images of non-specular features of interest such as such as: the angle between the cornea and iris lying behind the sclera; the zonules attaching the lens; and the sulci formed on the posterior surface of the iris where the anterior and posterior lens surfaces come together. In another scan method, a combined scan can be made where the arc guide track assembly is moved laterally while the transducer carriage moves along the arc guide track. Before the transducer carriage is moved from one end of the arc guide track and after the transducer carriage has reached the other end of the arc guide track, short lateral linear scans can be made. These short linear scans can increase the image quality of non-specular features of interest such as such as: the angle between the cornea and iris lying behind the sclera; the zonules attaching the lens; and the sulci formed on the posterior surface of the iris where the anterior and posterior lens surfaces come together. In another scan technique, the arcuate and linear motions of the transducer can be fully co-ordinated to optimize the angle of the transducer axis relative to an area of interest, such as for example the area where the zonules connect the lens with the ciliary body.

As will be appreciated, it would be possible to provide for some features of the inventions without providing others. For example, though the embodiments are discussed with reference to an arc scanning device, it is to be understood that the various embodiments may be used with other types of acoustic scanning devices using different transducer motion strategies.

The present invention, in various embodiments, includes components, methods, processes, systems and/or apparatus substantially as depicted and described herein, including various embodiments, sub-combinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, for example for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. For example, the steps may be performed in any order and are not limited to the particular ordering discussed herein.

What is claimed:

1. A method of determining a thickness of a selected region of an eye, wherein the selected region is bounded by a first interface and a second interface, comprising:
   (a) providing an ultrasonic scanner comprising a positioning mechanism, wherein a scan head is positioned by the positioning mechanism, the scan head comprising at least one ultrasound transducer, and wherein the ultrasonic scanner is configured to engage a patient;
   (b) substantially aligning an axis of the at least one ultrasound transducer of the scan head with a z-axis of the positioning mechanism and at least one of an optical axis of the eye, a visual axis of the eye, and any line passing through both the first interface and the second interface;
   (c) moving the positioning mechanism, with the scan head fixed relative to the positioning mechanism, along the z-axis to determine a first z-axis position wherein the at least one ultrasound transducer detects an amplitude of a first A-scan that is substantially a maximum value in proximity of the first interface of the selected region;
   (d) moving the positioning mechanism, with the scan head fixed relative to the positioning mechanism, along the z-axis to determine a second z-axis position wherein the at least one ultrasound transducer detects an amplitude of a second A-scan that is substantially a maximum value in proximity of the second interface of the selected region; and
   (e) subtracting the first z-axis position from the second z-axis position to determine the thickness of the selected region.

2. The method of claim 1 further comprising:
   generating a plurality of A-scans by moving the positioning mechanism and the at least one ultrasound transducer along the z-axis while detecting a plurality of A-scan amplitudes in the selected region, and from at least one of the A-scans determining an acoustic pulse transit time between the first interface and the second interface.

3. The method of claim 2 further comprising:
   determining an average acoustic velocity of the selected region using the thicknesses of the selected region and the acoustic pulse transit time across the selected region by the following formula:

$c = \Delta z / \Delta t$ where c=the average acoustic velocity of the region
and Δz is the thickness of the selected region; and
and Δt is the acoustic pulse transit time across the selected region.

4. The method of claim 1 wherein the selected region is at least one of a cornea, a natural lens, an artificial lens, a phakic lens, an aqueous humour region between the cornea and the natural lens, and a vitreous humour region between one of the lens and a retina.

5. The method of claim 1, further comprising a computer readable medium comprising processor executable instructions that performs at least one of the steps of (b), (c), (d), and (e).

6. The method of claim 4, further comprising a computer readable medium comprising processor executable instructions that performs the steps of (a), (b), (c), (d), and (e).

7. The method of claim 1, wherein the first interface is one of a posterior surface and an anterior surface and the second interface is the other of a posterior and an anterior surface, wherein the posterior and anterior surfaces bound at least one of a cornea, a natural lens, an artificial lens, a phakic lens, an aqueous humour region between the cornea and the natural lens, and a vitreous humour region between one of the lens and a retina.

8. A system for determining a thickness of a selected region of an eye wherein the selected region is bounded by a first interface and a second interface, comprising:
(a) a positioning mechanism which can be moved back and forth along a z-axis;
(b) a scan head that can be positioned by the positioning mechanism; wherein an ultrasound transducer is operably connected to the scan head, wherein the ultrasound transducer can be positioned to emit ultrasound pulses along a path coincident with the z-axis of the positioning mechanism, wherein the scan head is fixed relative to the positioning mechanism when the ultrasound transducer emits ultrasound pulses;
(c) a system for determining a position of the positioning mechanism along the z-axis;
(d) a system for receiving reflected ultrasound pulses, wherein the positioning mechanism positions the scan head along the z-axis to determine a first z-axis position wherein the ultrasound transducer detects an amplitude of a first A-scan that is substantially a maximum in proximity of the first interface of the selected region; wherein the positioning mechanism positions the scan head along the z-axis to determine a second z-axis position wherein the ultrasound transducer detects an amplitude of a second A-scan that is substantially a maximum in proximity of the second interface of the selected region; and wherein the first z-axis position is subtracted from the second z-axis position to determine the thickness of the selected region of the eye.

9. The system of claim 8 further comprising:
an analog-to-digital converter connecting the ultrasound transducer to a computer;
the computer operable to operate the system of claim 8;
a computer readable medium comprising processor executable instructions that, when executed, enables the positioning mechanism to move back and forth by selected amounts, enables the ultrasound transducer to emit pulses at selected times, enables the ultrasound transducer to receive and record reflected ultrasound pulses, and provides an output that determines pulse transit times and distances between the first interface and the second interface.

10. The system of claim 8 wherein a means for determining the position of the positioning mechanism along the z-axis has a spatial resolution of less than 5 microns.

11. The system of claim 9 wherein the analog-to-digital converter has a characteristic frequency of at least 200 MHz.

12. The system of claim 8, wherein the positioning mechanism moves during a scan.

13. The system of claim 8, wherein the ultrasound transducer is connected to a carriage.

14. The system of claim 13, wherein the carriage may be positioned along at least one of a linear guide track and an arcuate guide track.

15. The method of claim 8, wherein the first and second interfaces are specular surfaces.

16. A system, comprising:
(a) a positioning mechanism movable back and forth along a z-axis;
(b) a scan head configured to be positioned by the positioning mechanism; wherein an ultrasound transducer operably connected to the scan head and configured to be positioned to emit ultrasound pulses along a path coincident with the z-axis, wherein the scan head is substantially fixed relative to the positioning mechanism when the ultrasound transducer emits ultrasound pulses;
(c) a system configured to determine, at a selected time, a position of the positioning mechanism along the z-axis; and
(d) a system configured to receive reflected ultrasound pulses; wherein the system determines a thickness of a selected region of an eye, wherein the positioning mechanism positions the scan head along the z-axis to determine a first z-axis position wherein the ultrasound transducer detects an amplitude of a first A-scan that is substantially a maximum; wherein the positioning mechanism positions the scan head along the z-axis to determine a second z-axis position wherein the ultrasound transducer detects an amplitude of a second A-scan that is substantially a maximum; and wherein the first z-axis position is subtracted from the second z-axis position to determine the thickness of the selected region of the eye.

17. The system of claim 16, wherein the imaged region is at least one of a cornea, a natural lens, an artificial lens, a phakic lens, an aqueous humour between the cornea and the natural lens, and a vitreous humour region between one of the lens and a retina.

18. The system of claim 17, wherein the selected region is bounded by a first interface and a second interface, and wherein a plurality of A-scans is generated by moving the positioning mechanism and the ultrasound transducer along the z-axis while detecting a plurality of A-scan amplitudes in the selected region, and from at least one of the A-scans determining an acoustic pulse transit time between the first interface and the second interface.

19. The system of claim 18, further comprising a computer readable medium comprising processor executable instructions that determine an acoustic velocity of a selected region of the eye using the thickness of the selected region of the eye and the acoustic pulse transit time between the first interface and the second interface.

20. The system of claim 18, wherein a B-scan is comprised of the plurality of A-scans wherein at least one acoustic velocity measured for the selected region of the eye is used to convert the acoustic pulse transit time for the selected region to the thickness between the first interface and the second interface of the selected region.

* * * * *